(12) United States Patent
De Wael et al.

(10) Patent No.: US 11,867,704 B2
(45) Date of Patent: Jan. 9, 2024

(54) DETECTING AN ANALYTE IN THE PRESENCE OF AN INTERFERENT

(71) Applicant: UNIVERSITEIT ANTWERPEN, Antwerp (BE)

(72) Inventors: Karolien De Wael, Sint-Gillis-Waas (BE); Mats De Jong, Olen (BE); Anca Stefana Florea, Sibiu (RO); Nick Sleegers, Antwerp (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 632 days.

(21) Appl. No.: 16/756,029

(22) PCT Filed: Oct. 15, 2018

(86) PCT No.: PCT/EP2018/078107
§ 371 (c)(1),
(2) Date: Apr. 14, 2020

(87) PCT Pub. No.: WO2019/076829
PCT Pub. Date: Apr. 25, 2019

(65) Prior Publication Data
US 2020/0309799 A1 Oct. 1, 2020

(30) Foreign Application Priority Data
Oct. 16, 2017 (EP) .................... 17196615

(51) Int. Cl.
*G01N 27/48* (2006.01)
*G01N 33/94* (2006.01)
(Continued)

(52) U.S. Cl.
CPC .......... *G01N 33/94* (2013.01); *G01N 27/327* (2013.01); *G01N 27/4161* (2013.01);
(Continued)

(58) Field of Classification Search
CPC ........................... G01N 27/48; Y10S 436/901
See application file for complete search history.

(56) References Cited

PUBLICATIONS

Mats de Jong et al., Electrochemical fingerprint of street samples for fast on-site screening of cocaine in seized drug powders, Chemical Science, vol. 7, pp. 2364-2370 (2016) (Year: 2016).*
(Continued)

*Primary Examiner* — Joshua L Allen
*Assistant Examiner* — Vivian A Tran
(74) *Attorney, Agent, or Firm* — Workman Nydegger

(57) ABSTRACT

A method for determining a narcotic in a mixture comprising at least one interferant. The method comprises: (a) determining a voltage at which, in absence of the interferant, a voltammetric signal of the narcotic can be detected; (b) contacting an electrode with the mixture comprising the at least one interferant and potentially comprising the narcotic; (c) applying a pretreatment potential to the electrode for a duration of at least 5 seconds, the pretreatment potential measuring between −0.4 V and −2 V versus Ag/AgCl; (d) measuring a voltammetric response of the mixture, the measurement comprising at least the determined voltage; and (e) determining whether the narcotic is present in the mixture by analyzing whether the voltammetric signal of the narcotic, resolved from a voltammetric signal of the interferant, can be detected in the measured voltammetric response.

20 Claims, 31 Drawing Sheets

(51) Int. Cl.
  G01N 27/327    (2006.01)
  G01N 27/416    (2006.01)
  G01N 33/487    (2006.01)
(52) U.S. Cl.
  CPC ....... *G01N 27/48* (2013.01); *G01N 33/48714* (2013.01); *G01N 33/946* (2013.01); *Y10S 436/901* (2013.01)

(56) References Cited

PUBLICATIONS

Zhang et al., Simultaneous detection of hydroquinone and catechol on electrochemical-activated glassy carbon electrode by simple anodic and cathodic polarization, Journal of Solid State Electrochemistry, vol. 21, pp. 735-745 (2017) (Year: 2017).*
Asturias-Arribas et al, Sensitive and selective cocaine electrochemical detection using disposable sensors, Analytica Chimica Acta, vol. 834, pp. 30-36 (2014) (Year: 2014).*
Xu et al., Sensitive determination of dopamine on poly(aminobenzoic acid) modified electrode and the application toward an experimental Parkinsonian animal model, Talanta, vol. 55, Issue 2, pp. 329-336 (2001) (Year: 2001).*
Cao et al., Effects of Surface Pretreatment of Glassy Carbon on the Electrochemical Behavior of V(IV)/V(V) Redox Reaction, Journal of the Electrochemical Society, vol. 163, Issue 7, pp. A1164-A1174 (2016) (Year: 2016).*
Asturias-Arribas et al., CYP450 biosensors based on screen-printed carbon electrodes for the determination of cocaine, Analytica Chimica Acta, vol. 685, Issue 1, pp. 15-20 (2011) (Year: 2011).*
Abedul et al., Voltammetric Determination of Cocaine in Confiscated Samples, Electroanalysis, vol. 3, pp. 409-412 (1991) (Year: 1991).*
Asturias-Arribas et al., Electrochemical determination of cocaine using screen-printed cytochrome P450 2B4 based biosensors, Talanta, vol. 105, pp. 131-134 (2013) (Year: 2013).*
Freitas et al., A portable electrochemical method for cocaine quantification and rapid screening of common adulterants in seized samples, Sensors and Actuators B: Chemical, vol. 243, pp. 557-565 (2017) (Year: 2017).*
Pavlova et al., Studying electrode mechanism and analytical determination of cocaine and its metabolites at the mercury electrode using square-wave voltammetry, Analytica Chimica Acta, vol. 512, Issue 1, pp. 49-56 (2004) (Year: 2004).*
Komorski-Lovric et al., Voltammetric Determination of Cocaine Microparticles, Electroanalysis, vol. 11, No. 2, pp. 120-123 (1999) (Year: 1999).*
Pavlova et al., Studying electrode mechanism and analytical determination of cocaine and its metabolites at the mercury electrode using square-wave voltammetry, Analytica Chimica Acta, vol. 512, pp. 49-56 (2004) (Year: 2004).*
Jiang et al., Highly sensitive electrochemical detection of cocaine on graphene/AuNP modified electrode via catalytic redox-recycling amplification, Biosensors and Bioelectronics, vol. 32, pp. 305-308 (2012) (Year: 2012).*
Aleksic et al., "Simultaneous Determination of Cefotaxime and Desacetylcefotaxime in Real Urine Sample Using Voltammetric and High-Performance Liquid Chromatographic Methods," Talanta, vol. 77, May 29, 2008, pp. 131-137.
Aleksic et al., "Voltammetric Behavior and Square-Wave Voltammetric Determination of Cefotaxime in Urine," Journal of Electroanalytical Chemistry, vol. 593, Jun. 21, 2006, pp. 258-266.
De Jong et al., "Electrochemical Fingerprint of Street Samples for Fast On-Site Screening of Cocaine in Seized Drug Powders," Chemical Science, vol. 7, Jan. 6, 2016, pp. 2364-2370.
De Jong et al., "Levamisole: a Common Adulterant in Cocaine Street Samples Hindering Electrochemical Detection of Cocaine," Analytical Chemistry, vol. 90, No. 8Feb. 23, 2018, pp. 5290-5297.
De Jong et al., "Tackling Poor Specificity of Cocaine Color Tests by Electrochemical Strategies," Analytical Chemistry, vol. 90, No. 11, May 9, 2018, pp. 6811-6819.
Dong et al., "Emodin: A Review of its Pharmacology, Toxicity and Pharmacokinetics," Phytotherapy Research, vol. 30, Apr. 2, 2016, pp. 1207-1218.
Merola et al., "Simple and Suitable Immunosensor for B-lactam Antibiotics Analysis in Real Matrixes: Milk, Serum Urine," Journal of Pharmaceutical and Biomedical Analysis, vol. 106, Jan. 1, 2015, pp. 186-196.
Oliveira et al., "Voltammetric Analysis of Cocaine Using Platinum and Glassy Carbon Electrodes Chemically Modified with Uranyl Schiff Base Films," Mircochemical Journal, vol. 110, May 14, 2013, pp. 374-378.
Prado et al., "B-Lactamase-Based Biosensor for the Electrochemical Determination of Benzylpenicillin in Milk," Sensors and Actuators B: Chemical, vol. 210, Jan. 3, 2015, pp. 254-258.
Feizbakhsh et al., "Simultaneous DPV Determination of Morphine and Codeine Using dsDNA Modified Screen Printed Electrode Strips Coupled with Electromembrane Extraction," International Journal of Medical Research & Health Sciences, ISSN No. 2319-5886, vol. 5, No. 1, May 1, 2016, pp. 206-218.
Temerk et al., "Individual and Simultaneous Square Wave Voltammetric Determination of the Anticancer Drugs Emodin and Irinotecan at Renewable Pencil Graphite Electrodes," Journal of the Brazilian Chemical Society, vol. 24, No. 10, Sep. 4, 2013, pp. 1669-1678.
Wang et al., "Evaluation and Improvement of the Resolution of Voltammetric Measurements," Talanta, vol. 33, No. 5, May 31, 1986, pp. 397-400.
Extended European Search Report from European Application No. EP17196615.3, dated Dec. 13, 2017.
International Search Report and Written Opinion from International Application No. PCT/EP2018/078107, dated Mar. 18, 2019.

* cited by examiner

DETECTING AN ANALYTE IN THE PRESENCE OF AN INTERFERENT

TECHNICAL FIELD OF THE INVENTION

The present invention relates to the detection of an analyte in the presence of an interferent, particularly wherein the analyte is an antibiotic or a narcotic.

BACKGROUND OF THE INVENTION

Cocaine is one of the most used illicit drugs, with a number of 17.1 million global users in 2015 according to the United Nations Office on Drugs and Crime. Cocaine continues to be trafficked primarily from South America to North America and Western and Central Europe. A great deal of attention has been focused on assessing the trafficking routes in order to reduce drug-related crime and its negative health impact. For this purpose, an important role is attributed to the identification of the composition of cocaine seizures (i.e. adulterants, cutting agents and other compounds) which provides police forces with valuable information on the source of the supply and therefore aids tracing the illicit networks. The characterization of cutting agents and adulterants in seized cocaine samples is important from a forensic point of view in order to link different seizures to one original batch as well as for the health implications some of them might have. An important adulterant is, for example, levamisole, a veterinary anthelmintic drug. Levamisole has a detection frequency of 65% in cocaine street samples because it is easy to procure and has similar physicochemical properties and synergistic effects with cocaine. The use of levamisole-laced cocaine poses health risks, such as neutropenia, agranulocytosis, arthralgia, skin necrosis, or leukoencephalopathy.

In general, police officers and custom services use field tests in the form of colour tests. A colour test is a presumptive test that provides an indication of the presence or absence of a compound. Colour tests are used on site as a quick and cheap screening method. The Scott colour test, developed by Scott in 1973, is the most common screening test for cocaine. The test is based on the formation of a blue complex between cocaine and cobalt thiocyanate. There are, however, two important problems associated with the colour tests. Firstly, this conventional technique can be easily influenced by adding certain compounds to the cocaine mixtures, causing the test to show a false negative result. Smugglers are becoming more creative each day in order to get the cargo through customs services and they mainly do this by chemically masking the cocaine with coloured agents that cause the colour test to be negative. Another related popular technique is to mix cocaine with other solid materials like fishmeal, to hide its presence. Secondly, the colour test lacks specificity. The complexation with the cobalt thiocyanate could also occur with other molecules, causing the test to turn blue, thus leading to a false positive result and possible detention of innocent people or economic burden on companies whose cargos are confiscated. Moreover, the test is influenced by temperature. At 4° C. the sensitivity of the test was found to be double compared to room temperature (22° C.), while temperatures over 40° C. decreased the sensitivity of the test more than two-fold in comparison with room temperature. Because of all these concerns, colour test results need further confirmation in the laboratory by more sophisticated techniques such as chromatography or mass spectrometry which are laborious and both time consuming and costly.

Electrochemical techniques, through their simplicity, low cost, fast response, and high sensitivity offer a good alternative for on-site screening of illicit drugs in the presence of cutting agents. For example, de Oliveira et al. report on the detection of cocaine in the presence of cutting agents by means of electrochemistry (de Oliveira, Laura Siqueira, et al. "Voltammetric analysis of cocaine using platinum and glassy carbon electrodes chemically modified with Uranyl Schiff base films." Microchemical Journal 110 (2013): 374-378). However, adulterants and cutting agents commonly interfere with the electrochemical detection of cocaine due to suppressed or overlapping signals, thus making the analysis of cocaine street samples problematic. As such, modification of the electrode surface is typically required to achieve selective cocaine detection, which can be time-consuming and costly.

With respect to antibiotics, the discovery of natural antibiotics, such as penicillin G by Alexander Fleming, brought about the greatest revolution in medicine of the 20th century. After further development and the discovery of other antibiotics, common, yet deadly, diseases such as pneumonia and tuberculosis could be cured and the risk of infection after surgery could be minimized. As a result, the mass-production and use of synthetic and semi-synthetic derivatives of the naturally occurring antibiotics began. However, natural selection exerted itself in the form of antimicrobial resistance (AMR), one of the major health problems threatening modern society. By 2050, an estimated 10 million people will die every year due to AMR. The analysis of antibiotic residues mainly focusses on food samples, such as milk, meat, honey, and eggs. However, it is often overlooked that, for antibiotics, renal recoveries above 90% have been reported. The unchanged antibiotics get released back into the environment where they will contribute to AMR. Therefore, a pressing need for better surveillance in e.g. waste streams has emerged; aimed at rapid, sensitive and selective detection of antibiotics (particularly β-lactam antibiotics and tetracyclines) with the ability of on-site, continual analysis.

In light of the severe threat to human health, many attempts have been made to develop efficient methods to detect antibiotic residues in agricultural products, likewise for monitoring waste waters. A common analytical approach for the determination of antibiotics is liquid chromatographic separation coupled with (tandem) mass spectrometry (LC-MS/MS) or UV/Vis-detection (LC-UV/Vis), preceded by an extensive pre-concentration, such as solid phase extraction. These methodologies are traditionally performed in the lab and have their shortcomings, most prominently among them are their time-consuming nature (hours) and the cost of such analysis (€ 200-300 per analysis), including complex sampling processes, need for specialized analysts and sophisticated instruments. Other approaches in the literature include optical biosensors and capillary electrophoresis (CE), but these often have additional shortcomings on top of the above-mentioned enumeration.

For the on-site detection of antibiotic residues, microbial screening assays and enzyme-linked immunosorbent assay (ELISA) kits are employed as a practical screening method. The microbial tests rely on a simple colour change, no further information can be given like concentration or which antibiotic(s) is present. Well-known examples of microbial tests are the Delvotest® and the Copan Milk Test (CMT), which are based on growth inhibition of acid producing bacteria combined with a pH indicator. These tests are typically optimized for the detection of antibiotic activities in milk. Additionally, they often suffer from low sensitivity towards certain antibiotics (e.g. nafcillin, cephalexin or (oxy)tetracycline). Commercial ELISA kits for the detection of antibiotic residues are available in the form of SNAP-tests. These tests employ enzymes as bio-affinity molecules, making them very sensitive to storage conditions. Furthermore, they are only able to detect a limited scope of antibiotics (typically only a few molecules of the same class), resulting in the use of many tests to screen one sample for a range of antibiotics.

The use of electrochemistry seems an inviting approach to address the above-mentioned drawbacks. For example, amperometric detection was used in the development of immuno- and enzymatic sensors. An immunosensor was for example disclosed in Merola et al. (2015) (Merola, Giovanni, et al. "Simple and suitable immunosensor for β-Lactam antibiotics analysis in real matrixes: Milk, serum, urine." *Journal of pharmaceutical and biomedical analysis* 106 (2015): 186-196); while an enzymatic sensor was for example disclosed in do Prado et al. (2015) (do Prado, Thiago M., et al. "β-Lactamase-based biosensor for the electrochemical determination of benzylpenicillin in milk." *Sensors and Actuators B: Chemical* 210 (2015): 254-258). However, to detect an analyte based on its redox processes, these have to be studied and unravelled. A common issue with electrochemical techniques is that it is not uncommon for a signal of certain antibiotic of interest to be masked (e.g. suppressed or overlapped) by an interferent, such as another antibiotic. This complicates the detection of antibiotics through electrochemical means as the antibiotic of interest may go undetected (false negative) or may be detected when it is not present (false positive).

There is thus still a need in the art for better methods to detect analytes, particularly antibiotics and narcotics, in the presence of an interferent.

SUMMARY OF THE INVENTION

It is an object of the present invention to provide good methods for determining the presence of an analyte, particularly an antibiotic or a narcotic, in a mixture comprising at least one interferent. The above objective is accomplished by methods according to the present invention.

It is an advantage of embodiments of the present invention that a signal of the analyte can be resolved from a signal of the interferent.

It is an advantage of embodiments of the present invention that a high specificity of detection may be obtained.

It is an advantage of embodiments of the present invention that a high sensitivity of detection may be obtained.

It is an advantage of embodiments of the present invention that the determination of the presence of the analyte may be extended beyond the mere detection of the analyte, towards the quantification of the analyte.

It is an advantage of embodiments of the present invention that the method does not necessarily require a lab-setting, and can be easily performed in the field.

It is an advantage of embodiments of the present invention that the method does not necessarily require a highly trained operator to be performed; instead, having a relatively high ease-of-use.

It is an advantage of embodiments of the present invention that the method may be relatively cheap to perform, for example using low cost, disposable electrodes.

In a first aspect, the present invention relates to a method for determining the presence of a narcotic in a mixture comprising at least one interferent. The method comprises: (a) determining a voltage at which, in absence of the interferent, a voltammetric signal of the narcotic can be detected; (b) contacting an electrode with the mixture comprising the at least one interferent and potentially comprising the narcotic; (c) applying a pretreatment potential to the electrode for a duration of at least 5 seconds, preferably at least 60 seconds, yet more preferably at least 200 seconds (e.g. 360 s), the pretreatment potential measuring between −0.4 V and −2 V versus Ag/AgCl, preferably between −0.5 V and −1.2 V; (d) measuring a voltammetric response of the mixture, the measurement comprising at least the determined voltage; and (e) determining whether the narcotic is present in the mixture by analyzing whether the voltammetric signal of the narcotic, resolved from a voltammetric signal of the interferent, can be detected in the measured voltammetric response. In a second aspect, the present invention relates to a use of an electrode coated with a poly(aminobenzoic acid) or poly(phenylenediamine) film for determining the presence of a narcotic in a mixture comprising at least one interferent.

Also described is a method for determining the presence of an antibiotic in a mixture comprising at least one interferent, the method comprising: (a) determining a first voltage at which, in absence of the interferent, a voltammetric signal of the antibiotic at a first pH can be detected; (b) determining a second voltage at which, in absence of the interferent, a voltammetric signal of the antibiotic at a second pH can be detected, the second pH differing from the first pH by at least 1, preferably at least 3; (c) providing the mixture comprising the at least one interferent and potentially comprising the antibiotic; (d) measuring a first voltammetric response of the mixture at the first pH, the measurement comprising at least the first voltage; (e) measuring a second voltammetric response of the mixture at the second pH, the measurement comprising at least the second voltage; and (f) determining whether the antibiotic is present in the mixture by analyzing whether the voltammetric signal of the antibiotic, resolved from a voltammetric signal of the interferent, can be detected in at least one of the first and second voltammetric responses.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIGS. 1-12, 14-19, 22-29, 31-36 and 38-61*a* and 61*b* are voltammetric responses of solutions and mixtures in accordance with exemplary embodiments of the present invention.

Figure 1:
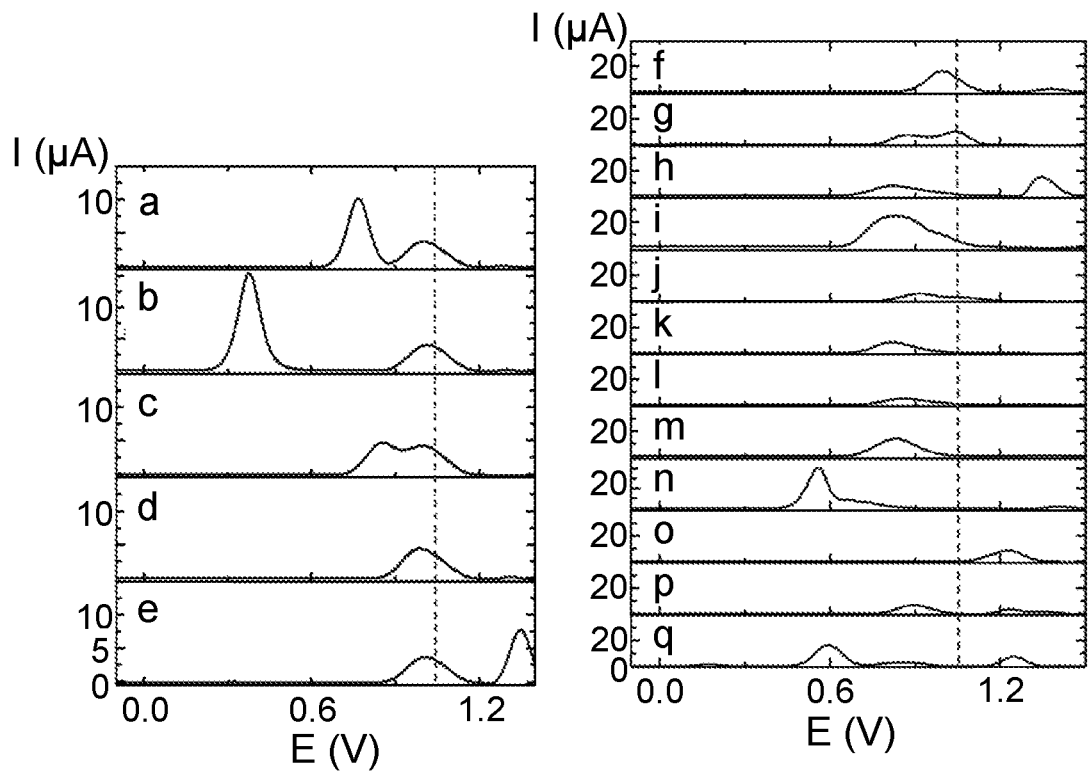

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms over, under and the like in the description and the claims are used for descriptive purposes and not necessarily for describing relative positions. It is to be understood that the terms so used are interchangeable with their antonyms under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures, and techniques have not been shown in detail in order not to obscure an understanding of this description.

The following terms are provided solely to aid in the understanding of the invention.

As used herein, and unless otherwise specified, an interferent is a compound in a measurement sample (i.e. a mixture) that produces readings which overlap with those of the analyte, making analysis more difficult.

As used herein, and unless otherwise specified, reference will be made to "single" and "double" voltammetric scans. Under a "double" scan is understood a scan performed by first sweeping the potential in a first (e.g. negative) direction, followed by a potential sweep in the opposite (e.g. positive) direction, while a "single" scan refers to performing directly a potential sweep in a single (e.g. positive) direction.

As used herein, the specificity of a detection test is quantitatively determined as the ratio of the number of true negative samples and the sum of the number of true negative samples and false positive samples. True negative is considered the number of cases that the test declares negative and that is truly negative, while false positive is the number of cases that the test declares positive but are in fact negative. Likewise, the sensitivity of a detection test is quantitatively determined as the ratio of the number of true positives samples and the sum of the number of true positive samples and false negative samples. True positive is considered the number of cases that the test declares positive and that is truly positive, while false negative is the number of cases that the test declares negative but are in fact positive.

In a first aspect, the present invention relates to a method for determining the presence of a narcotic in a mixture comprising at least one interferent. In a first type of embodiment, the method comprises: (a) determining a voltage at which, in absence of the interferent, a voltammetric signal of the narcotic can be detected; (b) contacting an electrode with the mixture comprising the at least one interferent and potentially comprising the narcotic; (c) applying a pretreatment potential to the electrode for a duration of at least 5 seconds, preferably at least 60 seconds, yet more preferably at least 200 seconds (e.g. 360 s), the pretreatment potential measuring between −0.4 V and −2 V versus Ag/AgCl, preferably between −0.5 V and −1.2 V; (d) measuring a voltammetric response of the mixture, the measurement comprising at least the determined voltage; and (e) determining whether the narcotic is present in the mixture by analyzing whether the voltammetric signal of the narcotic, resolved from a voltammetric signal of the interferent, can be detected in the measured voltammetric response.

It was surprisingly found that applying a pretreatment potential to the electrode advantageously leads to narcotic (e.g. cocaine) signals which are better resolved from those of the interferent (e.g. levamisole), thereby improving the ability to determine the presence of the narcotic. Without being bound by theory, applying the pretreatment potential is believed to facilitate or inhibit certain reactions occurring in the electrochemical process. It may, for example, result in electrochemical "cleaning" of the electrode, create defect sites through the removal of carbon material, which can be highly reactive, and/or have an influence on the oxygen-functional groups at the surface of the electrode. Electrochemical reduction decreases the amount of oxygen-containing functional groups and largely reduces groups, such as C=O and C—O—C, which appears to be beneficial for the electrochemical response towards e.g. cocaine and cocaine-levamisole mixtures. The application of negative potentials also helps desorption of organic compounds at the electrode surface. The electrochemical pretreatment is straightforward and may be less time- and cost-consuming than chemical modification of the electrode surface. It also bypasses the use of reagents required for the modification of electrodes that may cause environmental pollution.

In embodiments, the narcotic may be an illicit narcotic, preferably cocaine. Cocaine is one of the most common narcotics (see background), the quick and accurate detection of which in the field is highly important for e.g. police officers and custom services.

In embodiments, the interferent may be a cutting agent (e.g. a dilutant), an adulterant or a concealing matrix. In embodiments, the cutting agent or adulterant may be selected from phenacetine, paracetamol, lidocaine, ephedrine, caffeine, quinine, codeine, benzocaine, chlorpromazine, dextromethorphan, dextropropoxyphene, diltiazem, hydroxyzine, bupivacaine, levamisole, procaine, promethazine, mannitol, boric acid, heroin, 6-mam, papaverine, noscapine, amphetamine sulfate and glucose. In embodiments, the concealing matrix may be selected from fishmeal, syrup, wash powder and flour. The aforementioned interferents are all relatively commonly found in confiscated street samples or are known to cause issues for the detection of e.g. cocaine using a colour test. It is therefore advantageous that the present invention can determine the presence of the narcotic, e.g. cocaine, in the mixtures comprising these interferents. In preferred embodiments, the interferent may be levamisole. Levamisole is of particular importance because it is an adulterant which is commonly found in street samples which can mask (e.g. hide or suppress) the presence of a narcotic (e.g. cocaine) when using a colour test.

In preferred embodiments, applying the pretreatment potential may be performed after contacting the electrode with the mixture. In other embodiments, applying the pretreatment potential may be performed before contacting the electrode with the mixture.

Applying a pretreatment potential above −0.4 is not typically found to yield an improvement in determining the presence of the narcotic. For pretreatment potentials from −0.5 decreasing down to −1.2 V, an improvement in determining the presence of the narcotic is typically found. Furthermore, the duration for which the pretreatment potential has to be maintained in order to obtain a good improvement decreases with decreasing pretreatment potential. After pretreatment with a potential below −1.2 V, noisier voltammetric responses, and higher background currents are typically observed. This may be due to damage to the electrode.

In preferred embodiments, the pretreatment potential may be applied to the electrode for a duration of at least 300 seconds (e.g. 360 s) and the pretreatment potential may measuring between −0.7 V and −0.9 V (e.g. −0.8).

In embodiments, step d may be performed within 15 min, preferably 5 min, yet more preferably 2 min, most preferably 1 min or 30 s, of performing step c.

In embodiments of the first type, step d may be performed at a pH between 5.5 and 8.5, preferably between 6 and 8, such as 7; or between 10 and 14, preferably between 11 and 13, such as 12. In embodiments, step c may be performed at a pH between 5.5 and 8.5, preferably between 6 and 8, such as 7; or between 10 and 14, preferably between 11 and 13, such as 12.

In embodiments of the first type, the method may comprise: (1) performing a first measurement of (a1) determining a first voltage at which, in absence of the interferent, a voltammetric signal of the narcotic can be detected, (b1) contacting an electrode with the mixture comprising the at least one interferent and potentially comprising the narcotic, (c1) applying a pretreatment potential to the electrode for a duration of at least 5 seconds, preferably at least 60 seconds, yet more preferably at least 200 seconds (e.g. 360 s), the pretreatment potential measuring between −0.4 V and −2 V versus Ag/AgCl, preferably between −0.5 V and −1.2 V, and (d1) measuring a first voltammetric response of the mixture, the measurement comprising at least the first voltage; (2) performing a second measurement of (a2) determining a second voltage, optionally equal to the first voltage, at which, in absence of the interferent, a voltammetric signal of the narcotic can be detected, (b2) contacting an electrode with the mixture comprising the at least one interferent and potentially comprising the narcotic, and (d2) without applying a pretreatment potential as described in step c1, measuring a second voltammetric response of the mixture, the measurement comprising at least the second voltage; and (3) (e) determining whether the narcotic is present in the mixture by analyzing whether the voltammetric signal of the narcotic, resolved from a voltammetric signal of the interferent, can be detected in at least one of the first and second voltammetric responses. In embodiments, step 2 may be performed before step 1. In embodiments, the mixture may be split in a first portion and a second portion, and step 1 may be performed on the first portion and step 2 may be performed on the second portion. In embodiments, step 2 may be performed after step 1 on a same portion of the mixture by waiting for the effects of step c1 to have subsided before performing step d2 (e.g. by allowing at least a time of 1 min, preferably 2 min, yet more preferably 5 min, most preferably 15 min, between step c1 and step d2). In some embodiments, step a1 and a2 may be performed simultaneously. In some embodiments, step b1 and b2 may be performed simultaneously. In embodiments, step a1 may comprise determining a first voltage at which, in absence of the interferent, a voltammetric signal of the narcotic at a first pH can be detected; and step a2 may comprise determining a second voltage at which, in absence of the interferent, a voltammetric signal of the narcotic at a second pH can be detected. In some embodiments, the second pH may differ from the first pH by at least 1, preferably at least 3. In other embodiments, the first and the second pH may differ by 1 or less, such as being equal. The approach of pretreating the electrode can advantageously be combined with a measurement (e.g. a double scan) which is not affected by the pretreatment and determining whether the narcotic is present can be based on both measurements, by determining whether the narcotic signal is resolved in either. Indeed, combining a measurement at two different pH values with a pretreatment potential for at least one of these pH values was observed to yield improved results (see example 2d-e). Moreover, a further indication of where such a combined approach can be beneficial can e.g. be derived from the consolidated table of results under example 3, where for hydroxyzine it is indicated that the pretreatment approach (neither at pH 7 nor 12) did not allow to resolve cocaine, but resolution was possible in the case of double scan at either pH 7 or 12.

In embodiments of the first type, the method may comprise: (1) performing a first measurement of (a1) determining a first voltage at which, in absence of the interferent, a voltammetric signal of the narcotic at a first pH can be detected, (b1) contacting an electrode with the mixture comprising the at least one interferent and potentially comprising the narcotic, (c1) applying a pretreatment potential to the electrode for a duration of at least 5 seconds, preferably at least 60 seconds, yet more preferably at least 200 seconds (e.g. 360 s), the pretreatment potential measuring between −0.4 V and −2 V versus Ag/AgCl, preferably between −0.5 V and −1.2 V, and (d1) measuring a first voltammetric response of the mixture, the measurement comprising at least the first voltage; (2) performing a second measurement of (a2) determining a second voltage at which, in absence of the interferent, a voltammetric signal of the narcotic at a second pH can be detected, the second pH differing from the first pH by at least 1, preferably at least 3, (b2) contacting an electrode with the mixture comprising the at least one interferent and potentially comprising the narcotic, (c2) applying a pretreatment potential to the electrode for a duration of at least 5 seconds, preferably at least 60 seconds, yet more preferably at least 200 seconds (e.g. 360 s), the pretreatment potential measuring between −0.4 V and −2 V versus Ag/AgCl, preferably between −0.5 V and −1.2 V, and d2) measuring a second voltammetric response of the mixture at the second pH, the measurement comprising at least the second voltage; and (3) (e) determining whether the narcotic is present in the mixture by analysing whether the voltammetric signal of the narcotic, resolved from a voltammetric signal of the interferent, can be detected in at least one of the first and second voltammetric responses. In embodiments, step 2 may be performed before step 1. In embodiments, the mixture may be split in a first portion and a second portion, and step 1 may be performed on the first portion and step 2 may be performed on the second portion. In some embodiments, step a1 and a2 may be performed simultaneously. In some embodiments, step b1 and b2 may be performed simultaneously. In some embodiments, step c1 and c2 may be performed simultaneously. The approach of pretreating the electrode can advantageously be also be combined with measuring at different pH values wherein a pretreatment step is applied in each measurement. Determining whether the narcotic is present can then be based on both measurements, by determining whether the narcotic signal is resolved in either. An indication of where such a combined approach can be beneficial can e.g. be derived from the consolidated table of results under example 3, where for chlorpromazine (among others) it is indicated that the pretreatment approach at pH 7 did not allow to resolve cocaine, but the pretreatment approach at pH 12 did; whereas for codeine (among others), the opposite is true.

It will be clear that the methods described hereabove could easily be further expanded with a third measurement (and fourth, etc.). wherein step e could comprise determining whether the narcotic is present in the mixture by analyzing whether the voltammetric signal of the narcotic, resolved from a voltammetric signal of the interferent, can be detected in at least one of the first, second and third voltammetric responses (and fourth, etc.). These additional measurements could for example be performed at different pH values and may or may not include a pretreatment step.

In any embodiment, the electrode may be coated with a poly(aminobenzoic acid) or poly(phenylenediamine) film. Said electrode may, in cases where more than one electrode is used (e.g. a pretreated and a non-pretreated electrode) be at least one of the used electrodes.

In a first type of embodiments, the method may comprise: (—) determining a first voltage at which, in absence of the interferent, a voltammetric signal of the narcotic at a first pH can be detected; (—) determining a second voltage at which, in absence of the interferent, a voltammetric signal of the narcotic at a second pH can be detected, the second pH differing from the first pH by at least 1, preferably at least 3; (—) providing the mixture comprising the at least one interferent and potentially comprising the narcotic; (—) measuring a first voltammetric response of the mixture at the first pH, the measurement comprising at least the first voltage; (—) measuring a second voltammetric response of the mixture at the second pH, the measurement comprising at least the second voltage; and (—) determining whether the narcotic is present in the mixture by analyzing whether the voltammetric signal of the narcotic, resolved from a voltammetric signal of the interferent, can be detected in at least one of the first and second voltammetric responses.

It was surprisingly found within the present invention (in particular in relation to the first and the second type of embodiment) that some interferents may have a voltammetric signal overlapping with or suppressing the voltammetric signal of the narcotic at the first pH, but not at the second pH; likewise other interferents may have a voltammetric signal overlapping with or suppressing the voltammetric signal of the narcotic at the second pH, but not at the first pH. As such, it was discovered that measuring the voltammetric response at both the first and second pH and subsequently determining whether a voltammetric signal of the narcotic, resolved from one of the interferents, can be detected in either of these responses (as opposed to measuring at exclusively at either the first or second pH), advantageously leads to a better performing detection test with a high specificity and sensitivity. This is because a false negative measured at one pH value can still be correct by a positive identification at the other pH value; in other words: the likelihood of measuring a false negative at both pH values simultaneously is significantly reduced compared to measuring a false negative at either of them. Meanwhile, a false positive occurs only when a resolved voltammetric signal is incorrectly attributed to the narcotic. This is a relatively rare occurrence, which is furthermore in many applications preferred over a false negative identification; i.e. it is often less detrimental to incorrectly identify the narcotic to be present, than to incorrectly identify the narcotic to be absent. In embodiments, the method may further comprise expanding the method to a third pH, or a fourth pH, etc.

It will be clear that the order of steps a to e in the first type of embodiment or—to—in the second type of embodiment is not strictly limited to the one presented above, but can be changed as appropriate. For example, step d2 (in the first type of embodiment) or step—(in the second type of embodiment) of measuring at the second pH may be performed before respectively step d1 or step—of measuring at the first pH.

In embodiments of the first or first type, the first pH may be from 5.5 to 8.5, preferably from 6 to 8, and the second pH may be from 10 to 14, preferably from 11 to 13.

In embodiments of the first or first type, measuring the first or second voltammetric response of the mixture at the first or second pH may comprise adjusting the pH of the mixture to the first or second pH and then measuring the corresponding voltammetric response.

In a second type of embodiments, the method may comprise: (0) determining a voltage at which, in absence of the interferent, a voltammetric signal of the narcotic can be detected; (0) contacting an electrode with the mixture comprising the at least one interferent and potentially comprising the narcotic, the electrode being coated with a poly(aminobenzoic acid) or poly(phenylenediamine) film, and (0) measuring a voltammetric response of the mixture, the measurement comprising at least the determined voltage; and (0) determining whether the narcotic is present in the mixture by analyzing whether the voltammetric signal of the narcotic, resolved from a voltammetric signal of the interferent, can be detected in the measured voltammetric response.

With respect to the first and third type of embodiment, it was surprisingly found that coating the electrode with a poly(aminobenzoic acid) or poly(phenylenediamine) film leads to narcotic (e.g. cocaine) signals which are better resolved from those of the interferent (e.g. levamisole), thereby improving the ability to determine the presence of the narcotic. In embodiments of the second type, the electrode may be coated electrochemically. Coating the electrode may, for example, comprise an electrochemical polymerization of the corresponding monomer onto the electrode. In preferred embodiments, the electrode may be coated with a poly(p-aminobenzoic acid) or a poly(o-phenylenediamine). These coatings typically advantageously result in the best detection improvement. In embodiments, poly(o-aminobenzoic acid) may be less preferred. Poly(o-aminobenzoic acid) may easily dissolve in aqueous media and the improvement obtained may be lower.

It will be clear that these embodiments of the first and second type are not mutually exclusive, but that the features of both types may also be combined into one embodiment. As such, the coating of embodiments of the second type may be combined with a measurement at two different pH values in accordance with the first type.

In embodiments of any type, determining the voltage (such as the first and/or second voltage) at which, in absence of the interferent, the voltammetric signal of the narcotic can be detected, may comprise measuring a voltammetric response of the narcotic (e.g. at the first and/or second pH, as appropriate). This measurement may, for example, be performed on the pure narcotic in solution. The determined voltage may, for example, be a voltammetric peak maximum, e.g. at the appropriate pH. In alternative embodiments, the determined voltage may be obtained from a look-up table or from literature. In some cases, a measured voltammetric signal (e.g. a voltammetric peak maximum) may depend on the characteristics of the voltammetric measurement that is performed, e.g. the specific technique used, the scanning speed, the concentration of electrolytes, the type and functionalization of the electrodes, etc. It will be clear that any determined voltage should pertain to conditions that are relevant for subsequently measuring the corresponding voltammetric responses. In particular, step a is preferably performed with the same apparatus, at the same scanning speed, in the same solvent, with the same concentration of electrolytes, and at the same temperature as step d. Also, step b is preferably performed with the same apparatus, at the same scanning speed, in the same solvent, with the same concentration of electrolytes, and at the same temperature as step e.

In embodiments of any type, providing the mixture comprising the at least one interferent and potentially comprising the narcotic may comprise procuring a sample of interest. The sample of interest may, for example, be a confiscated narcotic sample or another sample suspected to comprise the narcotic. In embodiments, providing the mixture may further comprise preparing the sample of interest for measuring the first and second voltammetric response. Preparing the sample may, for example, comprise dissolving the sample, adjusting a concentration of the sample, adding a buffer solution to the sample, etc.

In embodiments of any type, the mixture comprising the at least one interferent and potentially comprising the narcotic typically is a liquid solution.

In embodiments of any type, measuring any voltammetric response may comprise performing a square wave voltammetry. In alternative embodiments, measuring any voltammetric response may comprise performing another voltammetric technique, such as cyclic voltammetry.

In embodiments of any type, measuring any voltammetric response may comprise contacting an electrode with the mixture comprising the at least one interferent and potentially comprising the narcotic. In embodiments, the electrode may be a disposable electrode. In embodiments, the electrode may be a screen printed electrode, e.g. a graphite screen-printed electrode. In embodiments other than those of the second type, the electrode may be bare (i.e. not coated). In embodiments, measuring any voltammetric response may comprise the use of at least two electrodes; e.g. at least a working electrode and a counter electrode, and optionally a reference electrode. In embodiments, measuring any voltammetric response may comprise contacting the at least two electrodes with the mixture. The working electrode may e.g. be a graphite electrode. The counter electrode may e.g. be a carbon electrode. The reference electrode may e.g. be a silver or pseudosilver electrode. In embodiments, the at least two electrodes may be present on a common substrate. The latter is for example typically the case for screen-printed electrodes.

In embodiments of any type, measuring any voltammetric response may comprise sweeping a potential across a potential range in a first direction. In embodiments, the potential range may be from −0.5 to 2 V, preferably from −0.1 to 1.5 V. In embodiments, sweeping a potential across a potential range may comprise increasing or decreasing the potential in a plurality of steps. In embodiments, the steps may have a constant height. In embodiments, the steps may have a height of 5 mV. In embodiments, prior to measuring any voltammetric response, the potential may be swept across the potential range in an opposite second direction. Sweeping the potential across the potential range in an opposite second direction prior to measuring, which may also be referred to as performing a double scan, can advantageously have a beneficial effect on the ability to resolve different peaks in the obtained voltammetric response (e.g. by reducing an overlap between peaks).

In embodiments of any type, determining whether the narcotic is present in the mixture may comprise determining whether a voltammetric peak maximum can be discerned within a predetermined range. In embodiments, determining whether the narcotic is present in the mixture may comprise determining whether a voltammetric fingerprint of the narcotic (e.g. a combination of two or more peaks at predetermined locations, optionally taking into account their relative intensity) can be discerned. In embodiments, determining whether the narcotic is present in the mixture may comprise instructions implemented on a computer system; e.g. by the use of peak recognition software. Depending on the specifics of the situation, a number of criteria are available to the skilled person to decide whether or not the voltammetric signal of the narcotic is resolved from a voltammetric signal of the interferent. One parameter in selecting an appropriate criterion may, for example, be a relative intensity between two voltammetric signals. If two peaks are of comparable intensity (e.g. the peak maxima do not differ by more than 20%) a suitable criterion can be to consider two peaks as resolved if the separation between the two peak maxima is at least as large as their full width at half maximum (FWHM). A different criterion that may be used (e.g. when the peak maxima differ by more than 20%) is to consider two peaks as resolved if the separation between the two peak maxima is at least 50 mV. Further methods are for example discussed by Wang et al. (Wang, Joseph, and Bassam Freiha. "Evaluation and improvement of the resolution of voltammetric measurements." Talanta 33.5 (1986): 397-400).

In embodiments of any type, determining the presence of the narcotic may comprise quantifying a concentration of the narcotic. Depending on the application that is envisioned, it may be beneficial to not merely detect the presence of the narcotic but to also quantify the concentration of the narcotic in the measured sample. In other embodiments, simply detecting the narcotic may be sufficient. In embodiments, quantifying a concentration of the antibiotic may comprise establishing a relationship between a characteristic of the voltammetric signal of the antibiotic and the concentration of the antibiotic. In embodiments, the characteristic may be a voltammetric signal intensity (e.g. maximum peak intensity) or an area under the voltammetric signal (e.g. an area under the peak). In embodiments, quantifying a concentration of the antibiotic may comprise making a calibration curve.

In a second aspect, the present invention relates to a use of an electrode coated with a poly(aminobenzoic acid) or poly(phenylenediamine) film for determining the presence of a narcotic in a mixture comprising at least one interferent.

In embodiments, any feature of any embodiment of the second aspect may independently be as correspondingly described for any embodiment of any of the other aspects.

Also disclosed is a method for determining the presence of an antibiotic in a mixture comprising at least one interferent, the method comprising: (a) determining a first voltage at which, in absence of the interferent, a voltammetric signal of the antibiotic at a first pH can be detected; (b) determining a second voltage at which, in absence of the interferent, a voltammetric signal of the antibiotic at a second pH can be detected, the second pH differing from the first pH by at least 1, preferably at least 3; (c) providing the mixture comprising the at least one interferent and potentially comprising the antibiotic; (d) measuring a first voltammetric response of the mixture at the first pH, the measurement comprising at least the first voltage; (e) measuring a second voltammetric response of the mixture at the second pH, the measurement comprising at least the second voltage; and (f) determining whether the antibiotic is present in the mixture by analyzing whether the voltammetric signal of the antibiotic, resolved from a voltammetric signal of the interferent, can be detected in at least one of the first and second voltammetric responses.

It was surprisingly found within the present invention that some interferents may have a voltammetric signal overlapping with or suppressing the voltammetric signal of the antibiotic at the first pH, but not at the second pH; likewise other interferents may have a voltammetric signal overlapping with or suppressing the voltammetric signal of the antibiotic at the second pH, but not at the first pH. As such, it was discovered that measuring the voltammetric response at both the first and second pH and subsequently determining whether a voltammetric signal of the antibiotic, resolved from one of the interferents, can be detected in either of these responses (as opposed to measuring at exclusively at either the first or second pH), advantageously leads to a better performing detection test with a high specificity and sensitivity. This is because a false negative measured at one pH value can still be corrected by a positive identification at the other pH value; in other words: the likelihood of measuring a false negative at both pH values simultaneously is significantly reduced compared to measuring a false negative at either of them. Meanwhile, a false positive occurs only when a resolved voltammetric signal is incorrectly attributed to the antibiotic. This is a relatively rare occurrence, which is furthermore in many applications preferred over a false negative identification; i.e. it is often less detrimental to incorrectly identify the antibiotic to be present than to incorrectly identify the antibiotic to be absent. In embodiments, the method may further comprise expanding the method to a third pH, or a fourth pH, etc.

It will be clear that the order of steps is not strictly limited to the one presented above but can be changed as appropriate. For example, step (e) of measuring at the second pH may be performed before step (d) of measuring at the first pH. Similarly, step (b) can be performed before step (a).

In embodiments, the antibiotic may be a β-lactam antibiotic, preferably a cephem, yet more preferably a cephalosporin. These compounds have in common that they all possess the characteristic β-lactam ring. The β-lactam antibiotics advantageously constitute the most important family of antibiotics in terms of broad-spectrum activity, availability, and prescription volume. This is also reflected in the number of penicillins and cephalosporins that are present on the WHO list of essential medicine. As such, determining the presence of these antibiotics may typically be more important, or more common, than determining the presence of rarer antibiotics. In embodiments, the cephalosporin may, for example, be cephalexin, cefadroxil, cefacetrile or cefquinome. In other embodiments, the β-lactam antibiotic may be a penicillin. In yet other embodiments, antibiotic may be a tetracycline.

In embodiments, the interferent may be a further antibiotic, for example, another β-lactam antibiotic (e.g. another cephalosporin). Interference from antibiotics which are structurally related to the antibiotic analyte, for example, those coming from the same family, may be relatively common and may be more difficult to resolve using other detection techniques.

In embodiments, the first pH may be from 5 to 9, preferably from 6 to 8, and the second pH may be from 0 to 4, preferably from 1 to 3.

In embodiments, determining the first and/or second voltage may comprise measuring a voltammetric response of the antibiotic at the first and/or second pH, respectively. This measurement may, for example, be performed on the pure antibiotic in solution. The first and/or second voltage may, for example, be a voltammetric peak maximum at the corresponding pH. In alternative embodiments, the first and/or second voltage may be obtained from a look-up table or from literature. In some cases, a measured voltammetric signal (e.g. a voltammetric peak maximum) may depend on the characteristics of the voltammetric measurement that is performed, e.g. the specific technique used, the scanning speed, the concentration of electrolytes, the type and functionalization of the electrodes, etc. It will be clear that the first and second voltages determined in step (a) and (b) should pertain to conditions that are relevant for measuring the first and second voltammetric responses in step (d) and (e). In particular, step (a) is preferably performed with the same apparatus, at the same scanning speed, in the same solvent, with the same concentration of electrolytes, and at the same temperature as step (d). Also, step (b) is preferably performed with the same apparatus, at the same scanning speed, in the same solvent, with the same concentration of electrolytes, and at the same temperature as step (e).

In embodiments, providing the mixture comprising the at least one interferent and potentially comprising the antibiotic may comprise procuring a sample of interest. The sample of interest may, for example, be a waste water sample or a sample from an agricultural product. In embodiments, providing the mixture may further comprise preparing the sample of interest for measuring the first and second voltammetric response. Preparing the sample may, for example, comprise dissolving the sample, adjusting a concentration of the sample, adding a buffer solution to the sample, etc.

In embodiments, measuring the first or second voltammetric response of the mixture at the first or second pH may comprise adjusting the pH of the mixture to the first or second pH and then measuring the corresponding voltammetric response.

In embodiments, measuring any voltammetric response may comprise performing a square wave voltammetry. In alternative embodiments, measuring any voltammetric response may comprise performing another voltammetric technique, such as cyclic voltammetry.

In embodiments, measuring any voltammetric response may comprise contacting an electrode with the mixture comprising the at least one interferent and potentially comprising the antibiotic. In embodiments, the electrode may be a disposable electrode. In embodiments, the electrode may be a screen printed electrode, e.g. a graphite screen-printed electrode. In embodiments, the electrode may be bare (i.e. not coated). In embodiments, measuring any voltammetric response may comprise the use of at least two electrodes; e.g. at least a working electrode and a counter electrode, and optionally a reference electrode. In embodiments, measuring any voltammetric response may comprise contacting the at least two electrodes with the mixture. The working electrode may e.g. be a graphite electrode. The counter electrode may e.g. be a carbon electrode. The reference electrode may e.g. be a silver or pseudosilver electrode. In embodiments, the at least two electrodes may be present on a common substrate. The latter is for example typically the case for screen-printed electrodes.

In embodiments, measuring any voltammetric response may comprise sweeping a potential across a potential range in a first direction. In embodiments, the potential range may be from −0.2 to 1.6 V, preferably from 0.0 to 1.4 V. In embodiments, sweeping a potential across a potential range may comprise increasing or decreasing the potential in a plurality of steps. In embodiments, the steps may have a constant height. In embodiments, prior to measuring any voltammetric response, the potential may be swept across the potential range in an opposite second direction. Sweeping the potential across the potential range in an opposite second direction prior to measuring, which may also be referred to as performing a double scan, can advantageously have a beneficial effect on the ability to resolve different peaks in the obtained voltammetric response (e.g. by reducing an overlap between peaks).

In embodiments, determining whether the antibiotic is present in the mixture may comprise determining whether a voltammetric peak maximum can be discerned within a predetermined range. In embodiments, determining whether the antibiotic is present in the mixture may comprise determining whether a voltammetric fingerprint of the antibiotic (e.g. a combination of two or more peaks at predetermined locations, optionally taking into account their relative intensity) can be discerned. In embodiments, determining whether the antibiotic is present in the mixture may comprise instructions implemented on a computer system; e.g. by the use of peak recognition software. Depending on the specifics of the situation, a number of criteria are available to the skilled person to decide whether or not the voltammetric signal of the antibiotic is resolved from a voltammetric signal of the interferent. One parameter in selecting an appropriate criterion may, for example, be a relative intensity between two voltammetric signals. If two peaks are of comparable intensity (e.g. the peak maxima do not differ by more than 20%) a suitable criterion can be to consider two peaks as resolved if the separation between the two peak maxima is at least as large as their full width at half maximum (FWHM). A different criterion that may be used (e.g. when the peak maxima differ by more than 20%) is to consider two peaks as resolved if the separation between the two peak maxima is at least 50 mV. Further methods are for example discussed by Wang et al. (Wang, Joseph, and Bassam Freiha. "Evaluation and improvement of the resolution of voltammetric measurements." Talanta 33.5 (1986): 397-400).

In embodiments, determining the presence of the antibiotic may comprise quantifying a concentration of the antibiotic. Depending on the application that is envisioned, it may be beneficial to not merely detect the presence of the antibiotic but to also quantify the concentration of the antibiotic in the measured sample. In other embodiments, simply detecting the antibiotic may be sufficient. In embodiments, quantifying a concentration of the antibiotic may comprise establishing a relationship between a characteristic of the voltammetric signal of the antibiotic and the concentration of the antibiotic. In embodiments, the characteristic may be a voltammetric signal intensity (e.g. maximum peak intensity) or an area under the voltammetric signal (e.g. an area under the peak). In embodiments, quantifying a concentration of the antibiotic may comprise making a calibration curve.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

Example 1: Electrochemical Detection of Cocaine

Cocaine hydrochloride was purchased from Lipomed (Arlesheim, Switzerland). Standards of phenacetine, diltiazem, lidocaine, procaine, hydroxyzine, benzocaine, ephedrine, dextromethorphan, dextropropoxyphene, bupivacaine, and paracetamol were purchased from Sigma-Aldrich (Diegem, Belgium). Standards of benzoic acid, chlorpromazine, promethazine, diphenhydramine, and levamisole were purchased from Acros Organics (Geel, Belgium). Standards of caffeine and boric acid were purchased from VWR Chemicals (Leuven, Belgium).

Square wave voltammetry (SWV) measurements were performed using an Autolab potentiostat/galvanostat (PGSTAT 302N, ECOCHEMIE, The Netherlands) controlled by NOVA software. Phosphate buffer 20 mM containing 100 mM KCl (PBS) of pH 7 and pH 12 was used as supporting electrolyte for electrochemical measurements. For the measurements, 50 µL solution was applied immediately after preparation on the surface of disposable ItalSens graphite screen-printed electrodes (GSPE) containing a graphite working electrode (3 mm diameter), a carbon counter electrode and a (pseudo)silver reference electrode (PalmSens, The Netherlands). The single scan SWV parameters were as follows: potential range −0.1V to 1.5V, step potential 5 mV, amplitude 25 mV, and frequency 10 Hz. For an SWV double scan, the potential was firstly swept from 1.5V to −0.1V, before performing the scan as described above. All results obtained by SWV were presented after baseline correction using the mathematical algorithm "moving average" (window=1) contained within NOVA software, which improves the visualization and identification of the peaks over the baseline. All electrochemical experiments were performed at room temperature.

Color tests were performed using a commercially available cocaine/crack Scott test (M.M.C. International B. V, The Netherlands) by adding approximately 1 mg sample powder to the test vial, homogenizing with the spatula for 30 seconds and evaluating visually the color in the vial.

It should be noted that while the present example focusses on cocaine as narcotic, similar experiments can be performed for other narcotics (e.g. heroin) and their interferents, and comparable results can be obtained.

Example 1a: Electrochemical Response of Cocaine and Cutting Agents at pH 7 by SWV Single Scan We now refer to FIG. 1. The influence of common cutting agents on the electrochemical signal of cocaine was studied at pH 7. For this purpose binary mixtures of cocaine and cutting agents were analyzed by an SWV single scan and compared with the SWV of the pure compounds. Pure cocaine gave rise to an oxidation peak at 1.04V (±10 mV) in PBS pH 7, attributed to the oxidation of the tertiary amine; this characteristic redox potential of pure cocaine at pH 7 is indicated in FIG. 1 by a dashed line across each voltammogram. As seen at the left in FIG. 1, phenacetine (FIG. 1a), paracetamol (FIG. 1b), lidocaine (FIG. 1c), ephedrine (FIG. 1d) and caffeine (FIG. 1e) show no significant influence on the oxidation signal of cocaine, allowing the simultaneous detection by means of a quick single SWV scan at pH 7 and automated peak recognition (1.04 V±10 mV).

However, the presence of other cutting agents interferes with the electrochemical detection of cocaine as seen at the right of FIG. 1. Quinine (FIG. 1f) and codeine (FIG. 1g) for example exhibit an oxidation peak around 1.04 V, overlapping the peak of cocaine at 1.04 V and thus leading to false positive results if cocaine wouldn't have been present. Other cutting agents suppress or shift the peak of cocaine, thus leading to false negative results: diltiazem (FIG. 1h), hydroxyzine (FIG. 1i), bupivacaine (FIG. 1j), benzocaine (FIG. 1k), dextropropoxyphene (FIG. 1l), procaine (FIG. 1m), promethazine (FIG. 1n), levamisole (FIG. 1o), dextromethorphan (FIG. 1p), and chlorpromazine (FIG. 1q).

Figure 2:
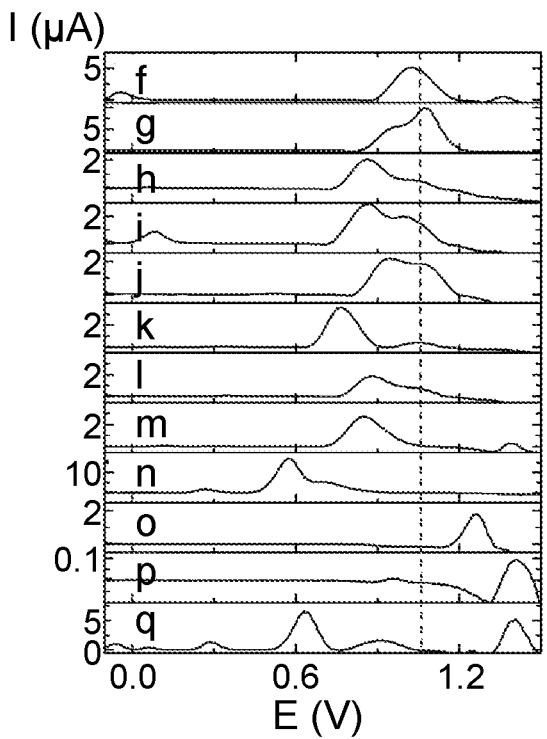

Example 1b: Electrochemical Response of Cocaine and Cutting Agents at pH 7 by SWV Double Scan We now refer to FIG. 2. A double SWV scan was performed for all cocaine-cutting agent solutions that led to the suppression of the cocaine signal in single SWV (see example 1a). A conditioning potential of 1.5V was firstly applied for 5 seconds, followed by a first scan sweeping the potential negatively from 1.5V to −0.1V. Afterwards, the usual forward SWV scan was performed. The dashed line in FIG. 2 again indicates the characteristic redox potential of pure cocaine at pH 7, located at 1.04V (±10 mV). As seen in FIG. 2, the peak of cocaine was slightly shifted in binary mixtures, however, this does not pose a problem for automated cocaine detection. The double scan allowed to reveal the oxidation peak of cocaine in binary mixtures with diltiazem (FIG. 2h), hydroxyzine (FIG. 2i), bupivacaine (FIG. 2j), benzocaine (FIG. 2k) and dextropropoxyphene (FIG. 2l), solving the problem of false negatives that occurred in example 1a for these compounds. Quinine (FIG. 2f), however, still influenced the detection of cocaine, due to overlapping signals. With regard to codeine (FIG. 2g), codeine showed a second oxidation peak at around the same potential as cocaine (1.05V). Although the intensity of the peak at 1.05V was increasing in the mixture with cocaine (and can thus be attributed to the presence of cocaine in the sample), in case of a fast screening it was difficult to discriminate whether the peak is due to the presence of cocaine or codeine. It was, however, important to notice that quinine and codeine are not common cutting agents in cocaine street samples, but are present mostly in heroin street samples. Therefore, finding these compounds in combination with cocaine is unlikely.

Running a reverse scan before the forward SWV scan can thus contribute to an improved signal by reduction and/or desorption of any possible impurities present at the electrode surface and improvement of the electrocatalytic effect. For procaine (FIG. 2m), promethazine (FIG. 2n), levamisole (FIG. 2o), dextromethorphan (FIG. 2p), and chlorpromazine (FIG. 2q), there was no added value of a double scan, as the signal of cocaine was still suppressed.

Example 1c: Electrochemical Response of Cocaine and Cutting Agents at pH 12

Figure 3:
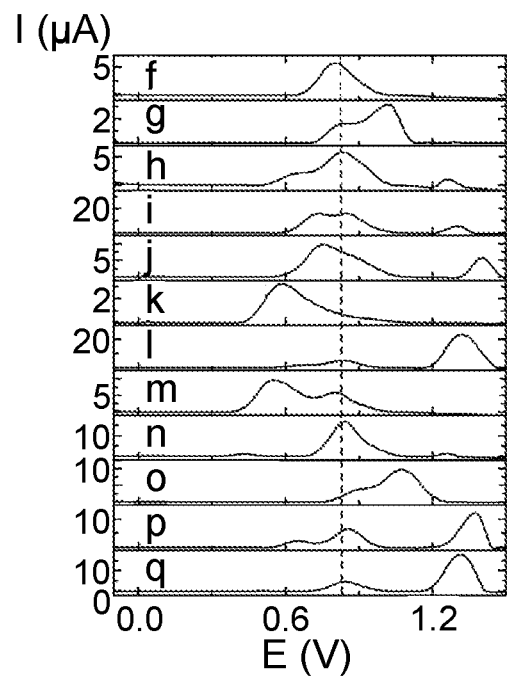

We now refer to FIG. 3. As was also observed for antibiotics (see example 4), the pH of the electrolyte solution has an influence on the electrochemical behaviour of certain compounds. When the pH increases from 7 to 12 the peak current of cocaine is increasing and the peak potential shifts to a less positive value (from 1.04V to 0.83V); this characteristic redox potential of pure cocaine at pH 12 is indicated in FIG. 3 by a dashed line. Taking that effect into consideration, the electrochemical behaviour at pH 12 of the cutting agents that have an influence on the cocaine signal at pH 7 were studied, both as pure compounds (not shown) and in binary mixtures with cocaine (FIG. 3). Altering the pH of the electrolyte allowed to reveal the oxidation peak of cocaine in binary mixtures with several cutting agents, after a single SWV scan: bupivacaine (FIG. 3j), dextropropoxyphene (FIG. 3l), promethazine (FIG. 3n), levamisole (FIG. 3o), dextromethorphan (FIG. 3p), and chlorpromazine (FIG. 3q). For diltiazem (FIG. 3h) and procaine (FIG. 3m) the signal of cocaine in the mixture was also detectable at pH 12, but only after performing a double SWV scan. A double scan at pH 12 was further performed in an effort to reveal the characteristic peaks of cocaine and cutting agents for which a single scan did not perform well. Quinine (FIG. 3f) and codeine (FIG. 3g) present overlapping signals with cocaine also at pH 12, in both single and double scans, however as previously mentioned, they are not common cutting agents in cocaine street samples (unlike what is sometimes reported incorrectly). Adjusting the pH to 12 did not show any improvement in the analysis of cocaine-hydroxyzine (FIG. 3i) and cocaine-benzocaine (FIG. 3k) mixtures. The hydroxyzine oxidation signal overlaps with the cocaine signal, while benzocaine suppresses it, both in a single and a double scan. However, the detection of cocaine in their presence is possible by performing a double scan at pH 7 as previously shown in example 1b.

Example 1d: Electrochemical Methods Versus Color Tests for the Analysis of Cocaine Street Samples In order to investigate the viability of the developed electrochemical methods for determining the presence of cocaine in authentic samples encountered on the street, in harbors or airports, several confiscated street samples were tested with the developed electrochemical strategies and compared to the color test so as to determine the presence of cocaine and investigate any possible false negative samples. The street samples were provided by the National Institute of Criminalistics and Criminology (NICC) of Belgium and were previously analyzed qualitatively and quantitatively by gas-chromatography-mass spectrometry and gas chromatography-flame ionization detection, respectively.

Firstly, authentic street samples were analyzed with commercial Scott color tests in order to assess the specificity of the color test and identify false negatives and false positives. Color tests were performed according to the producer's instructions, by adding more than 1 mg sample powder to the test vial, homogenizing for 10 seconds and observing the color visually.

Secondly, samples were further investigated by means of electrochemical methods. For this purpose, more than 1 mg of street sample was dissolved in PBS buffer pH 7 and pH 12, respectively and analyzed by SWV.

The results of the different tests are consolidated in the following table:

| Sample composition | | | Color | SWV | |
|---|---|---|---|---|---|
| No | Compounds | wt % | test | pH 7 | pH 12 |
| 1 | Cocaine | 98 | P | P | P |
| 2 | Cocaine block | 100 | P | P | P |
| 3 | Cocaine | 76 | P | P | P |
|   | Caffeine | 3 | | | |
|   | Hydroxyzine | 10 | | | |
|   | Lidocaine | <1 | | | |
| 4 | Cocaine | 73 | P | P | P |
|   | Phenacetine | 17 | | | |
| 5 | Cocaine | 70 | P | P, DS | P |
|   | Levamisole | 23 | | | |
| 6 | Cocaine | 31 | P | P, SS | P |
|   | Levamisole | 6 | | | |
|   | Phenacetine | 3 | | | |
|   | Manitol | * | | | |
| 7 | Cocaine | 22 | P | P | P |
|   | Phenacetine | 8 | | | |
|   | Caffeine | 16 | | | |
|   | Lidocaine | 12 | | | |
|   | Levamisole | 2 | | | |
|   | Benzocaine | * | | | |
| 8 | Cocaine | 7 | P | FN | FN |
|   | Phenacetine | 11 | | | |
|   | Caffeine | 23 | | | |
|   | Lidocaine | 3 | | | |
|   | Levamisole | 41 | | | |
| 9 | Cocaine | 22 | FN | P | FN |
|   | Levamisole | 9 | | | |
|   | Lidocaine | * | | | |
|   | Caffeine | <1 | | | |
| 10 | Cocaine | 19 | FN | P | P |
|   | Paracetamol | 73 | | | |
|   | Levamisole | 2 | | | |
| 11 | Cocaine | 30 | FN | P | P |
|   | Boric acid | * | | | |
| 12 | Cocaine in fishmeal | 17 | FN | P | P |
| 13 | Cocaine in Sirup bottle | * | FN | P | FN |
| 14 | Cocaine | 26 | FN | P | FN |
|   | Levamisole | 9 | | | |
| 15 | Heroin | 58 | FP | FP | FP |
|   | Caffeine | 13 | | | |
|   | 6-mam | 8 | | | |
|   | Papaverine | <1 | | | |
|   | Noscapine | 2 | | | |
| 16 | Cocaine | 10 | P | P, SS | P |
|   | Amphetamine sulphate | 42 | | | |
|   | Caffeine | 2 | | | |
|   | Phenacetine | 11 | | | |
|   | Lidocaine | 2 | | | |
| 17 | Glucose | * | N | N | N |
|   | Chlortetracycline | * | | | |
| 18 | Wash powder | * | N | N | N |
| 19 | Boric Acid | * | N | N | N |
| 20 | Phenacetine | 37 | N | N, DS | N |
|   | Lidocaine | 7 | | | |
| 21 | Flour | * | N | N | N |
| 22 | Phenacetine | 100 | N | N | N |

DS, double scan;
SS, single scan;
N, true negative;
P, true positive;
FN, false negative;
FP, false positive;
*, the compound was identified, but not quantified.

As seen in this table, the color tests revealed the presence of cocaine in samples 1-8 and 16; moreover, cocaine could also be easily detected in these samples by a fast SWV scan at either pH 7 or pH 12. In sample 5, due to the presence of levamisole which was suppressing the peak of cocaine at pH 7, cocaine could only be detected by running a double scan at pH 7 or by adjusting the pH to 12. In sample 6 the amount of levamisole was more than five folds less than the amount of cocaine whilst phenacetine and mannitol had no influence on the oxidation peak of cocaine. Thus, cocaine could be easily identified in this sample by a single SWV scan and/or by adjusting the pH to 12. Sample 7 contained levamisole and benzocaine, both of which had an influence on the oxidation signal of cocaine as shown in section 3.3. Thus, when SWV is performed at pH 7, only a small shoulder was observed for cocaine, while the detection of cocaine at pH 12 was more straightforward. Cocaine in sample 8 could not be detected, probably due to the low amount of cocaine 7% (m/m) compared to levamisole (around 6 folds more), which could be the reason of peak suppression at both pH 7 and pH 12. The positive color test, in this case, might be due to the presence of levamisole in a high amount which was shown to give a false positive in color tests.

Color tests gave false negative results for samples 9-14. It should be noted that four of these samples are inherently colored. The color test just assumes the color of the powder, again emphasizing one of the weaknesses of the color test. Most of these problems could, however, be easily resolved by analyzing the sample with SWV, proving the utility of the electrochemical method in overcoming the lack of specificity of color tests. Sample 9 gave a false negative SWV result at pH 12, probably due to the higher amount of lidocaine present in the sample. Experiments on a mixture of lidocaine:cocaine 1:1 at pH 12 showed only one broad peak at 0.8V (data not shown), instead of two separate peaks at 0.6V (lidocaine) and 0.8V (cocaine). Thus, the concentration of cocaine in the sample and the cocaine/cutting agent ratio may play a role in the outcome of the electrochemical measurements. However, the proposed SWV strategy can be applied to most cocaine street samples as the average minimum purity between all EU countries for confiscated cocaine samples was 14% in 2015.

The remaining negative samples 17-22, which could visually be mistaken for cocaine, did not present a problem for both the color test and the electrochemical approach. Sample 15 tested false positive for both the color test and electrochemical tests, but since heroin is another major illegal narcotic, the overlap of its signal with the cocaine signal does not present a major problem.

Figure 4:
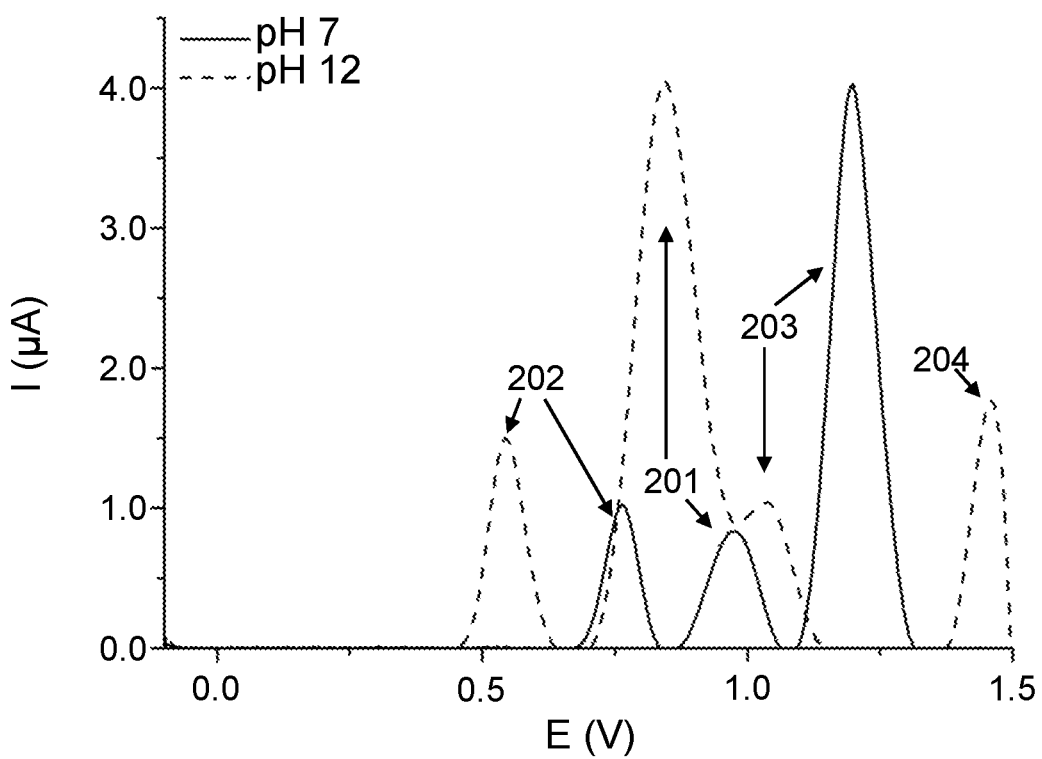
Figure 5:
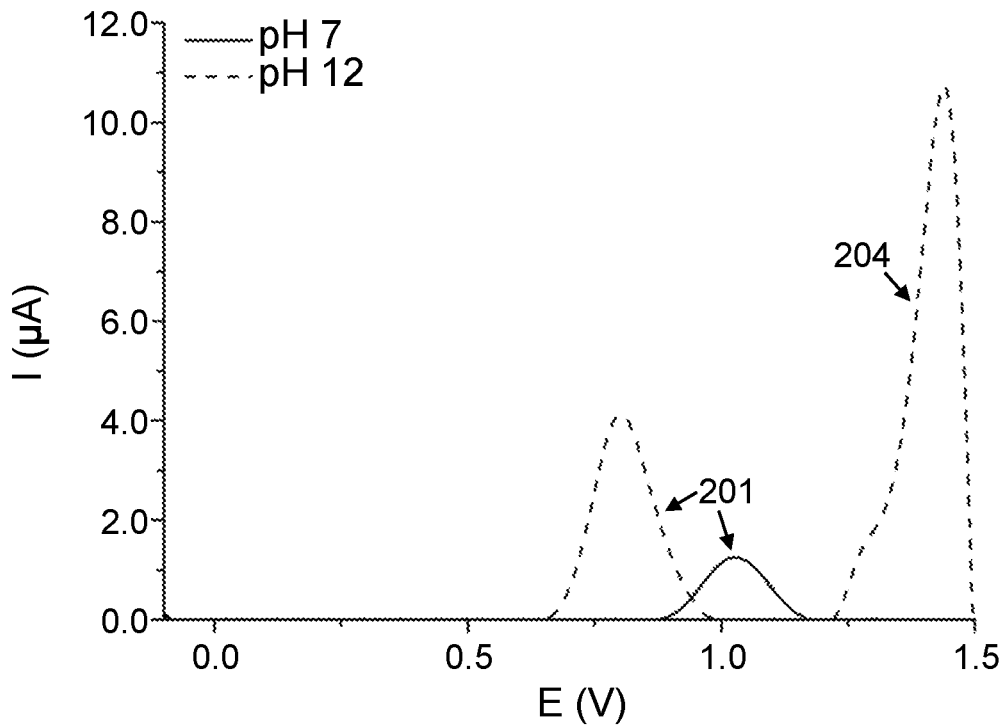

We now refer to FIGS. 4 and 5. The fingerprint of the cutting agents could also be revealed in the analyzed samples. FIGS. 4 and 5 present the exemplary results obtained for sample 6 (FIG. 4) and 12 (FIG. 5). The square wave voltammograms of sample 6 clearly show that cocaine (201) can be detected in adulterated street samples at both pH 7 (solid line) and pH 12 (dashed line), with higher peak intensity at pH 12. The electrochemical oxidation signal of the cutting agents phenacetine (202) and levamisole (203) can also be detected. FIG. 5 illustrates that cocaine could be detected by means of SWV at pH 7 (solid line) and pH 12 (dashed line) even in more complex matrices where color test fail, such as fishmeal samples. The peaks (204) at around 1.45V were attributed to the substrate.

As a form of validation, the sensitivity and specificity of the color test and the electrochemical method were determined for these street samples. For this assessment, the samples giving a debatable color test result were considered positive. The sensitivity of the color test was found to be 0.68, while the specificity was found to be 0.75. For the 22 samples that were tested with the electrochemical approach, the sensitivity of the electrochemical test was found to be 0.93 and the specificity 0.86. The electrochemical approach thus scored significantly better for sensitivity and even the specificity was already improved; this is particularly noteworthy since almost none of the measured negative street samples contain compounds for which the color test results in a false positive (e.g. bupivacaine, chlorpromazine, dextromethorphan, dextropropoxyphene, diltiazem, diphenhydramine, heroin, hydroxyzine, levamisole, lidocaine, promethazine or quinine).

Example 2: Electrochemical Detection of Cocaine in the Presence of Levamisole

Cocaine hydrochloride standard was purchased as a powder from Lipomed (Arlesheim, Switzerland). Levamisole hydrochloride was purchased from Acros Organics (Geel, Belgium). Three seized street samples were provided by the National Institute of Criminalistics and Criminology (NICC) of Belgium. The street samples were analyzed qualitatively and quantitatively by gas chromatography-mass spectrometry (GC-MS) and gas chromatography-flame ionization detection (GC-FID), to establish their chemical composition. Potassium monophosphate, potassium chloride, potassium hydroxide were purchased from Sigma-Aldrich (Overijse, Belgium). A solution of 20 mM phosphate buffer containing 100 mM KCl (PBS) was used as supporting electrolyte and the pH was adjusted to the desired value using a 100 mM KOH solution. All aqueous solutions were prepared using Milli-Q water (R>18 MΩcm). The reagents were of analytical grade and used without supplementary purification.

Square wave voltammetry (SWV) measurements were performed as described for example 1.

It should be noted that while the present example focusses on cocaine as narcotic and levamisole as interferent, similar experiments can be performed for other narcotics (e.g. heroin) and/or other interferents, and comparable results may be obtained (cf. example 3).

Example 2a: Voltammetric Behavior of Cocaine-Levamisole Binary Mixtures at pH 7

Figure 6:
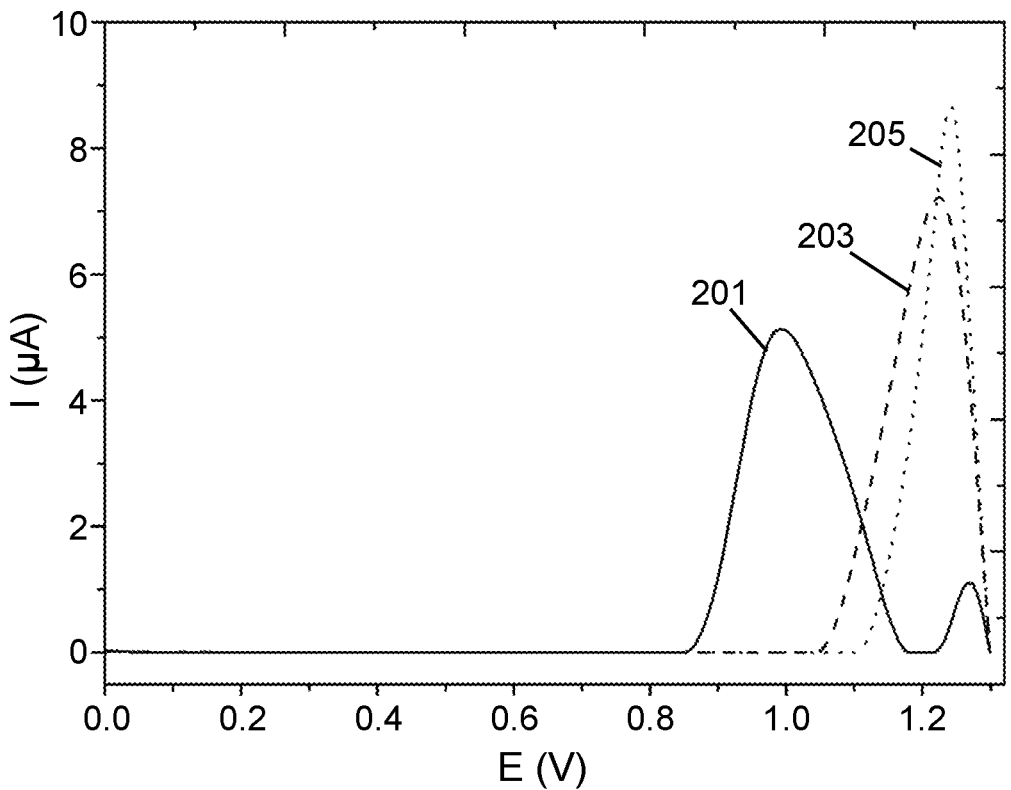

We now refer to FIG. 6. To understand the electrochemical behavior of cocaine and levamisole in mixtures, the pure compounds were firstly investigated by SWV at GSPE in PBS at pH 7 at a scan rate of 0.1 Vs$^{-1}$. It was observed that an oxidation peak appears for cocaine (201) at 1.04 V; attributed to the irreversible anodic oxidation of a tertiary amine group. Levamisole hydrochloride (203) gives rise to an oxidation peak at 1.24 V in PBS at pH 7. However, when a 1:1 equimolar mixture (205) of cocaine and levamisole was analyzed by SWV at pH 7, the peak of cocaine was suppressed. With levamisole being one of the most used adulterants in cocaine street samples, this poses difficulties in cocaine detection, leading to false negative results. The presence of levamisole also results in false positive results for cocaine colour test, leading to a colour change from pink to blue even in the absence of cocaine.

Figure 7:
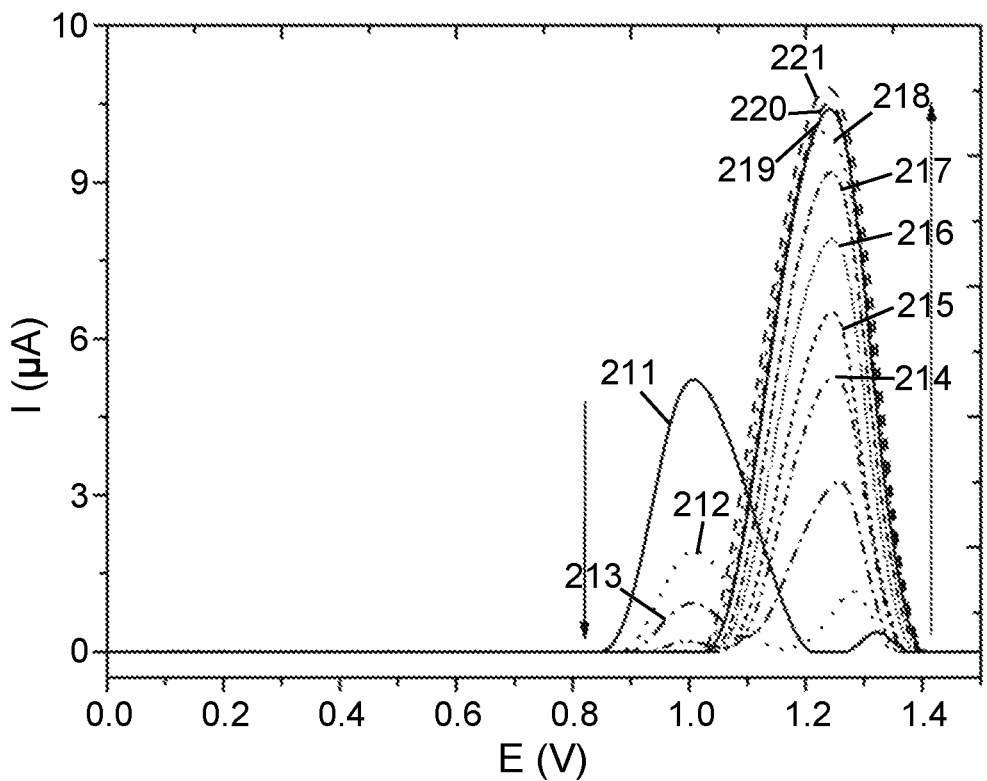

We now refer to FIG. 7. To investigate when the complete suppression of the cocaine peak appears, binary mixtures of cocaine-levamisole in different ratios were analyzed by SWV at a scan rate of 0.1 Vs$^{-1}$. The mixtures were obtained by mixing 1 mM cocaine solution with 1 mM levamisole solution in various volume ratios (% v/v): 100/0 (211), 90/10 (212), 80/20 (213), 70/30 (214), 60/40 (215), 50/50 (216), 40/60 (217), 30/70 (218), 20/80 (219), 10/90 (220), 0/100 (221). The arrows in FIG. 7 indicate the decrease and increase of the cocaine and levamisole peaks, respectively, for increasing levamisole concentration. The oxidation peak of cocaine decreased dramatically with an increasing levamisole concentration, demonstrating that the suppression effect by levamisole on the cocaine electro-oxidation signal is dependent on the cocaine-levamisole ratio. It could be observed that the oxidation peak of cocaine decreased down to 60:40 (% v/v) ratio and was completely suppressed at 50:50 (% v/v) ratio in freshly prepared solutions. At first observation, the chemical integrity of each compound was not affected in the mixture, because, besides the change of the intensity of the peaks, the peak potential did not change significantly.

Figure 8:
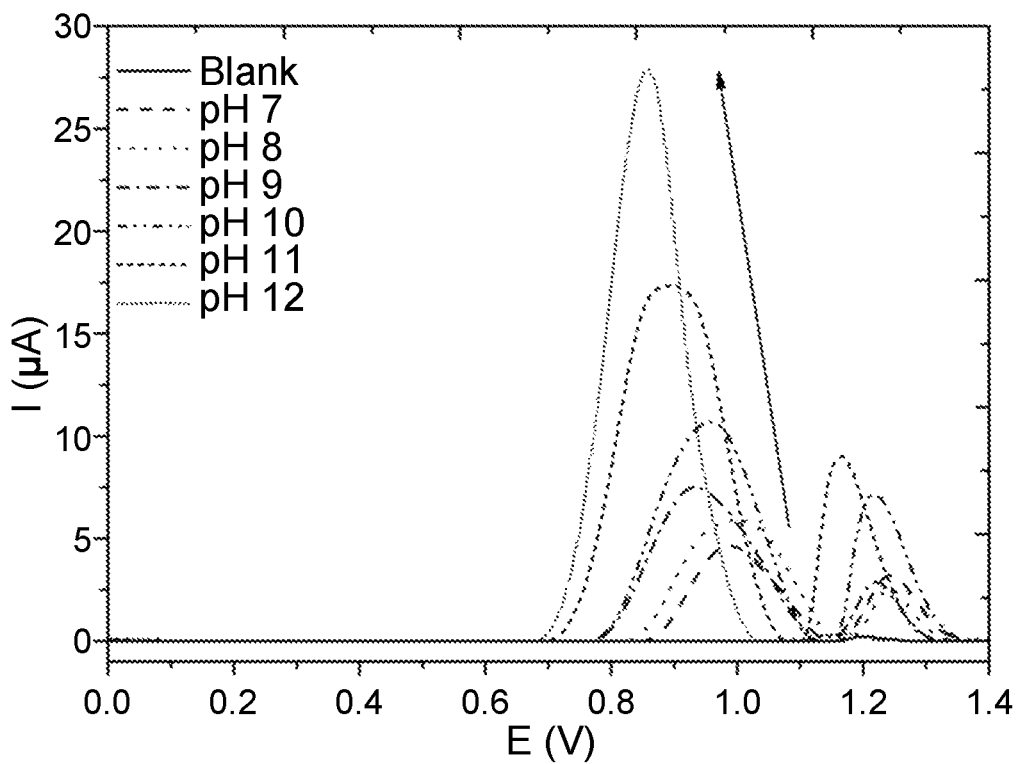

Example 2b: Influence of pH on the Electrochemical Analysis of Cocaine-Levamisole Binary Mixtures We now refer to FIG. 8 The electrochemical behaviour of 1 mM cocaine hydrochloride in the pH range 7-12 was investigated and a six-fold increase in the peak current together with a peak potential negative shift of around 200 mV was observed, as the pH increases from 7 to 12; this effect is indicated by the arrow in FIG. 8. The peak around 1.2 V was attributed to the substrate (GSPE) as it was also observed in the background (i.e. the blank).

Figure 9:
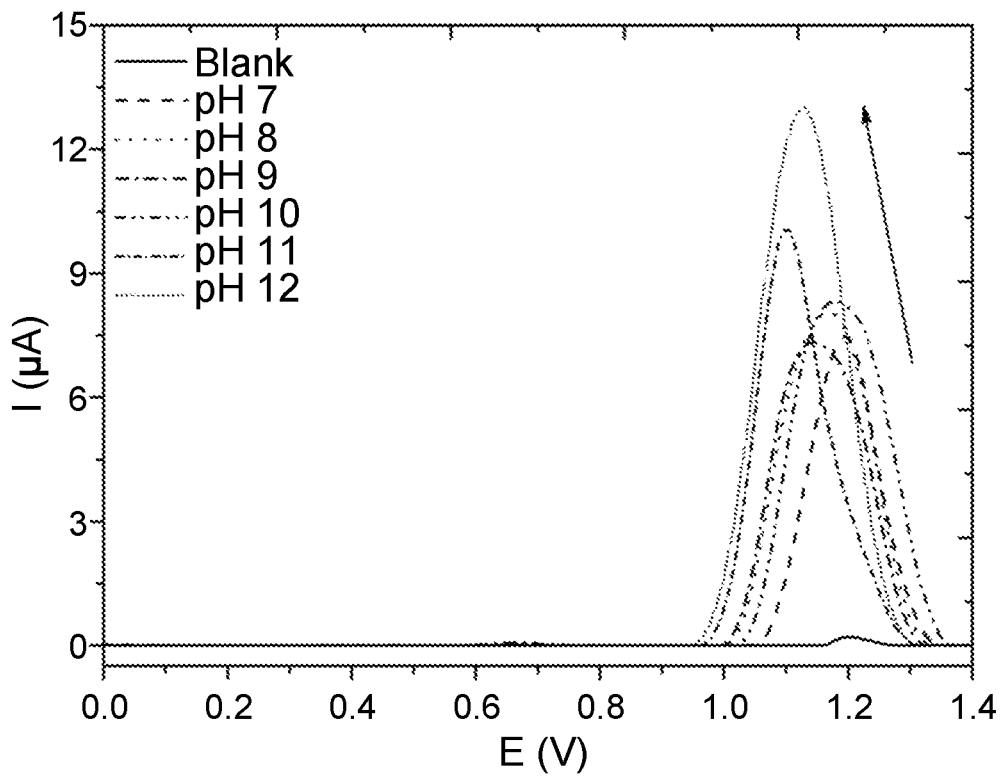

We now refer to FIG. 9. A similar behaviour was observed for 1 mM levamisole when the pH of the supporting electrolyte was increased from 12, with a two-fold increase in the peak current intensity as the pH varied from 7 to 12, together with a shift of potential to less positive values of around 70 mV; this effect is again indicated in FIG. 9 by the arrow. The pH increase from 7 to 10 resulted only in a small increase in the peak current intensity (7.7 to 9.3 µA), while the peak potential did not significantly change (1.19 to 1.17 V). A further pH increase to 11 and 12 lead to higher signals (11.4 to 14.8 µA, respectively) at lower potentials (1.12 V).

Figure 10:
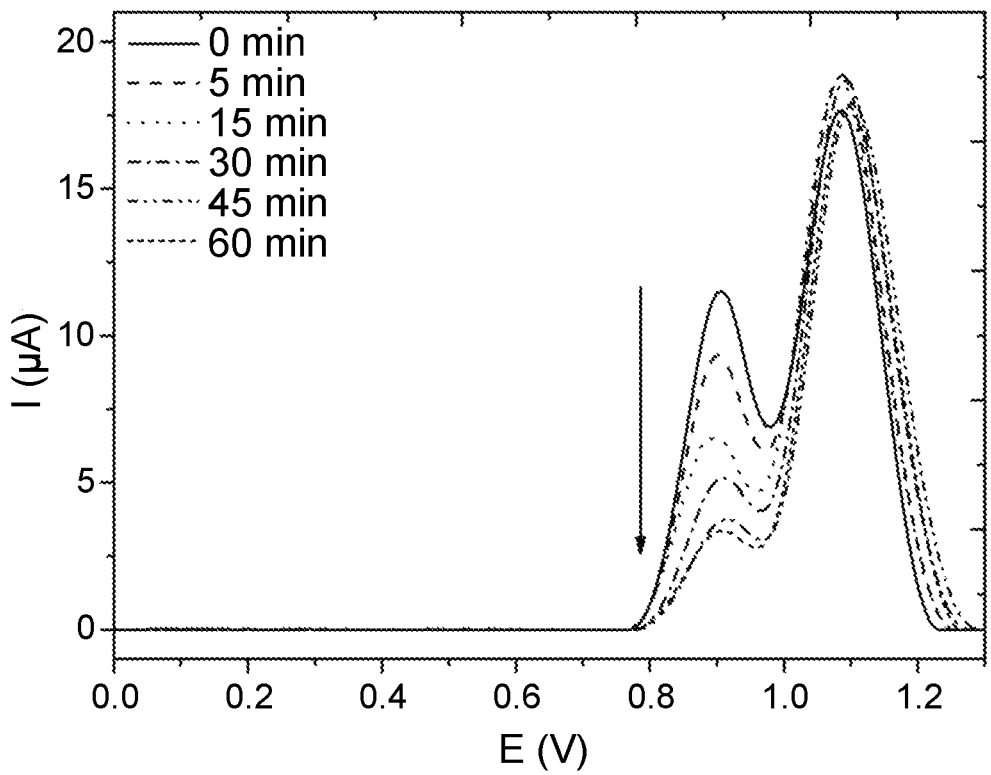

We now refer to FIG. 10. Since both cocaine and levamisole present a higher signal at lower potential values at pH 12, equimolar mixtures of cocaine and levamisole (1 mM) were analyzed by SWV at GSPE at pH 12 at different times (ranging from 0 to 60 min.). The oxidation signals of both cocaine and levamisole can be distinguished at pH 12, thus enabling the simultaneous detection of cocaine and levamisole in street samples. However, a decrease over time of the cocaine signal in the mixture was observed (indicated by the arrow in FIG. 10), suggesting possible stability issues at pH 12. The oxidation signal of levamisole in the mixture was stable over the investigated time frame. Stability studies on the pure compounds were further carried out at pH 12 (not shown) and compared to their stability at pH 7; to find the best conditions for handling and analyzing the street samples, e.g. in case of on-site measurements.

Figure 11:
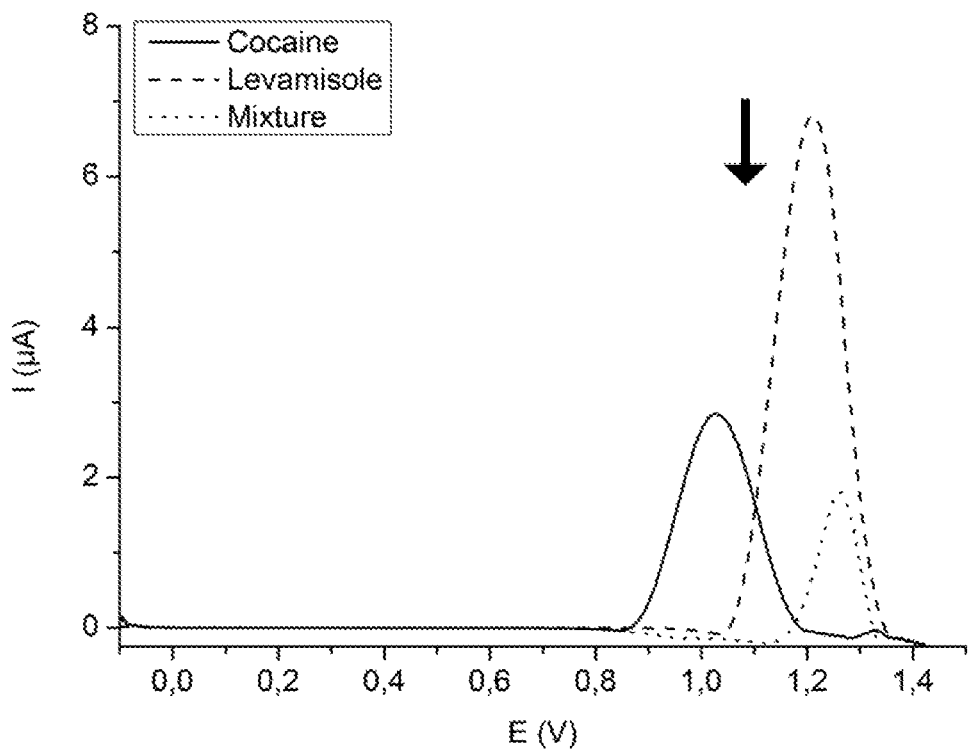
Figure 12:
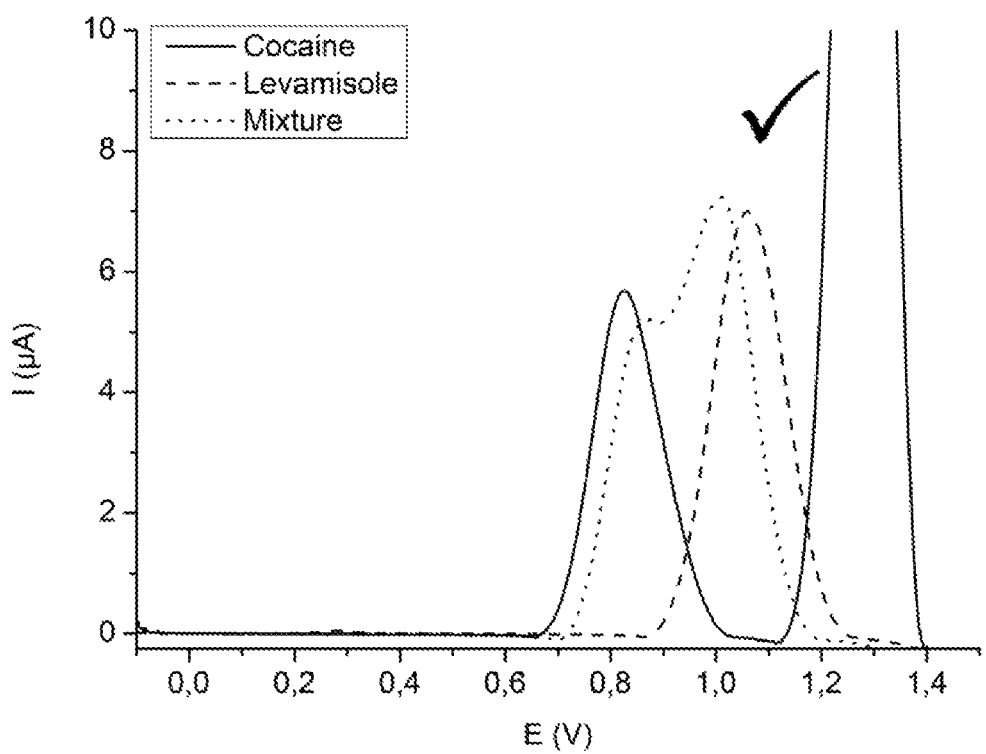

We now refer to FIGS. 11 and 12, showing the double scan electrochemical signal of cocaine, levamisole and their 1:1 mixture at pH 7 and pH 12, respectively. These figures show that there was a complete suppression (schematically marked by the downward arrow in FIG. 11) of the cocaine signal in the pH 7 situation while in the mixture (dotted line). Detection of cocaine was therefore not possible for pH 7. The pH 12 strategy does show the signal of cocaine, leading to detection (schematically marked by the checkmark in FIG. 12).

Figure 13:
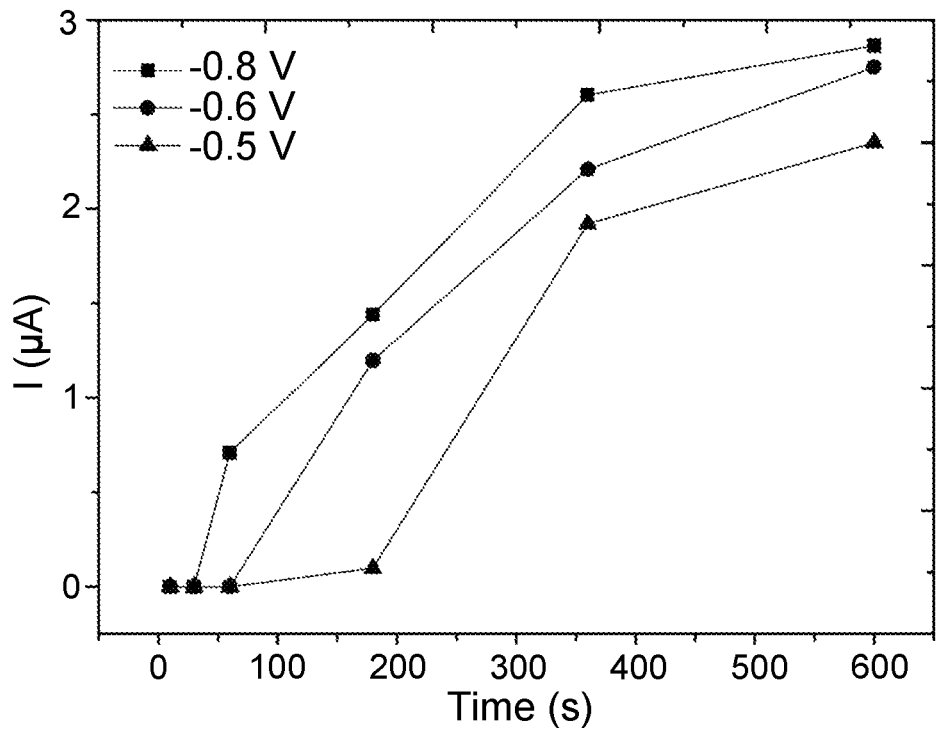
FIGS. 13, 21 and 37 is a graph of the obtained voltammetric current in function of the pretreatment period for different pretreatment potentials, in accordance with exemplary embodiments of the present invention.

Example 2c: Influence of Electrochemical Pretreatment of the Electrode Surface on the Analysis of Cocaine-Levamisole Binary Mixtures We now refer to FIG. 13. The effect of a cathodic surface pretreatment on the cocaine detection in the presence of levamisole was evaluated, by applying various potentials for a fixed time. The potential was investigated for −0.8 V, −0.6 V, −0.5 V, −0.4 V (not shown), −0.2 V (not shown), while the pretreatment duration (time) was varied from 10 to 600 s. For these potentials, it was observed that when a conditioning potential is applied for 10 s and 30 s, the presence of cocaine cannot be detected in a 1:1 binary mixture. However, as the conditioning time was further increased, a peak for cocaine starts to appear. The peak of cocaine in the mixture increased both as the time increased and as the potential shifted to less negative values. It was observed that for a conditioning potential of −0.8 V, the peak of cocaine arose after 60 s and further increased as the time was increased to 360 s, then tended to level. For a conditioning potential of −0.6 V, the peak of cocaine was only visible after 180 s, while for a potential of −0.5 V, the conditioning time needed for the cocaine peak to arise was 360 s. When a potential of −0.4 V was applied, only a small or no peak for cocaine appeared after 600 s of pretreatment, while for −0.2 V, the peak of cocaine was not visible. Since high values for the current were obtained for a potential of −0.8 V and time of 360 s, these were considered as the optimal parameters and were used for further experiments.

Figure 14:
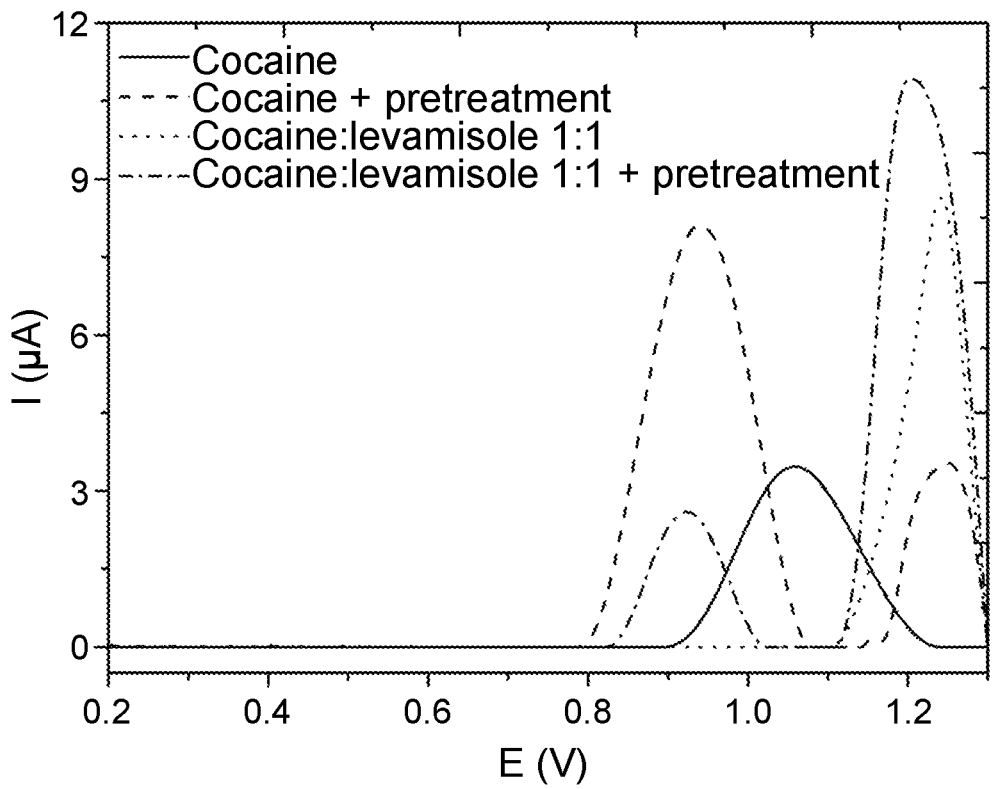

We now refer to FIG. 14, showing the electrochemical signal of 1 mM cocaine and cocaine-levamisole 1:1 mixture at pH 7 on GSPE without and with electrochemical pretreatment (conditioning potential of −0.8 V for 360 s); illustrating the effect of cathodic pretreatment on the oxidation peak of cocaine at pH 7. An enhancement in the intensity of the cocaine oxidation signal together with a shift to less positive potentials was observed, showing the electrocatalytic effect of the pretreatment on the cocaine oxidation at GSPE at pH 7. Moreover, after the potentiostatic cathodic pretreatment on cocaine-levamisole 1:1 binary mixtures, the signal of cocaine could be unravelled, with a good peak-to-peak separation, thus enabling a simultaneous detection of cocaine and levamisole in binary mixtures.

Example 2d: Calibration Curves for Cocaine in the Presence of Levamisole at pH 12 and at pH 7 with a Pretreatment Step Calibration curves for cocaine in the presence of levamisole, in equimolar concentrations, were obtained by SWV combining both aforementioned strategies, i.e. both measuring at both pH 7, with a pretreatment step, and at pH 12.

SWV curves recorded at bare GSPE with increasing concentrations of cocaine and levamisole at pH 12, in 1:1 ratios, showed that the peak current of cocaine increased linearly with increasing concentrations of cocaine in the range of 10-2500 µM. The obtained calibration curve was defined by the equation $y=0.011x-0.349$, $R2=0.995$. The limit of detection based on the minimum distinguishable signal for lower concentrations of analyte was 5 µM with a relative standard deviation (RSD) of 2.5% (n=5).

SWV curves of different concentrations of cocaine in the presence of levamisole (1:1 molar ratio) under the optimized pretreatment conditions at pH 7 were also recorded. The oxidation peak currents of cocaine were found to be linear with the logarithm of the concentration over the range from 10-5000 µM. The equation obtained in this case for the calibration curve for cocaine was $y=1.798x-1.116$, $R^2=0.991$. The lowest concentration that could be experimentally detected using the pretreatment strategy at pH 7 was 3 µM with an RSD of 3.1% (n=5).

Example 2e: Analysis of Cocaine in Real Samples

To assess the usefulness of the developed strategies for the determination of cocaine in the presence of levamisole, three street samples were further analyzed with the proposed methodologies and compared with those obtained by GC-MS. For this purpose, 1 mg street sample was dissolved in 10 mL PBS at pH 7 and pH 12, respectively, and the measurements were carried out as previously described, including the pretreatment step for pH 7. The quantification of cocaine was achieved by applying the standard addition method and the results are presented in the following table:

| Sample No | composition | GC-MS wt % | SWV pH 12 wt % | RSD % | SWV pH 7 wt % | RSD % |
|---|---|---|---|---|---|---|
| 5 | Cocaine | 70 | 78 | 3.7 | 76 | 3.0 |
|   | Levamisole | 23 |  |  |  |  |
| 23 | Cocaine | 57 | 61 | 6.4 | 62 | 1.2 |
|   | Levamisole | 41 |  |  |  |  |
| 24 | Cocaine | 55 | 59 | 5.7 | 58 | 4.6 |
|   | Levamisole | 42 |  |  |  |  |

The results demonstrate that the developed strategies enable the determination of cocaine in samples adulterated with levamisole and for example to provide a useful tool for selective on-site detection and quantification (within acceptable tolerances) of cocaine in street samples.

Figure 15:
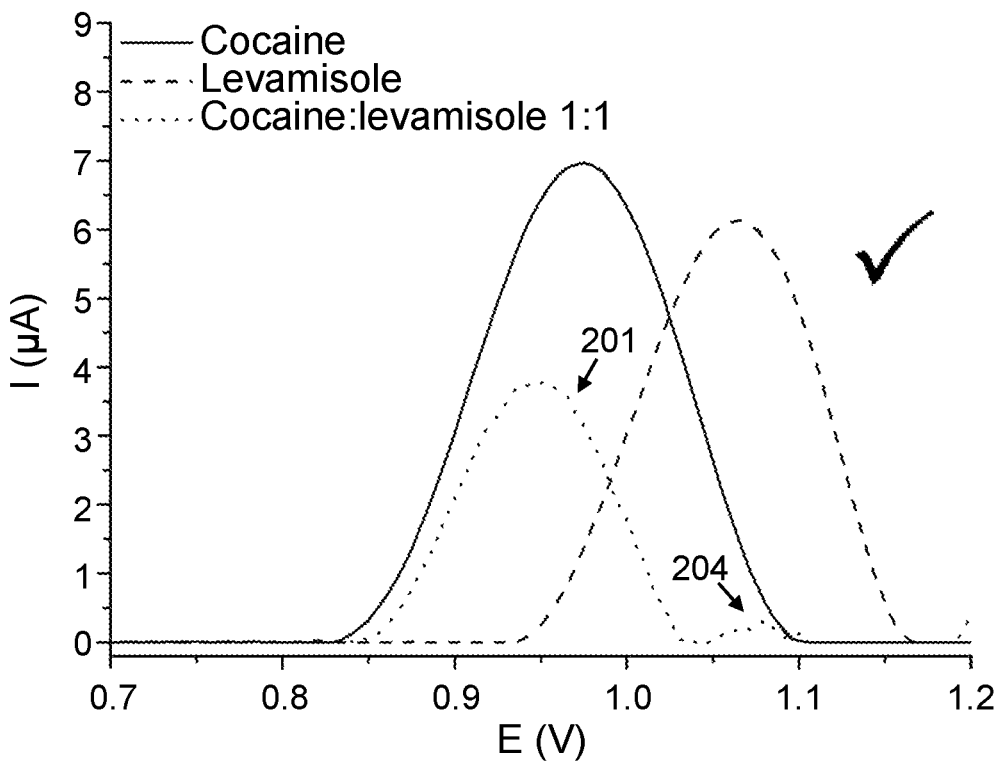

Example 2f. Influence of Chemical Modification of the Electrode Surface on the Analysis of Cocaine-Levamisole Binary Mixtures We now refer to FIG. 15. Yet a further strategy for resolving the cocaine and levamisole peaks involves the chemical modification of the electrode. To this end, the GSPE electrodes were electrochemically coated with a poly (p-aminobenzoic acid) (PABA) film. FIG. 15 shows the results obtained by SWV using the PABA coated GSPE electrode in PBS at pH 7 for pure 0.5 nM cocaine and levamisole 0.5 nM solutions and for their 1:1 equimolar cocaine-levamisole mixture. Compared to the results obtained with bare GSPE (FIG. 6), the oxidation peaks of both pure cocaine and pure levamisole are slightly negatively shifted; this was tentatively attributed to an accelerated oxidation of the two compounds, through good conductive properties and catalytic capability of the PABA film. For the 1:1 equimolar mixture, a suppression of the levamisole peak (203) is observed, greatly facilitating the detection of the cocaine peak (201). This effect was tentatively attributed to a preferential accumulation of cocaine at the PABA coated GSPE electrode, via H-bonds and physical adsorption.

Figure 16:
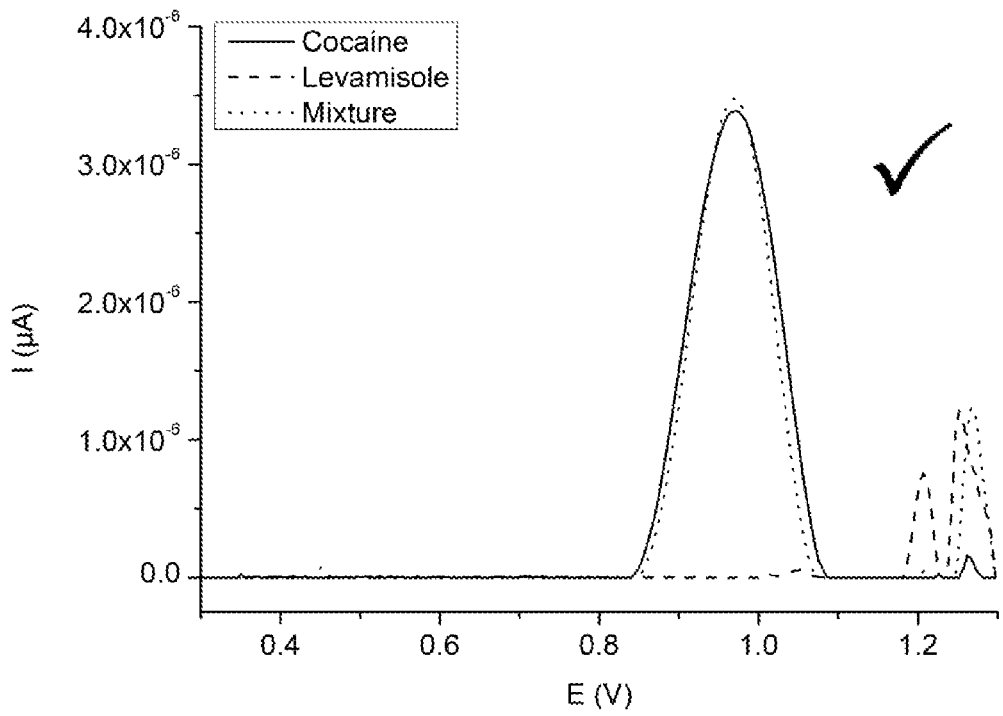

Similar experiments were performed with other polymeric coatings, including poly(o-aminobenzoic acid), poly (m-aminobenzoic acid) and poly(o-phenylenediamine) (POPD). For poly(o-phenylenediamine), and referring to FIG. 16 which shows the electrochemical signal of cocaine, benzocaine and their 1:1 mixture at pH 7 after coating the electrode with POPD, comparably good results were obtained as for PABA. For poly(m-aminobenzoic acid) (not depicted), the ability to resolve the cocaine and levamisole peaks appeared to be somewhat less than for PABA; furthermore, the results tended to be slightly less consistent and more reliant on the solute concentrations used. For poly(o-aminobenzoic acid) (not depicted), the ability to resolve the cocaine and levamisole peaks and the consistency of the results appeared to be further reduced; moreover, the poly (o-aminobenzoic acid) was easily dissolved in water. The above notwithstanding, both poly(m-aminobenzoic acid) and poly(o-phenylenediamine) coated GSPE electrodes can still offer an improvement over bare GSPE electrodes.

Example 3: Electrochemical Detection of Cocaine in the Presence of Other Interferents Similar experiments as shown in example 2 were performed using on the one hand cocaine an on the other hand benzocaine, bupivacaine, caffeine, chlorpromazine, codeine, dextromethorphan, diltiazem, diphenhydramine, heroin, hydroxyzine, lidocaine, paracetamol, phenacetine, procaine, promethazine or quinine.

For these experiments, a PBS buffer solution was used containing 100 mM KCl and 20 mM $KH_2PO_4$, of which the pH was adjusted according to the experiment to 7 or 12. All potential values were measured with reference to the internal reference electrode of the screen printed electrodes.

The experimental parameters used are summarized in the following table:

| Parameter | pH 7 | | pH 12 | | Pretreatment pH 7 | Pretreatment pH 12 | PABA pH 7 | POPD pH 7 |
|---|---|---|---|---|---|---|---|---|
|  | SS | DS | SS | DS |  |  |  |  |
| $E_{conditioning}$ (V) | 0 | 1.5 | 0 | 1.5 | $-0.8^\dagger$ | $-0.8^\dagger$ | 0 | 0 |
| $t_{conditioning}$ (s) | 5 | 5 | 5 | 5 | $360^\dagger$ | $360^\dagger$ | 5 | 5 |
| $E_{start}$ (V) | −0.1 | 1.5 | −0.1 | 1.5 | −0.1 | −0.1 | 0 | 0 |
| $E_{halfway}$ | / | −0.1 | / | −0.1 | / | / | / | / |
| $E_{end}$ (V) | 1.5 | 1.5 | 1.5 | 1.5 | 1.5 | 1.3 | 1.2* | 1.2* |
| Frequency (Hz) | 10 | 10 | 10 | 10 | 10 | 10 | 10 | 10 |
| Amplitude (V) | 0.025 | 0.025 | 0.025 | 0.025 | 0.025 | 0.025 | 0.025 | 0.025 |
| $E_{step}$ (V) | 0.005 | 0.005 | 0.005 | 0.005 | 0.005 | 0.005 | 0.005 | 0.005 |

*1.3 V for levamisole
$^\dagger$Preferred conditions, alterations were also tested: −0.4 V, −0.6 V, −1.2 V and 5 s, 10 s, 30 s, 60 s, 120 s, 180 s, 360 s
SS = single scan;
DS = double scan The results of these experiments, together with those of example 2, are consolidated in the tables below. On the left side, the main peak potentials of the different compounds measured in their respective pure solutions are listed. On the right side, the ability of the different approaches (i.e. single scan at pH 7 or 12, double scan at pH 7 or 12, electrochemical pretreatment at pH 7 or 12 or coating the electrode with PABA or POPD) to resolve, or not, the cocaine signal with respect to the interferent in 1:1 binary mixtures thereof is schematically marked. In summary, it was observed that for cocaine-interferent mixtures, good results for distinguishing cocaine from the adulterant were obtained from double scans performed at pH 12; as compared to double scans at pH 7 or single scans at pH 7 or 12 (see table). An exception to this rule of thumb was found for benzocaine, codeine, heroin and quinine, for which the cocaine signal could not be resolved using either of these relatively simple approaches.

pose a problem for cocaine detection, but since the signal for benzocaine was also visible at its typical potential, the combination of both peaks gave the knowledge to address

| Compound | Ep(V) pH 7 SS | Ep(V) pH 7 DS | Ep(V) pH 12 SS | Ep(V) pH 12 DS | Resolution? 7SS | 7DS | 12SS | 12DS | Pretreatment pH 7 | Pretreatment pH 12 | PABA pH 7 | POPD pH 7 |
|---|---|---|---|---|---|---|---|---|---|---|---|---|
| Cocaine | 1.04 | 1.04 | 0.83 | 0.83 | ✓ | ✓ | ✓ | ✓ | ✓ | ✓ | ✓ | ✓ |
| Benzocaine | 0.78 | 0.79 | 0.54 | 0.62 | ↓ | ✓ | ✓→ | ✓→ | ✓ | ✓ | ✓ | ✓ |
| Bupivacaine | 0.88 1.09 x | 0.95 1.12 x | 0.68 | 0.74 | ≈ | x | ≈ | ✓ | ✓ | ✓ | | |
| Caffeine | 1.34 | 1.33 | 1.29 | 1.30 | ✓ | ✓ | ✓ | ✓ | ✓ | ✓ | | |
| Chlorpromazine | 0.67 0.90 1.37 | 0.60 0.87 1.25 | 0.53 | 0.55 | ↓ | ↓ | ✓ | ✓ | ↓ | ✓ | ↓ | ↓ |
| Codeine | 0.88 1.05 x | 0.95 1.07 x | 0.81 1.03 x | 0.81 x | x | x | x | x | ✓ | x | x | ✓ |
| Dextromethorphan | 0.86 1.21 1.29 | 0.82 1.22 1.34 | 0.63 | 0.61 | ↓ | ↓ | ✓ | ✓ | ↓ | ✓→ | ↓ | ↓ |
| Diltiazem | 0.82 0.99 1.32 x | 0.87 1.37 | 0.75 1.03 | 0.67 1.01 | ↓ | ✓ | ✓ | ✓ | ↓ | ✓→ | x | x |
| Diphenhydramine | 0.88 | 0.86 | 0.67 0.93 | 0.68 0.90 x | ✓ | ✓ | ✓ | ✓ | ✓ | ✓ | | |
| Heroin | 0.85 | 0.90 | 0.19 0.88 x | 0.21 0.87 x | x | x | x | x | ✓ | ✓ | | |
| Hydroxyzine | 0.81 0.88 0.99 x | 0.82 0.97 | 0.74 0.86 x | 0.68 0.81 x | x↓ | ✓ | x | ✓ | ↓ | x | x | x |
| Levamisole | 1.18 | 1.21 | 1.11 | 1.06 | ↓ | ↓ | ✓ | ✓ | ✓ | ✓ | ✓ | ✓ |
| Lidocaine | 0.82 | 0.84 | 0.62 | 0.70 | ✓ | ✓ | ✓ | ✓ | x | ✓ | | |
| Paracetamol | 0.37 | 0.36 | 0.12 | 0.08 | ✓ | ✓ | ✓ | ✓ | ✓ | ✓ | | |
| Phenacetine | 0.76 | 0.75 0.33 (0.06) | 0.53 | 0.13 0.58 | ✓ | ✓ | ✓ | ✓ | ✓ | ✓ | | |
| Procaine | 0.89 | 0.88 | 0.68 | 0.62 | ↓ | ↓ | ✓→ | ✓ | ✓ | ✓ | ✓ | ✓ |
| Promethazine | 0.54 0.70 | 0.56 0.71 | 0.45 0.63 | 0.44 0.60 | ↓ | ↓ | ✓ | ✓ | ↓ | ✓ | ↓ | ↓ |
| Quinine | 1.05 x | 1.01 x | 0.85 x | 0.84 x | x | x | x | x | x | x | x | x |

≈ = overlap,
↓ = suppression,
≈ = partial overlap,
x↓ = overlap and suppression,
→ = shift,
✓ = detectable cocaine signal,
blank = no data Several of these measurements are discussed in more detail below. For convenience, the same schematic markers are added to the different figures showing the different measured electrochemical signals.

Example 3a: Electrochemical Detection of Cocaine in the Presence of Benzocaine

Figure 17:
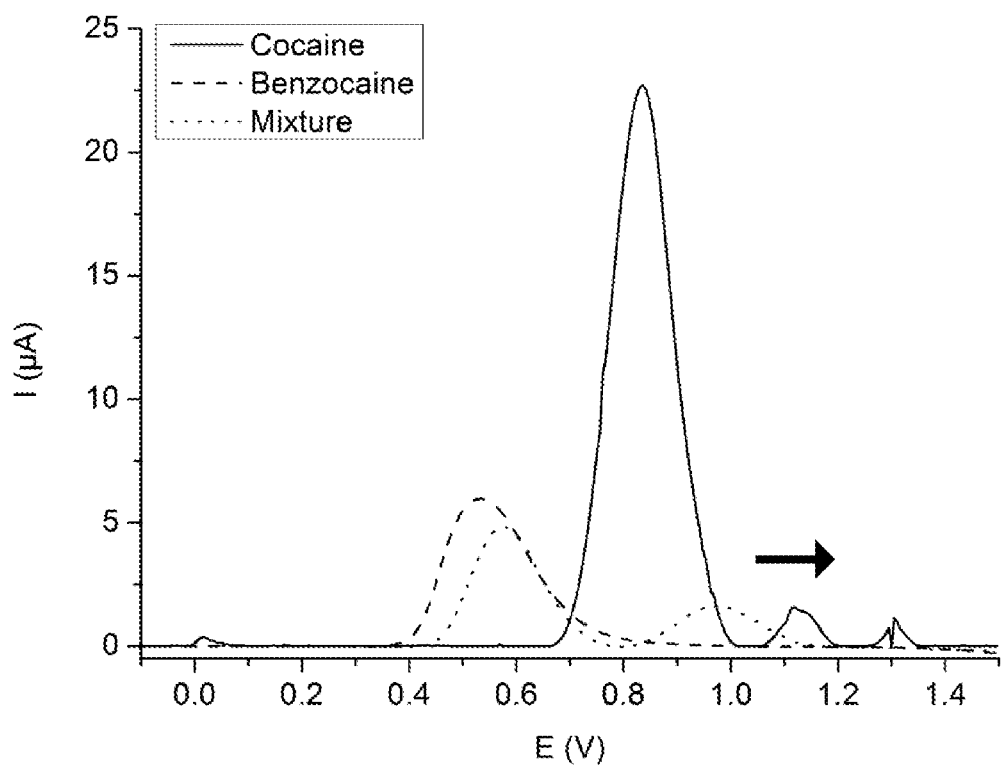
Figure 18:
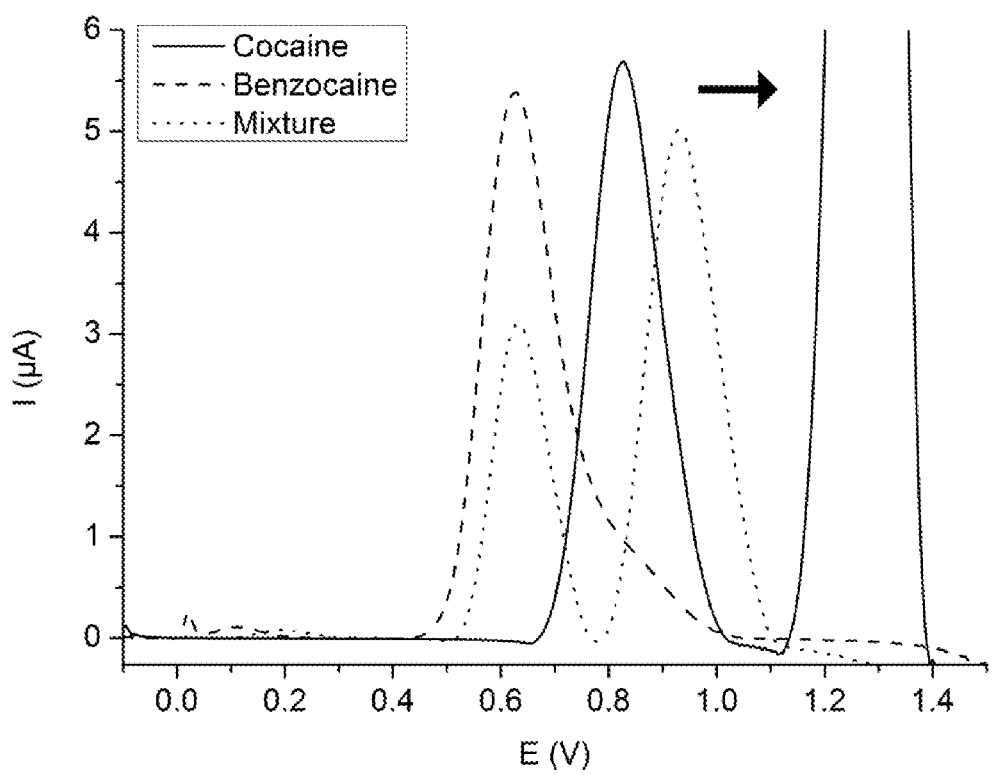

We now refer to FIGS. 17 and 18, showing the electrochemical signal, single scan and double scan respectively, of cocaine, benzocaine and their 1:1 mixture at pH 12. Focusing on the electrochemical fingerprint of cocaine and benzocaine, it is clear that in pH 12 conditions (both single and double scan) the signal for cocaine was detectable, but at a different potential. Usually, the cocaine signal is detectable at a potential of 0.83 V, while there was a shift noticeable when in mixture with benzocaine: the signal was now visible at 0.97 and 0.94 V for SS and DS, respectively. This might and compensate for this shift. However, it is more interesting to be able to make the identification based on the cocaine signal itself.

Figure 19:
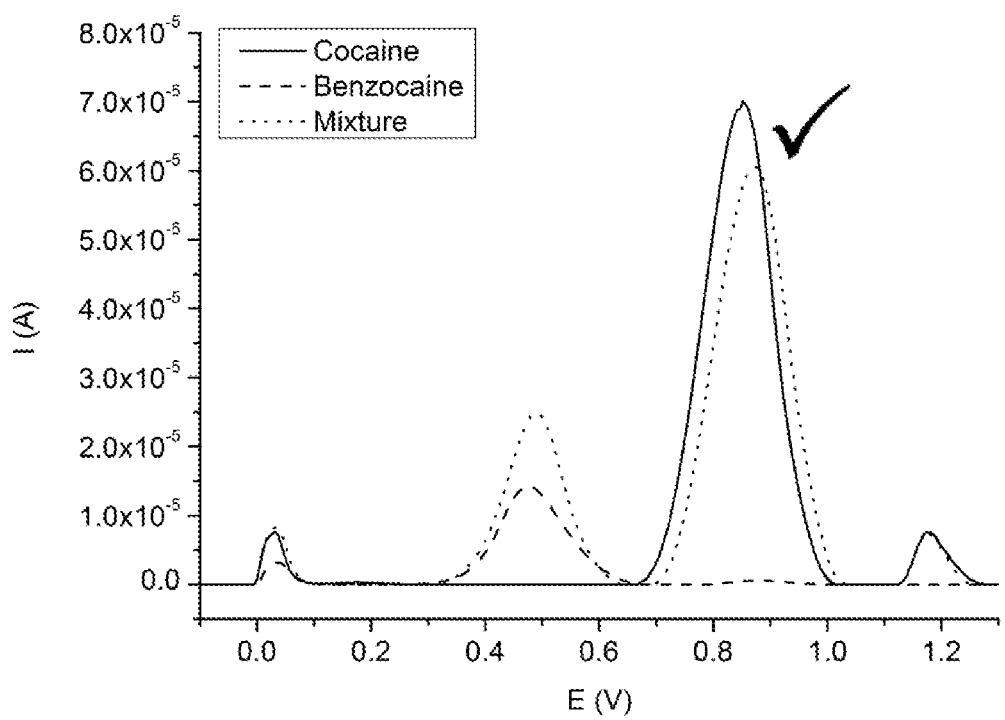

We now refer to FIG. 19, showing the electrochemical signal of cocaine, benzocaine and their 1:1 mixture at pH 12 after an electrochemical pretreatment. Implementing the pretreatment strategy with a potential of −0.8 V and time of 360 s seconds caused the signal of cocaine in the mixture to appear at the same potential as the pure cocaine signal. This takes into account the shift of the cocaine signal itself due to the pretreatment (see FIG. 20).

Figure 20:
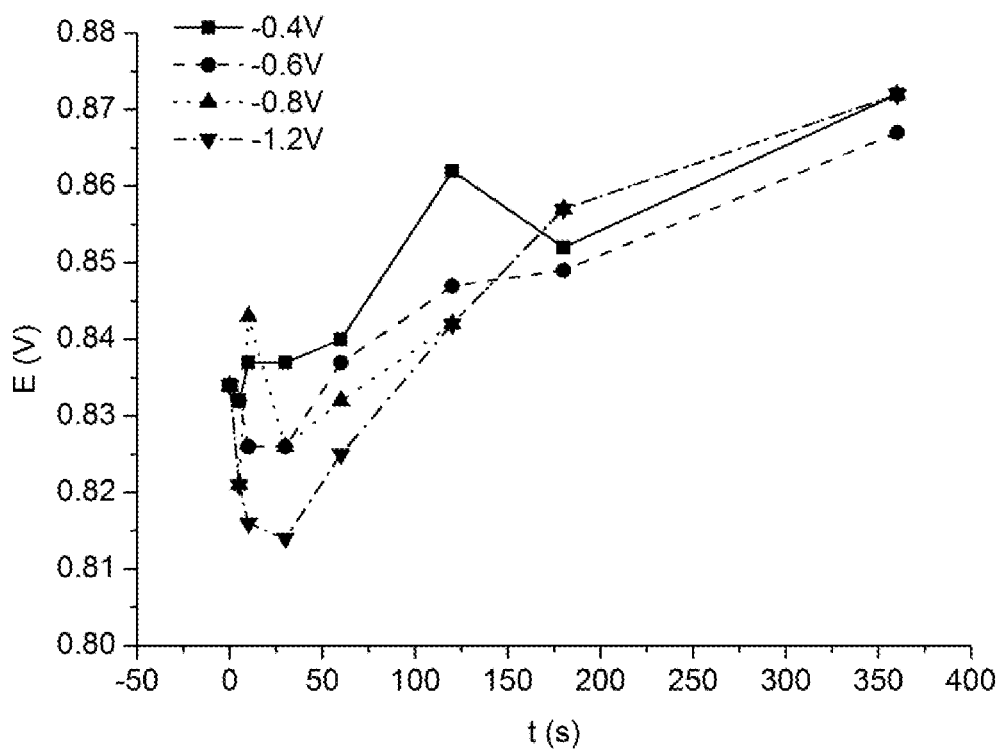
FIGS. 20 and 30 is a graph of the obtained cocaine peak potential in function of the pretreatment period for different pretreatment potentials, in accordance with exemplary embodiments of the present invention.
Figure 21:
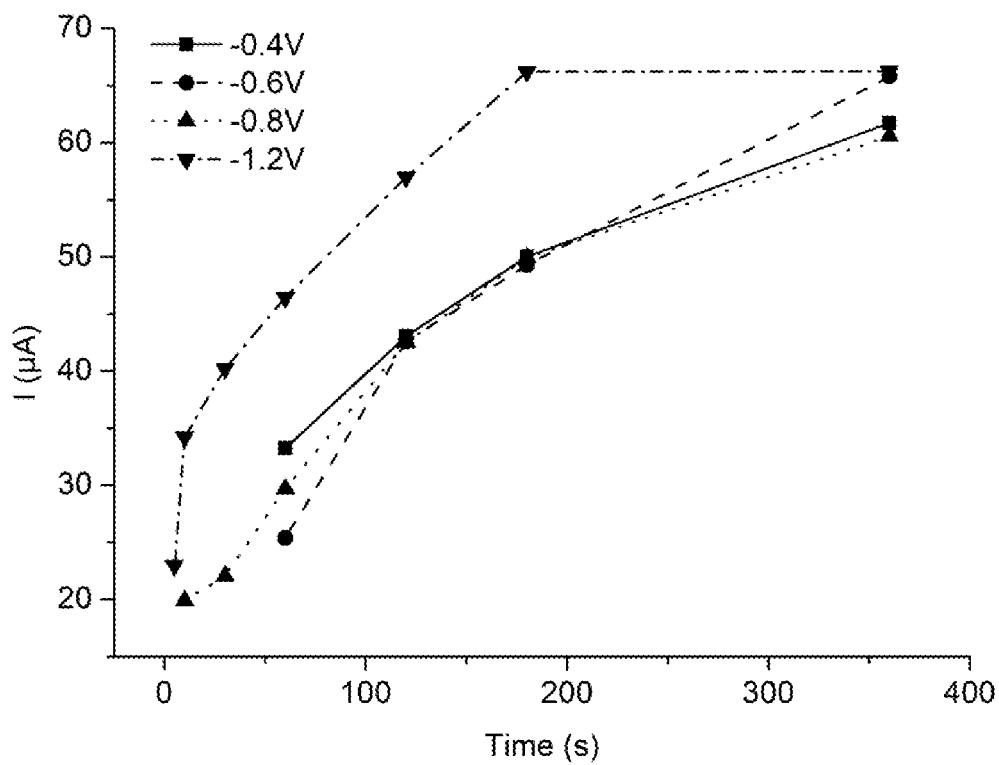

We now refer to FIGS. 20 and 21, respectively showing the obtained cocaine peak potential and cocaine-benzocaine voltammetric current in function of the pretreatment period for different pretreatment potentials at pH 7. The pretreatment was further optimized in order to determine which conditions are sufficient for the detection of the cocaine signal, without the potential shift. A boundary value of ±40 mV was set as a cut-off. If the signal in mixture differed more than 30 mV from the signal of pure cocaine in the same conditions, the signal was not linked to the presence of cocaine. FIG. 21 shows the cases where this shift was not prominent, i.e. was less than 40 mV. It can be noted that, while using −1.2 V as pretreatment potential, the shift of the cocaine signal was already less prominent after 5 seconds of pretreatment, resulting in a reliable detection of the cocaine signal, increasing the time further improves the situation. The same was valid for pretreatment with potential −0.8 V, but only from 10 seconds onwards. For both −0.6 V and −0.4 V, the cocaine signal was reliably detectable from 60 seconds onwards.

A similar result was obtained for pretreatment in pH 7 buffer (not shown), although there was no problem with a peak shift, only peak suppression in the pH 7 SS situation. The cocaine signal was detectable for a pretreatment in pH 7 with potential −0.6 V (from 180 s onwards), −0.8 V (from 60 s onwards) and −1.2 V (from 30 s onwards).

Figure 22:
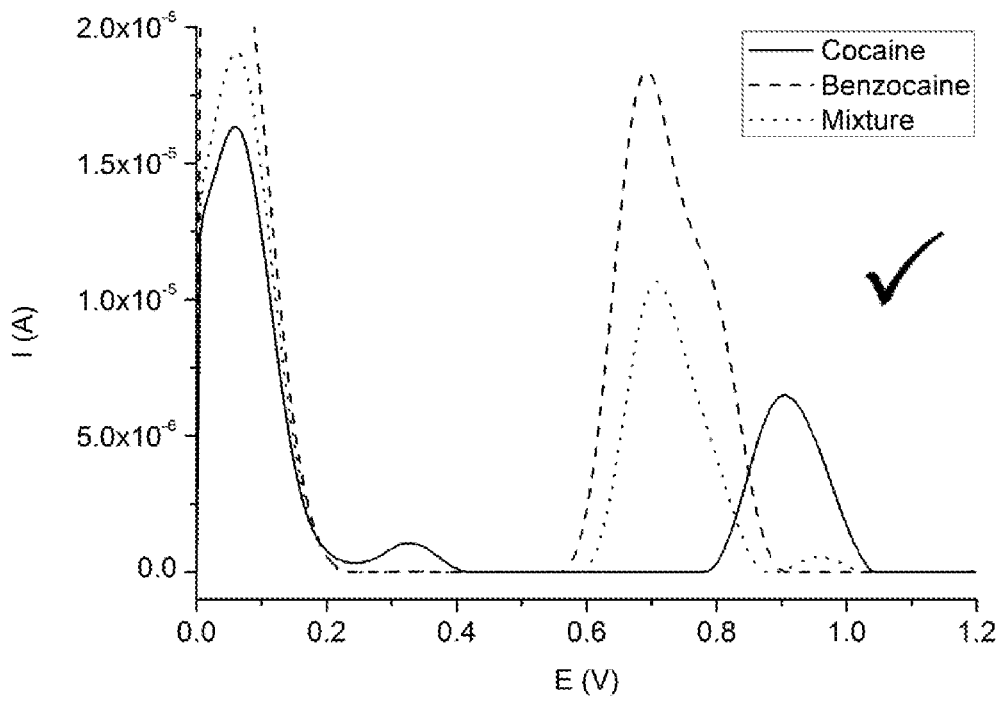

We now refer to FIG. 22, showing the electrochemical signal of cocaine, benzocaine and their 1:1 mixture at pH 7 after coating the electrode with PABA. The use of polymers might also improve the detectability of cocaine (in the presence of benzocaine). PABA was electropolymerized on graphene-SPE by CV (parameters: −0.5 to 1 V, 10 cycles, 50 mV/s; PABA solution 2.5 mM in PBS pH 7). The modified electrodes were incubated for 7 min with solutions of cocaine, interferent and cocaine+interferent in PBS pH 7 (1:1, 0.5 mM:0.5 mM), washed and subjected to SWV in PBS pH 7. The detection of cocaine proved possible in mixture with benzocaine (small signal at around 0.95 V). Furthermore, both compounds were detectable.

Figure 23:
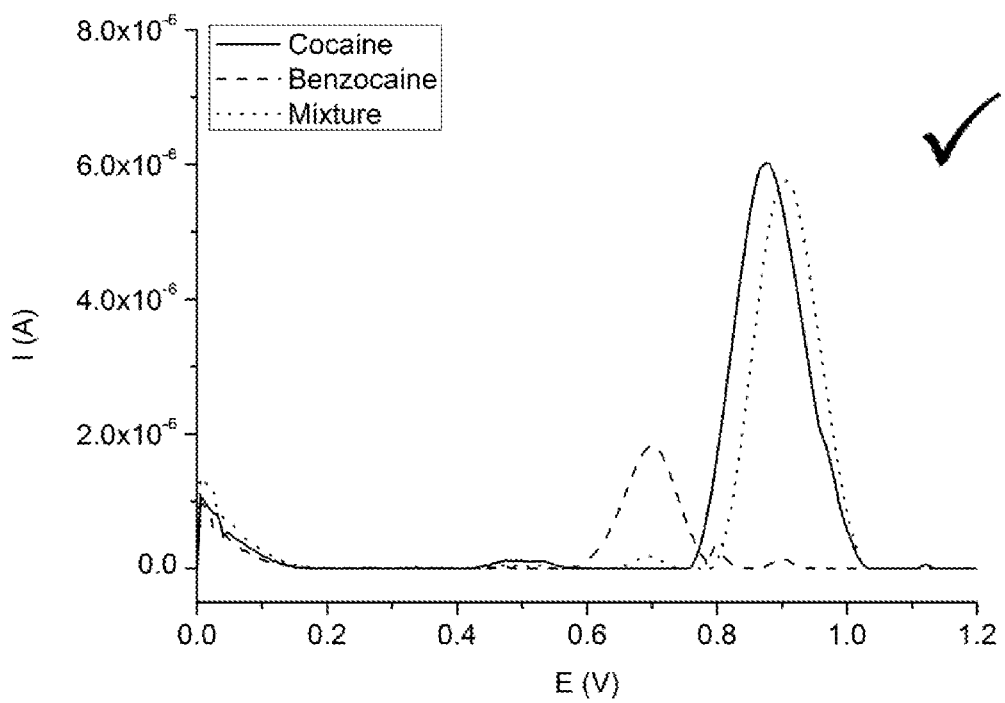

We now refer to FIG. 23, showing the electrochemical signal of cocaine, benzocaine and their 1:1 mixture at pH 7 using a bare electrode. As a comparison, similar experiments were performed at a bare graphene SPE electrode (in the absence of the polymer). Solutions of cocaine, benzocaine and 1:1 mixtures were incubated onto GPH SPE for 7 minutes, washed and SWV was performed in PBS pH 7. The peak of benzocaine was not visible in the mixture, though cocaine could be detected this time around. Thus, if the screening aims for simultaneous detection of cocaine and interferents, then the PABA or POPD modified SPE showed a better response than graphene as it revealed both the peaks of cocaine and of the adulterant. If we only aim for cocaine, GPH SPE showed only the peak of cocaine in mixtures.

Figure 24:
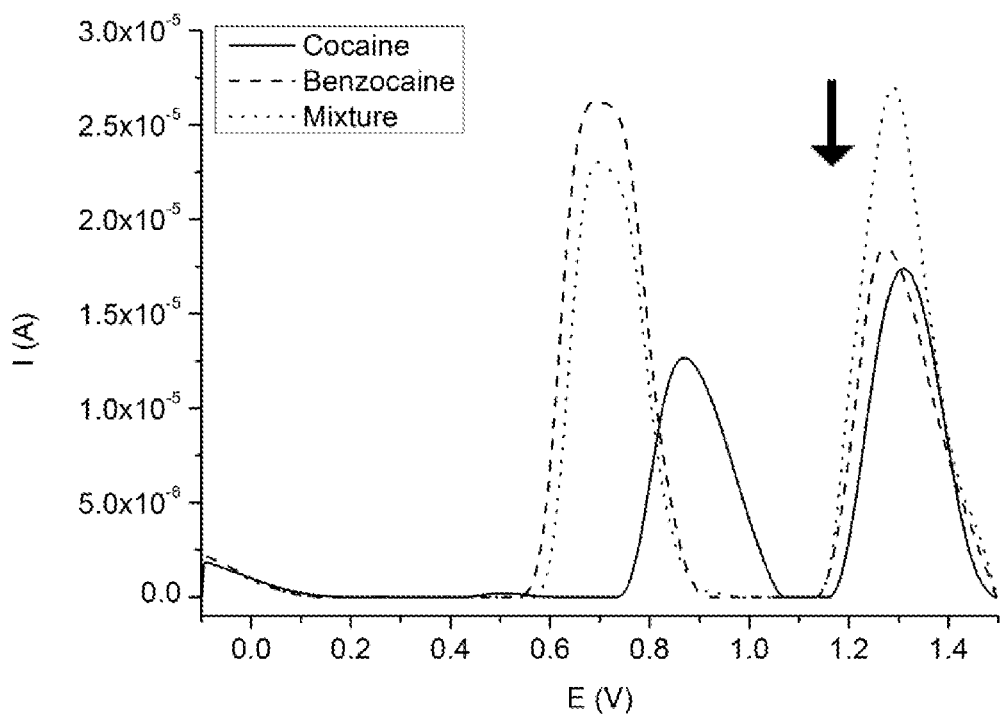

We now refer to FIG. 24, showing the electrochemical signal of cocaine, benzocaine and their 1:1 mixture at pH 7 using a bare electrode and without incubation. Experiments were also performed in a similar manner to above without incubation. Solutions of cocaine, benzocaine and 1:1 mixtures were put onto GPH SPE and immediately SWV was performed in PBS pH 7 and pH 12 (not shown). In contrast to the incubation method, the cocaine signal was suppressed in pH 7 buffer while in mixture with benzocaine.

Figure 25:
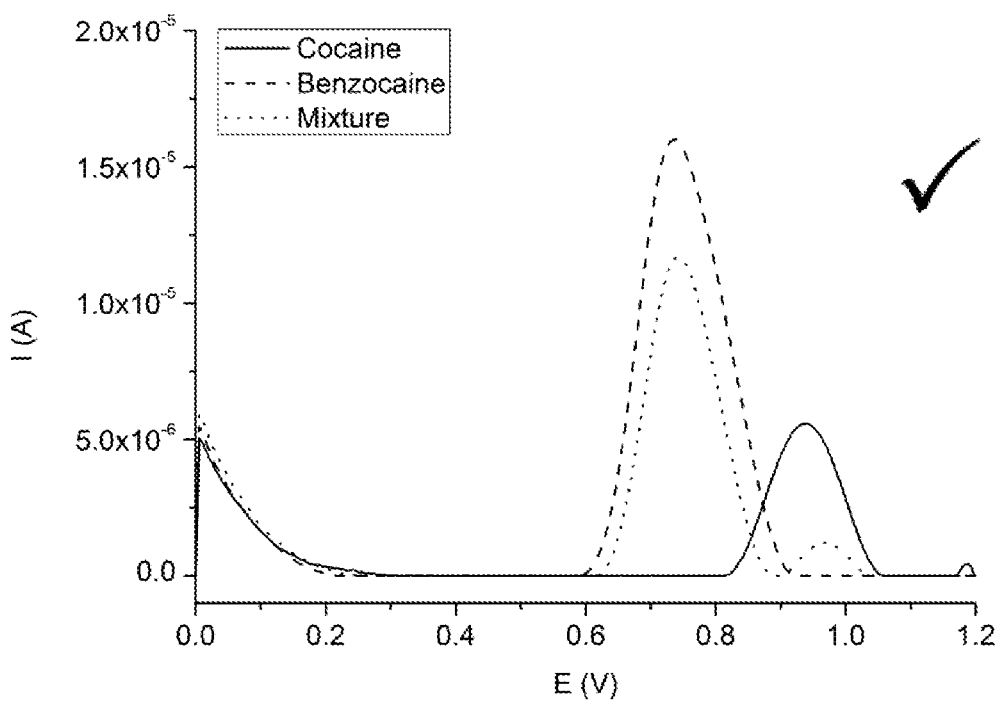

We now refer to FIG. 25, showing the electrochemical signal of cocaine, benzocaine and their 1:1 mixture at pH 7 after coating the electrode with POPD. o-Phenylenediamine (OPD) was electropolymerized on graphene-SPE by CV (parameters: −0.3 to 0.8V, 5 cycles, 50 mV/s; OPD solution 1 mM in acetate buffer pH 5.2 containing 0.1M KCl). The modified electrodes were incubated for 10 min with solutions of cocaine, interferent and cocaine+interferent in PBS pH 7 (1:1, 0.5 mM:0.5 mM), washed and subjected to SWV in PBS pH 7. The detection of cocaine in the mixture was possible (small signal at around 0.95 V).

Example 3b: Electrochemical Detection of Cocaine in the Presence of Codeine

Figure 26:
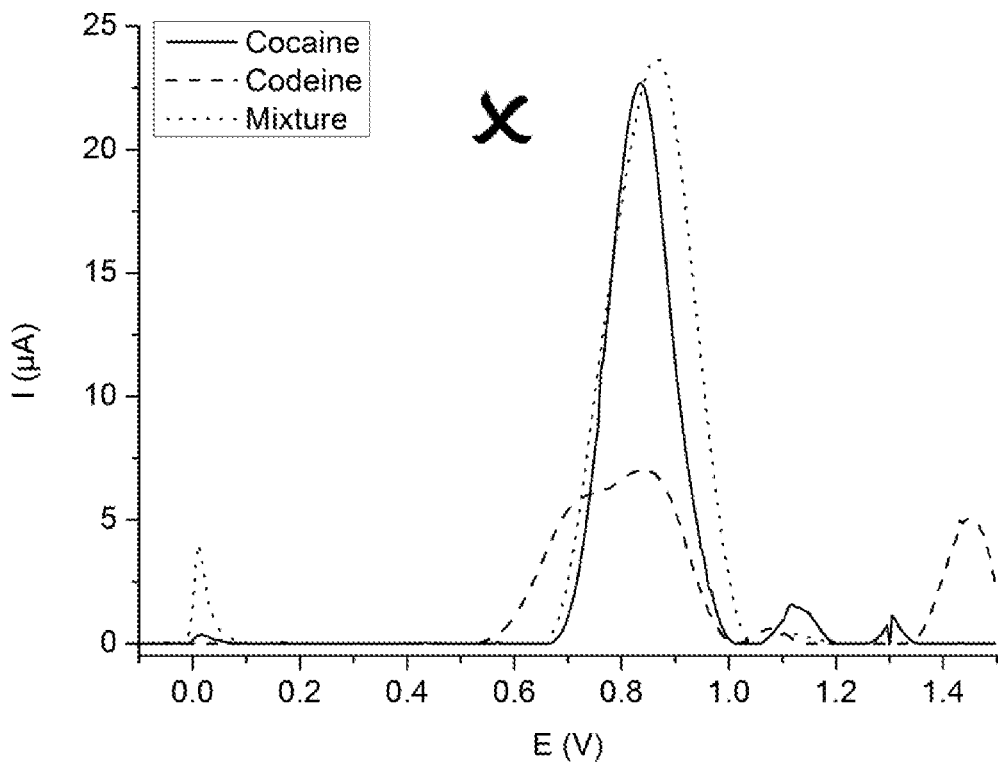
Figure 27:
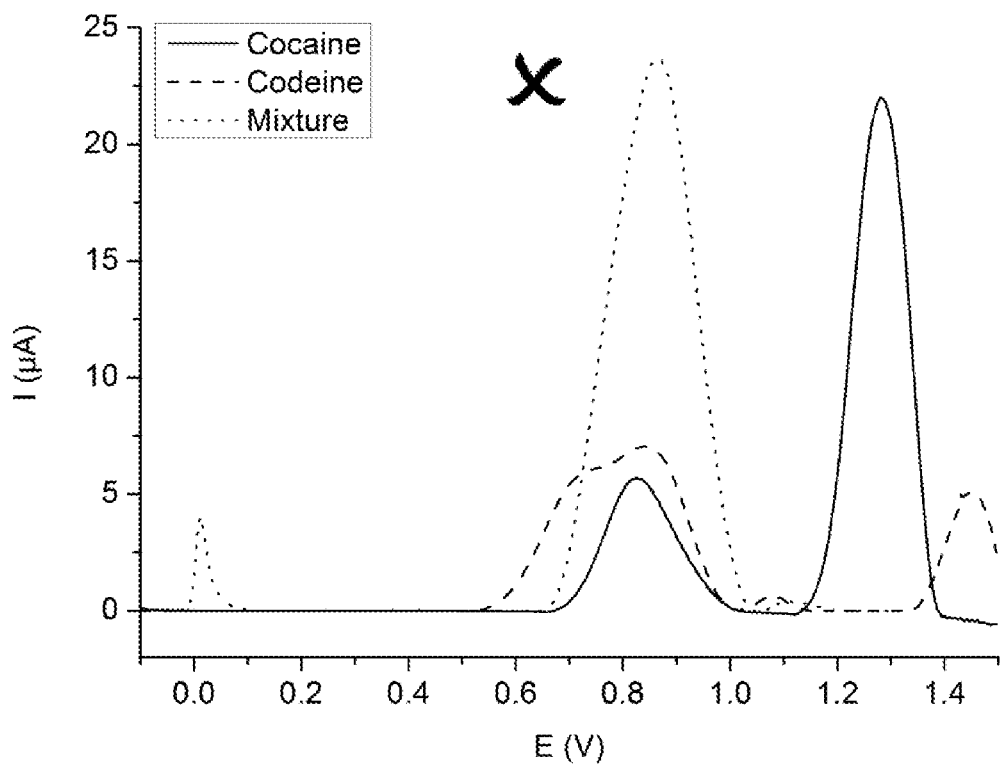

We now refer to FIGS. 26 and 27, showing the electrochemical signal, single scan and double scan respectively, of cocaine, codeine and their 1:1 mixture at pH 12. Focusing on the electrochemical fingerprint of cocaine and codeine, it is clear from FIGS. 26 and 27 that in pH 12 conditions (both single and double scan) the signal for cocaine was overlapping with the signal of codeine, as was the case in pH 7 (data not shown). This poses a problem for cocaine detection.

Figure 28:
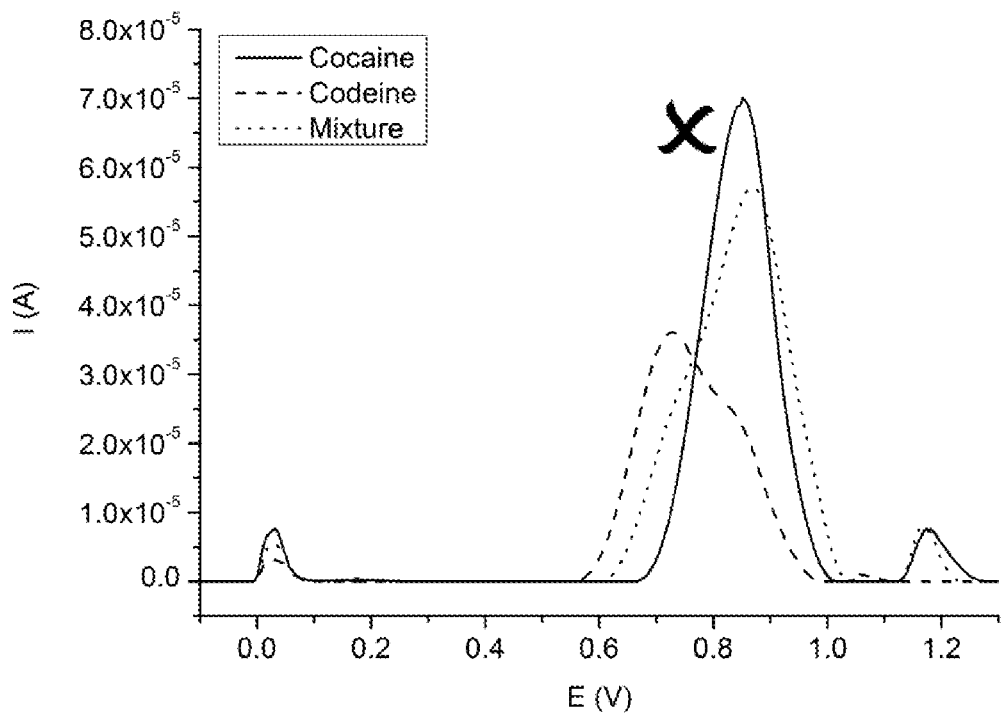

We now refer to FIG. 28, showing the electrochemical signal of cocaine, codeine and their 1:1 mixture at pH 12 after an electrochemical pretreatment. Implementing the pretreatment strategy (in pH 12) with a potential of −0.8V and time of 360 s seconds did not cause the signal of cocaine in the mixture to appear separated from the codeine signal. One can however contemplate using the relative intensity of the two shoulders appearing in the pure codeine signal (dashed line) and in the mixture signal (dotted line), with the intensity ratios clearly differing for both cases. Changing the conditions to harsher potentials or times did not bring a further improvement in pH 12.

Figure 29:
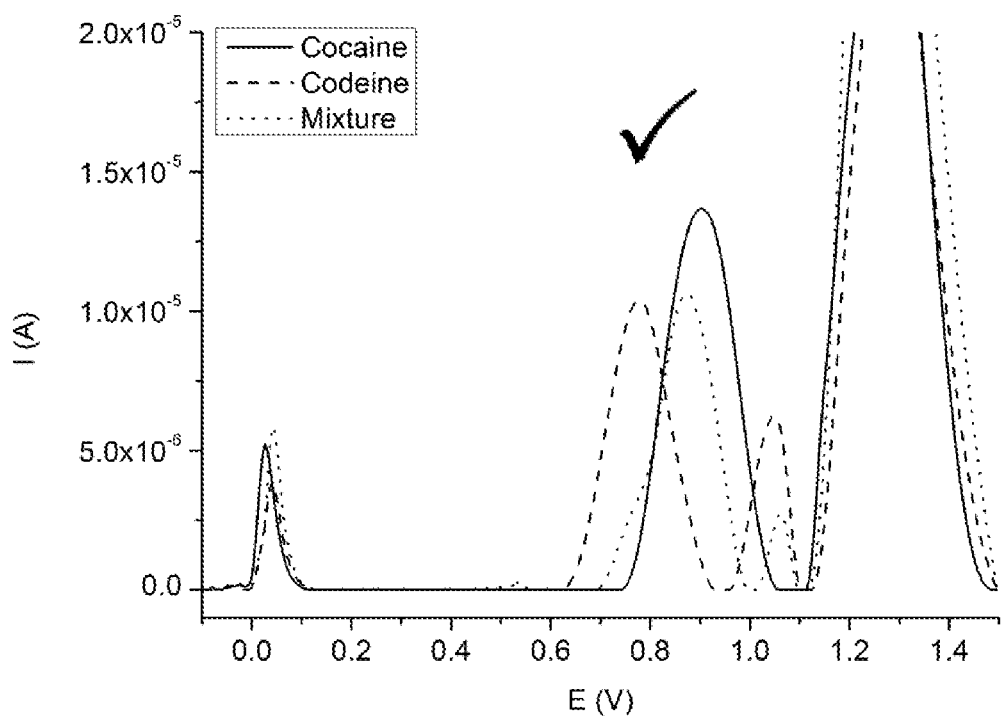
Figure 30:
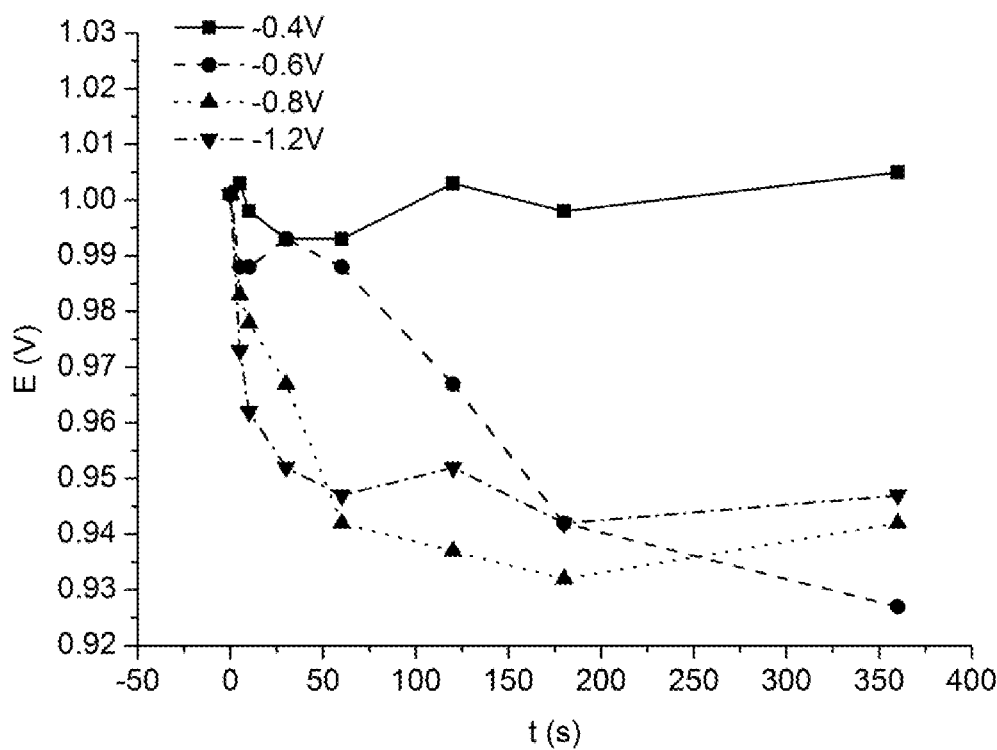

We now refer to FIG. 29, showing the electrochemical signal of cocaine, codeine and their 1:1 mixture at pH 7 after an electrochemical pretreatment. However, pretreatment in pH 7 did solve the problem using −0.8V and 360 s, whereas other tested pretreatment conditions (potentials and times) did not. FIG. 29 shows the signal of cocaine clearly appearing in the mixture (dotted line), in agreement with the signal of pure cocaine (solid line). The two signals of codeine (dashed line) were also visible in the mixture (dotted line), although the first signal was only slightly noticeable as a shoulder. It has to be noticed that the cocaine signal itself also shifts in pH 7 because of the pretreatment. The effect on the peak potential of cocaine is displayed in FIG. 30, showing the obtained cocaine peak potential in function of the pretreatment period for different pretreatment potentials at pH 7.

Figure 31:
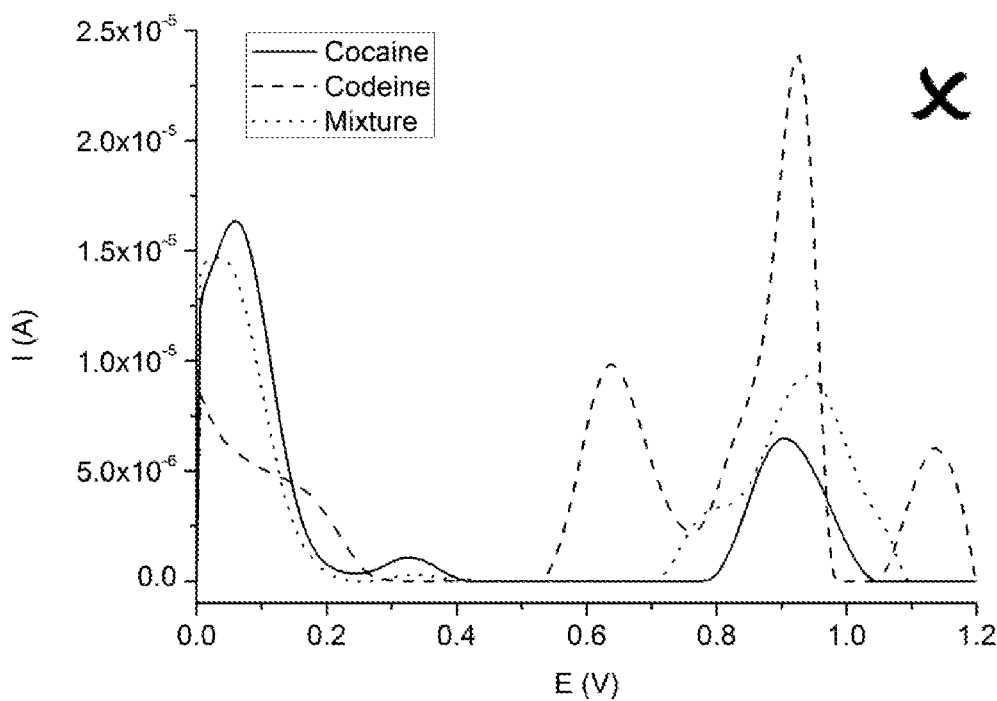
Figure 32:
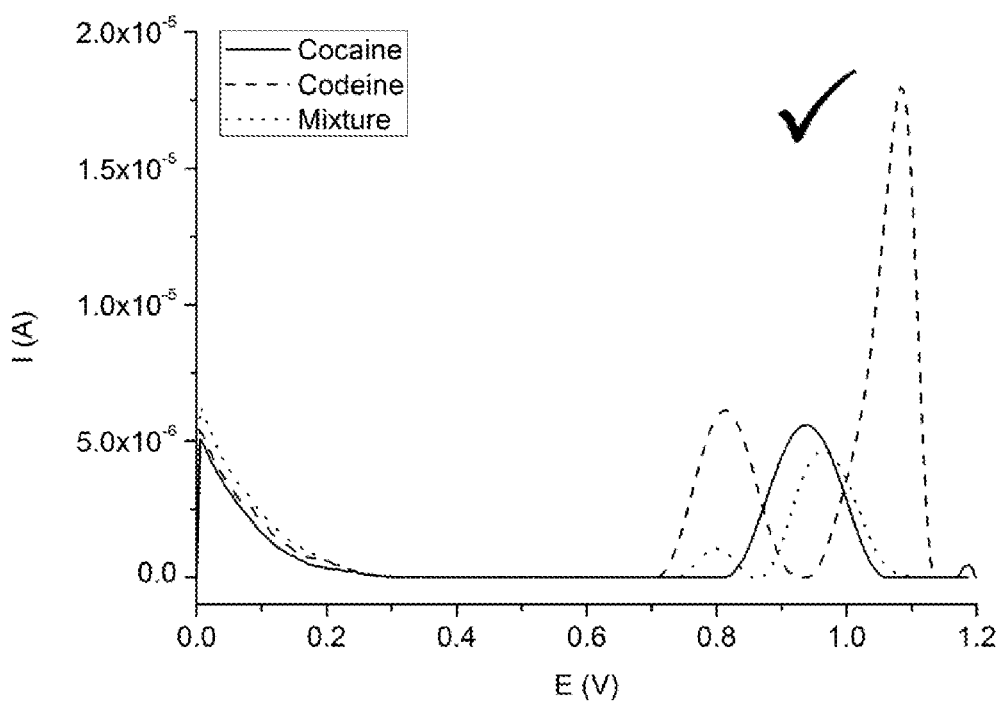

We now refer to FIGS. 31 and 32, showing the electrochemical signal of cocaine, codeine and their 1:1 mixture at pH 7 after coating the electrode with respectively PABA and POPD. POPD allowed a simultaneous detection of cocaine and codeine, while PABA modification did not.

Example 3c: Electrochemical Detection of Cocaine in the Presence of Heroin

Figure 33:
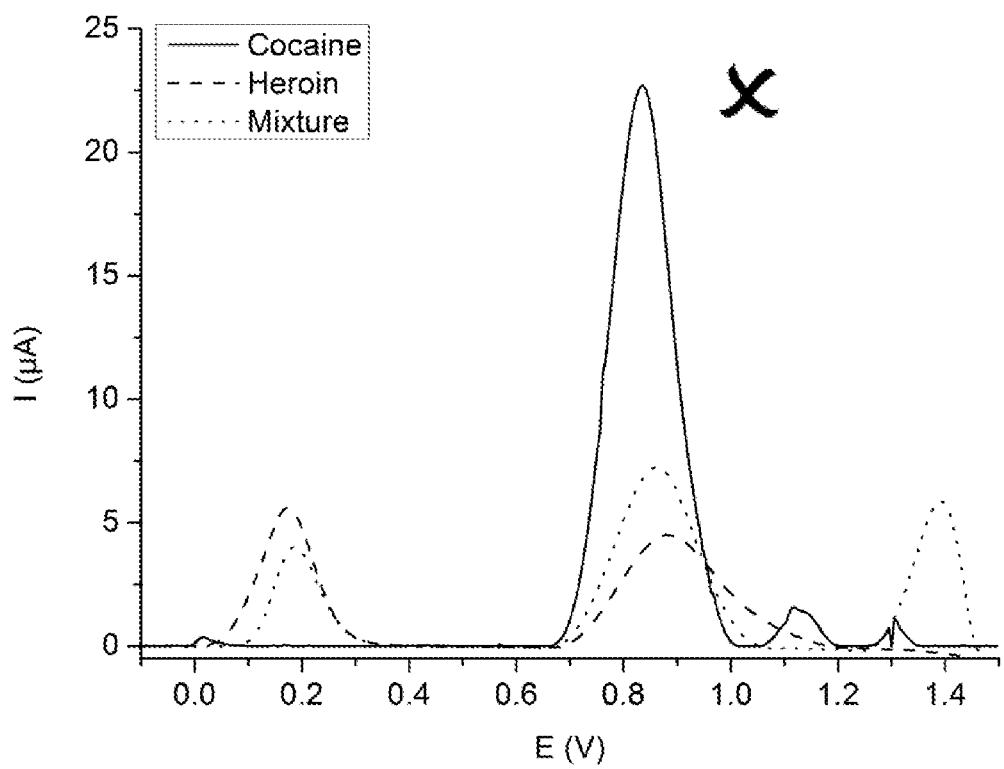
Figure 34:
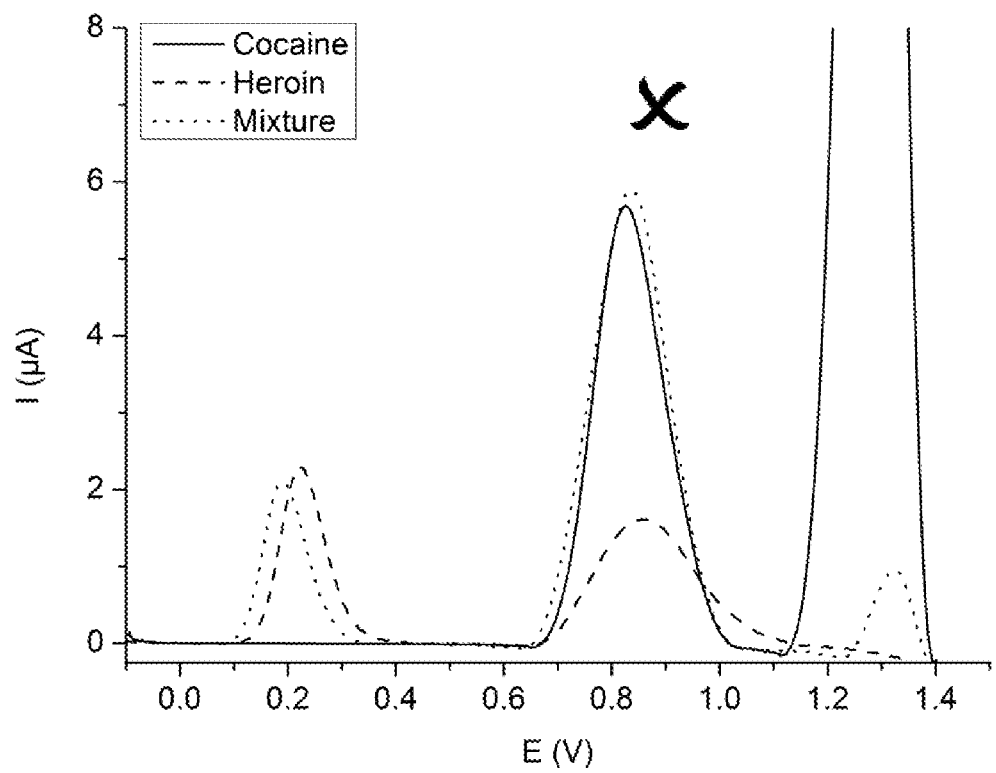

We now refer to FIGS. 33 and 34, showing the electrochemical signal, single scan and double scan respectively, of cocaine, heroin and their 1:1 mixture at pH 12. A signal overlap was the result, as was the case in pH 7 SS and DS (data not shown).

Figure 35:
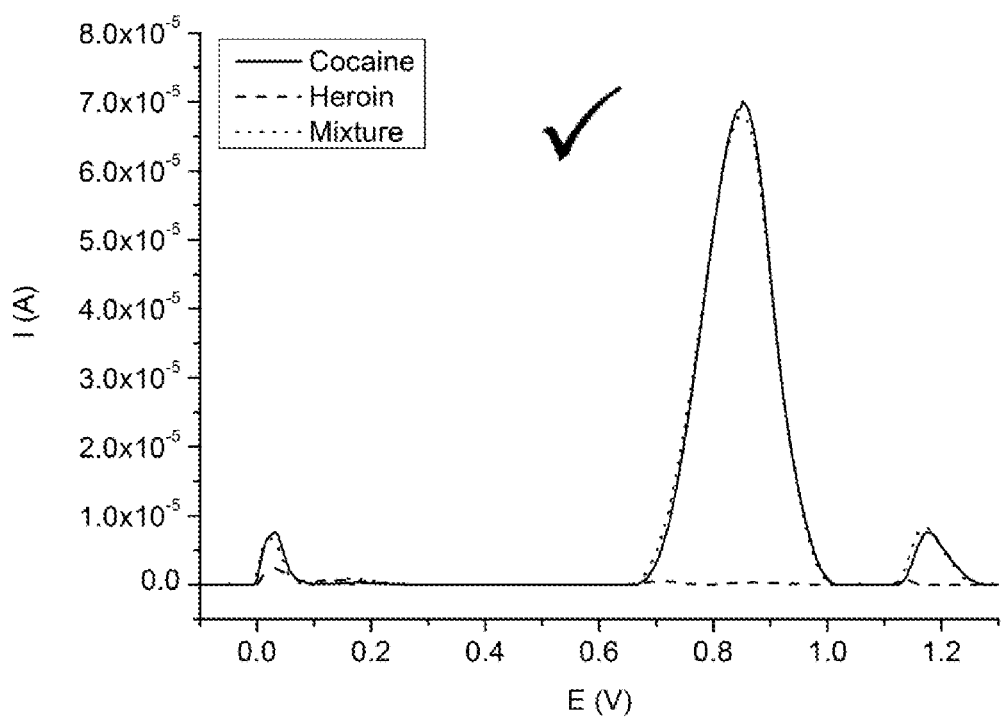

We now refer to FIG. 35, showing the electrochemical signal of cocaine, heroin and their 1:1 mixture at pH 12 after an electrochemical pretreatment. It was observed that the heroin signal was lost after 360 s of pretreatment at −0.8 V. This effect also occurred at potential −1.2 V and 360 seconds, but these were the only tested conditions granting the reliable detection of cocaine using this strategy. At lower potentials and times, the overlap was still prominent.

Figure 36:
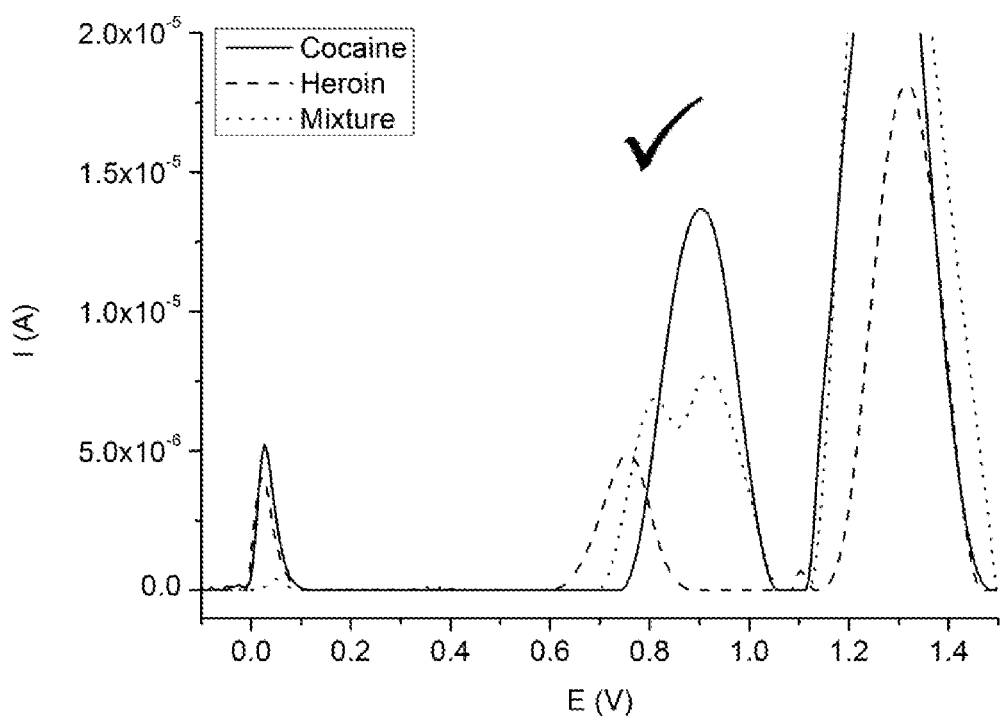

We now refer to FIG. 36, showing the electrochemical signal of cocaine, heroin and their 1:1 mixture at pH 7 after an electrochemical pretreatment. Also pH 7 pretreatment was tested, resulting in more reliable results because the peak maxima of cocaine and heroin are separated.

Figure 37:
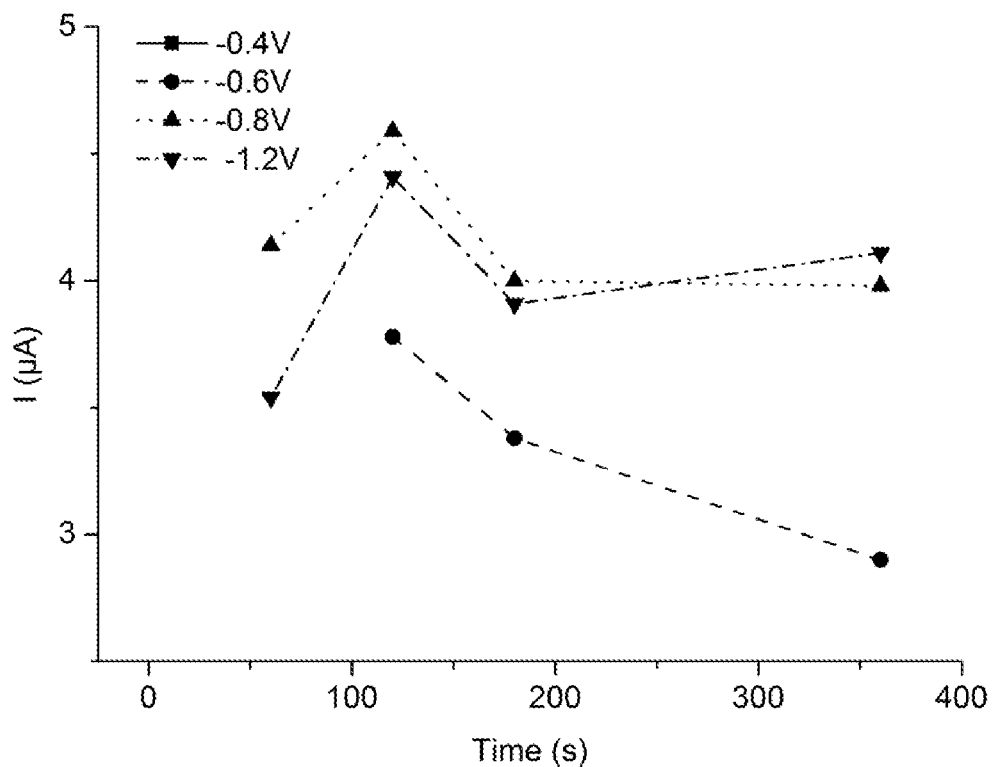

We now refer to FIGS. 37, showing the obtained cocaine-heroin voltammetric current in function of the pretreatment period for different pretreatment potentials at pH 7, for the cases where the cocaine signal was distinguishable from the heroin signal (no overlap). It can be noted that, while using −1.2 V and −0.8 V as pretreatment potential, the cocaine signal was already separated from the heroin signal after 60 seconds of pretreatment. Increasing the time further improved the situation. The same was valid for pretreatment with potential −0.6 V, but only from 120 seconds onwards. There was no beneficial effect observed using −0.4 V as pretreatment potential or going to pretreatment times under 60 seconds.

Example 3d: Electrochemical Detection of Cocaine in the Presence of Quinine

Figure 38:
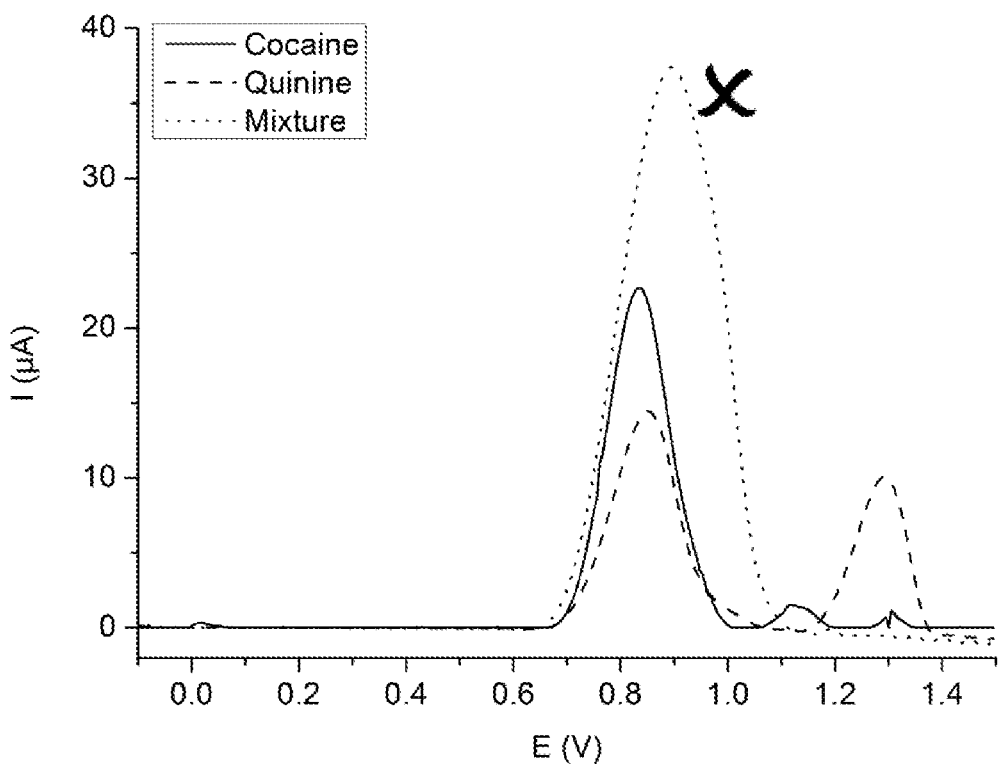
Figure 39:
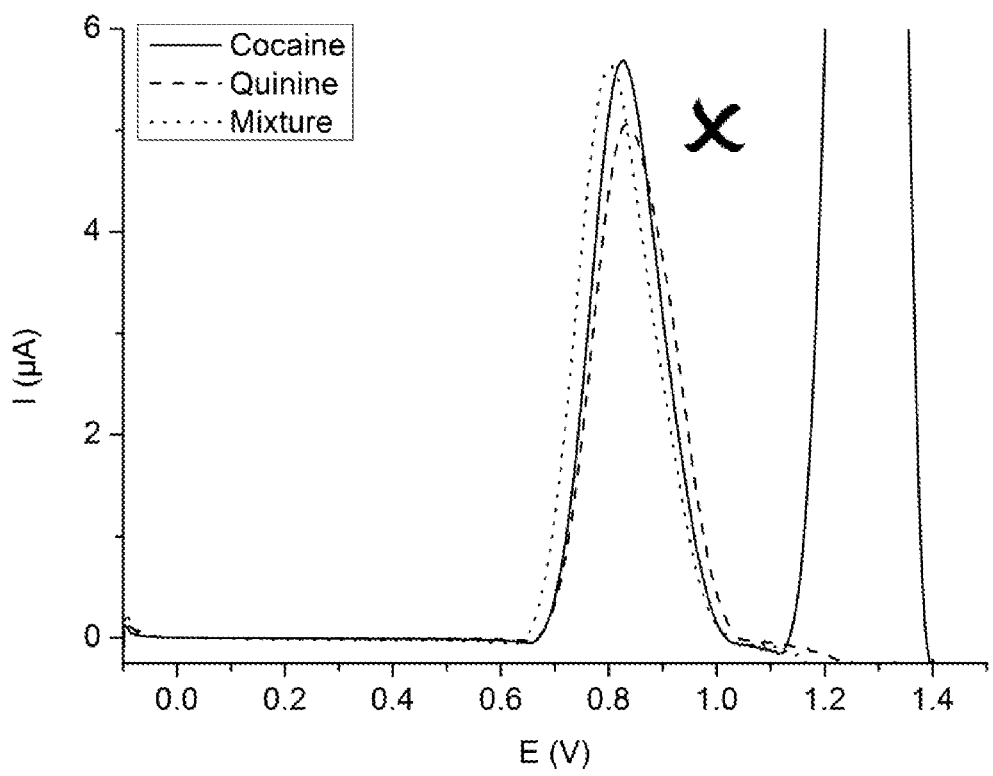

We now refer to FIGS. 38 and 39, showing the electrochemical signal, single scan and double scan respectively, of cocaine, quinine and their 1:1 mixture at pH 12. A signal overlap was the result, as was the case in pH 7 SS and DS (data not shown).

Figure 40:
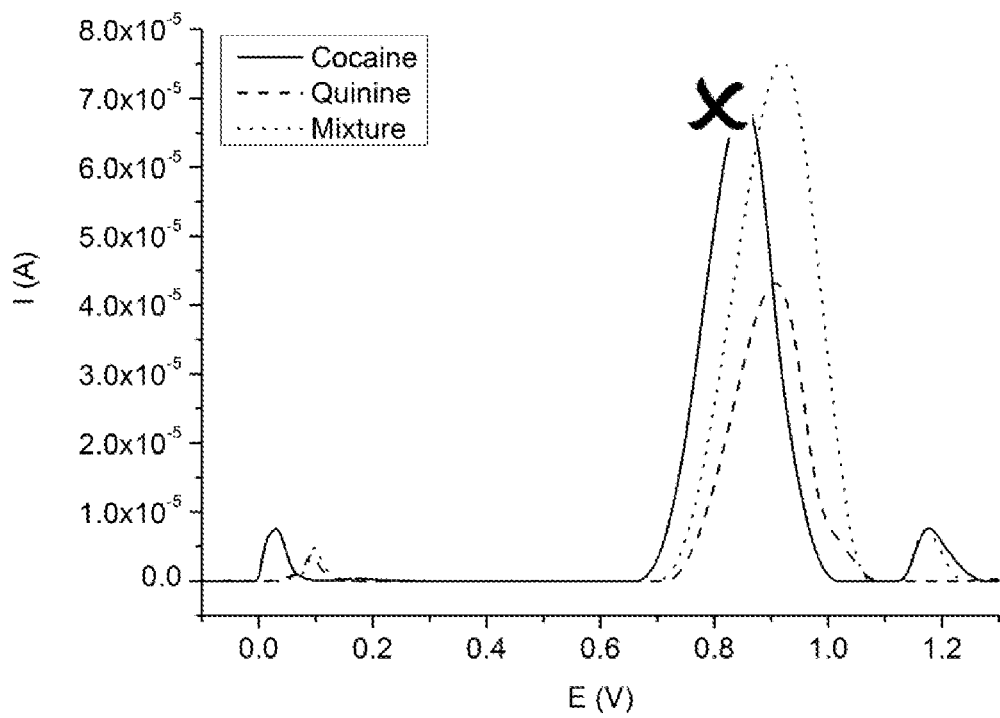

We now refer to FIG. 40, showing the electrochemical signal of cocaine, quinine and their 1:1 mixture at pH 12 after an electrochemical pretreatment. A signal overlap was the still observed.

Figure 41:
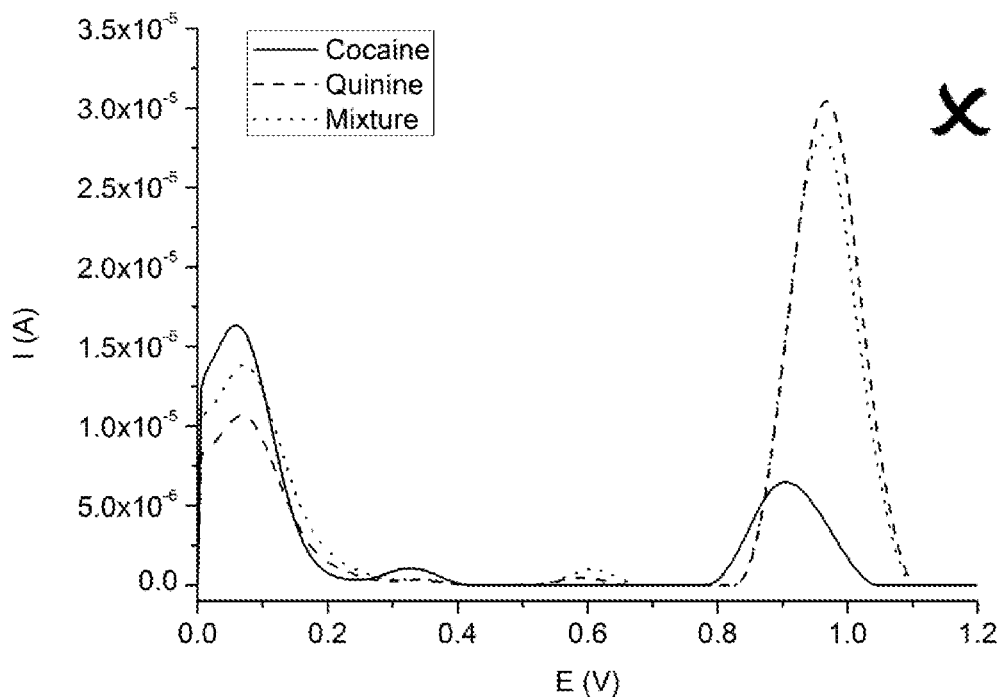
Figure 42:
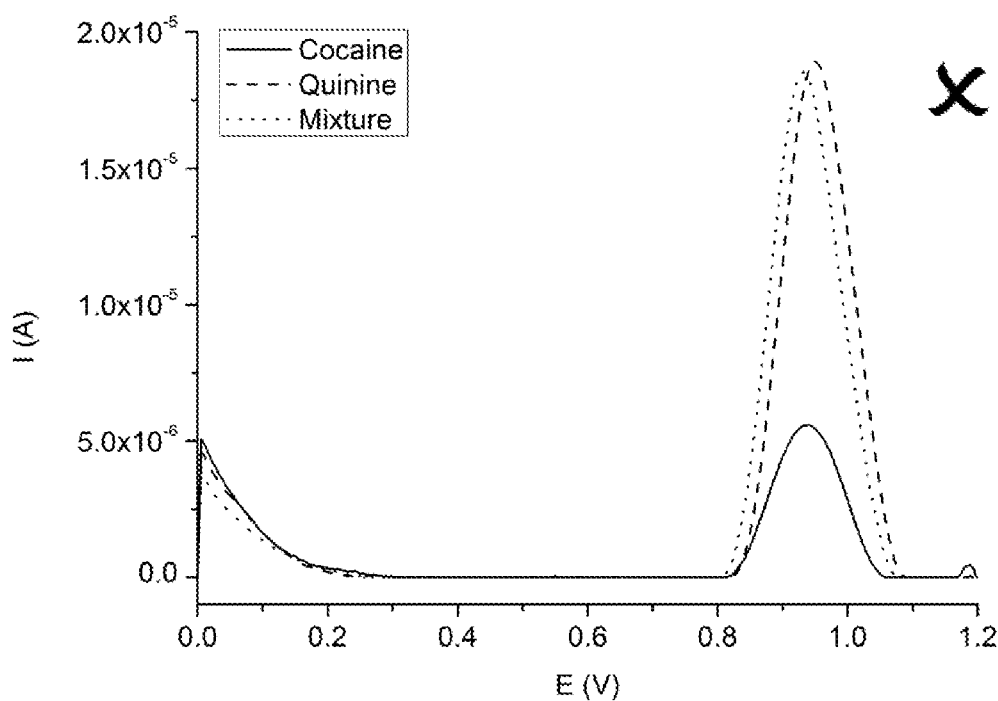

We now refer to FIGS. 41 and 42, showing the electrochemical signal of cocaine, quinine and their 1:1 mixture at pH 7 after coating the electrode with respectively PABA and POPD. In both cases, a signal overlap was the still observed.

Figure 43:
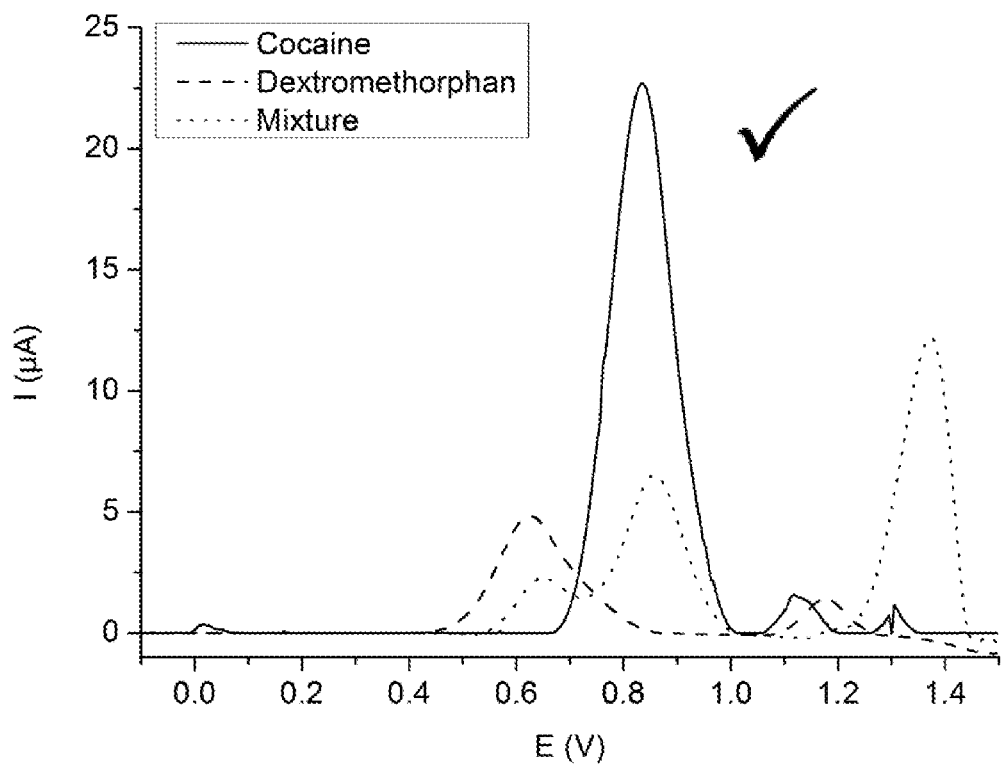
Figure 44:
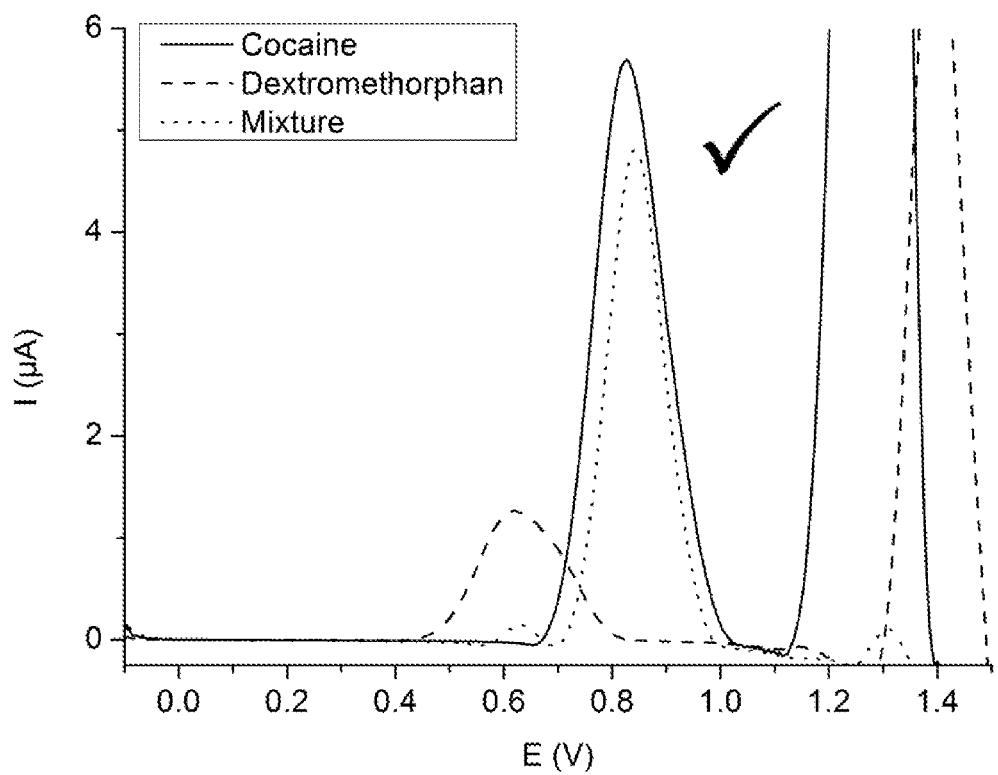

Example 3e: Electrochemical Detection of Cocaine in the Presence of Dextromethorphan We now refer to FIGS. 43 and 44, showing the electrochemical signal, single scan and double scan respectively, of cocaine, dextromethorphan and their 1:1 mixture at pH 12. The cocaine signal was resolved in both the single and double scan.

Figure 45:
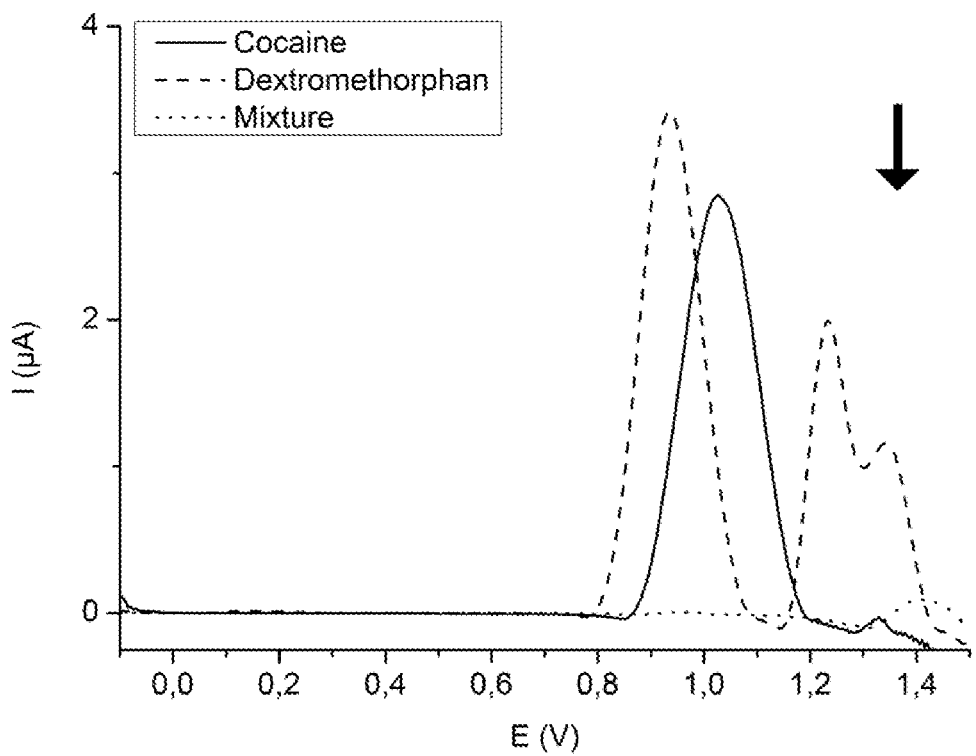

We now refer to FIGS. 44 and 45, showing the double scan electrochemical signal of cocaine, dextromethorphan and their 1:1 mixture at pH 7 and pH 12, respectively. These figures show that there was a complete suppression of both signals in the pH 7 situation while in the mixture (dotted line). Detection of cocaine was therefore not possible for pH 7. The pH 12 strategy does show the signal of cocaine, leading to detection.

Figure 46:
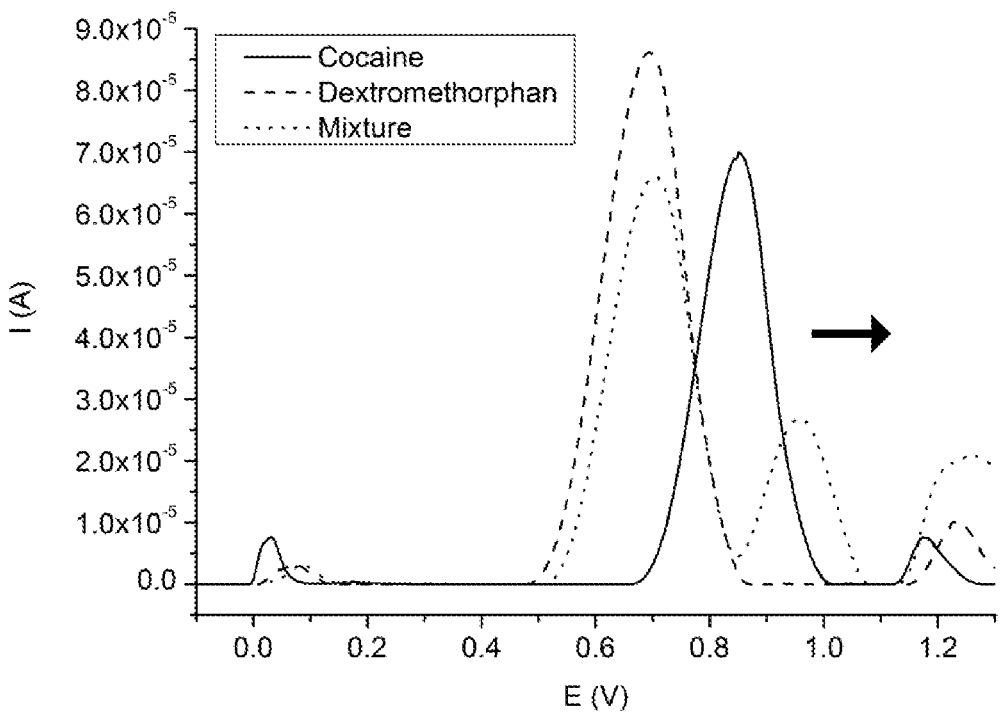

We now refer to FIG. 46, showing the electrochemical signal of cocaine, dextromethorphan and their 1:1 mixture at pH 12 after an electrochemical pretreatment. The shift effect for dextromethorphan was prominent for all pretreatment conditions studied (−0.4 to −1.2V from 5 seconds onwards), while there was no shift without pretreatment. This might pose a problem for cocaine detection, but since the signal for dextromethorphan is also visible at its typical potential, the combination of both peaks gives the knowledge to address and compensate for this shift.

Figure 47:
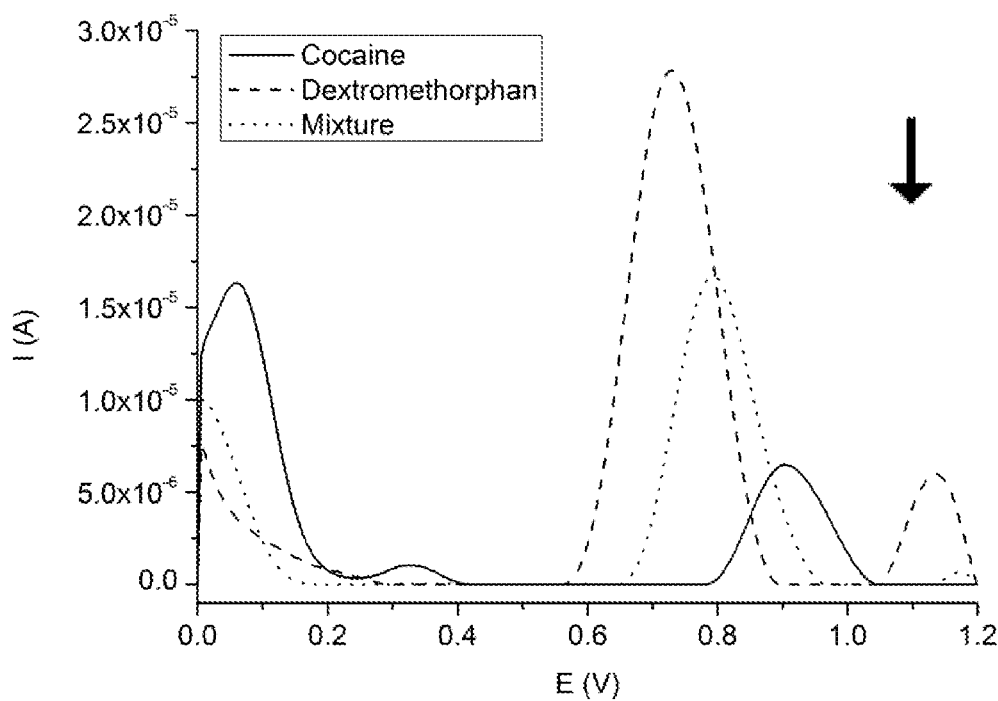
Figure 48:
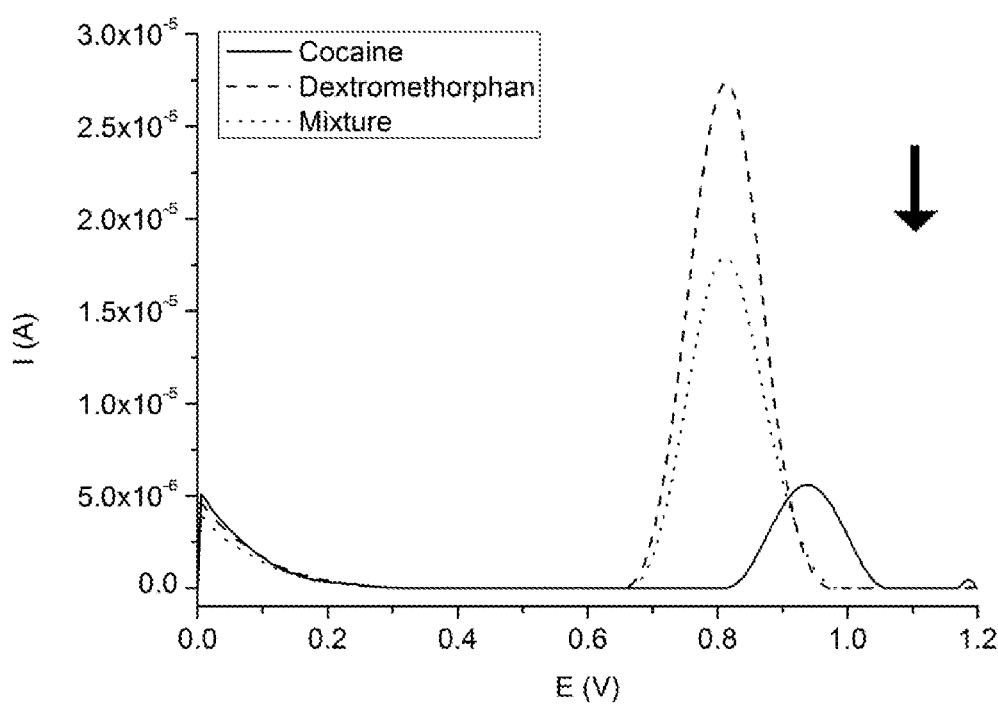

We now refer to FIGS. 47 and 48, showing the electrochemical signal of cocaine, dextromethorphan and their 1:1 mixture at pH 7 after coating the electrode with respectively PABA and POPD. Both PABA and BOPD did not provide a detectable cocaine signal.

Example 3f: Electrochemical Detection of Cocaine in the Presence of Diltiazem

Figure 49:
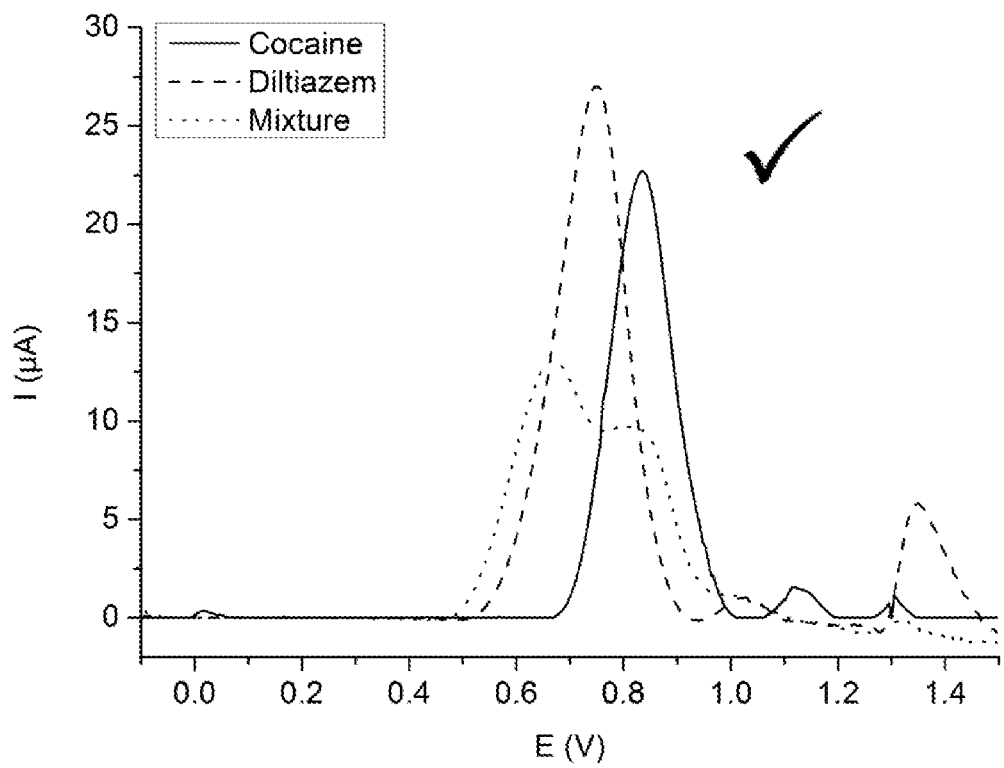
Figure 50:
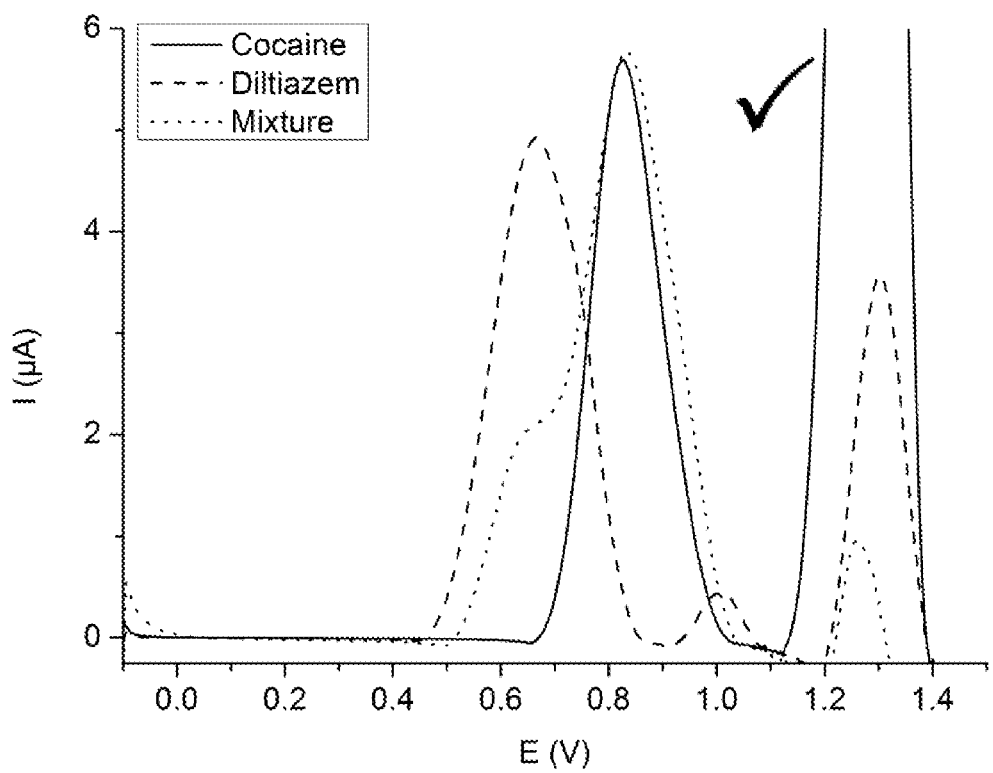

We now refer to FIGS. 49 and 50, showing the electrochemical signal, single scan and double scan respectively, of cocaine, diltiazem and their 1:1 mixture at pH 12. The cocaine signal was resolved in both the single and double scan.

Figure 51:
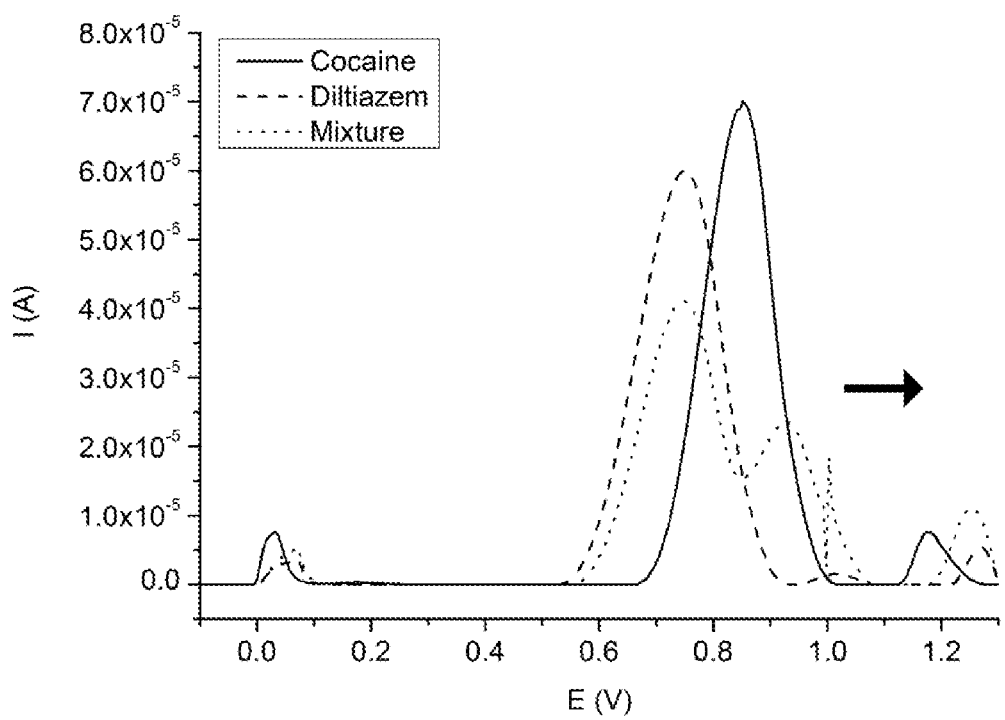

We now refer to FIG. 51, showing the electrochemical signal of cocaine, diltiazem and their 1:1 mixture at pH 12 after an electrochemical pretreatment. The shift effect for diltiazem was prominent for all pretreatment conditions studied except −0.4 V until 30 seconds and −0.6, −0.8 and −1.2 V until 5 seconds, while there was no shift without pretreatment. This might pose a problem for cocaine detection, but since the signal for diltiazem is also visible at its typical potential, the combination of both peaks gives the knowledge to address and compensate for this shift.

Example 3g: Electrochemical Detection of Cocaine in the Presence of Bupivacaine

Figure 52:
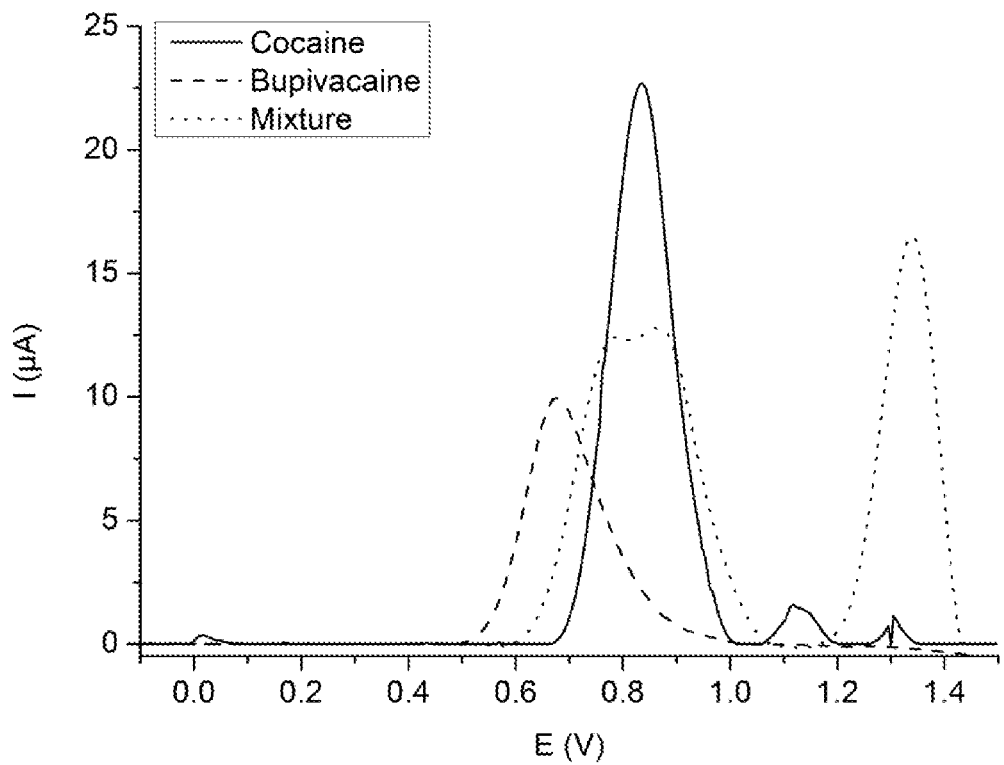
Figure 53:
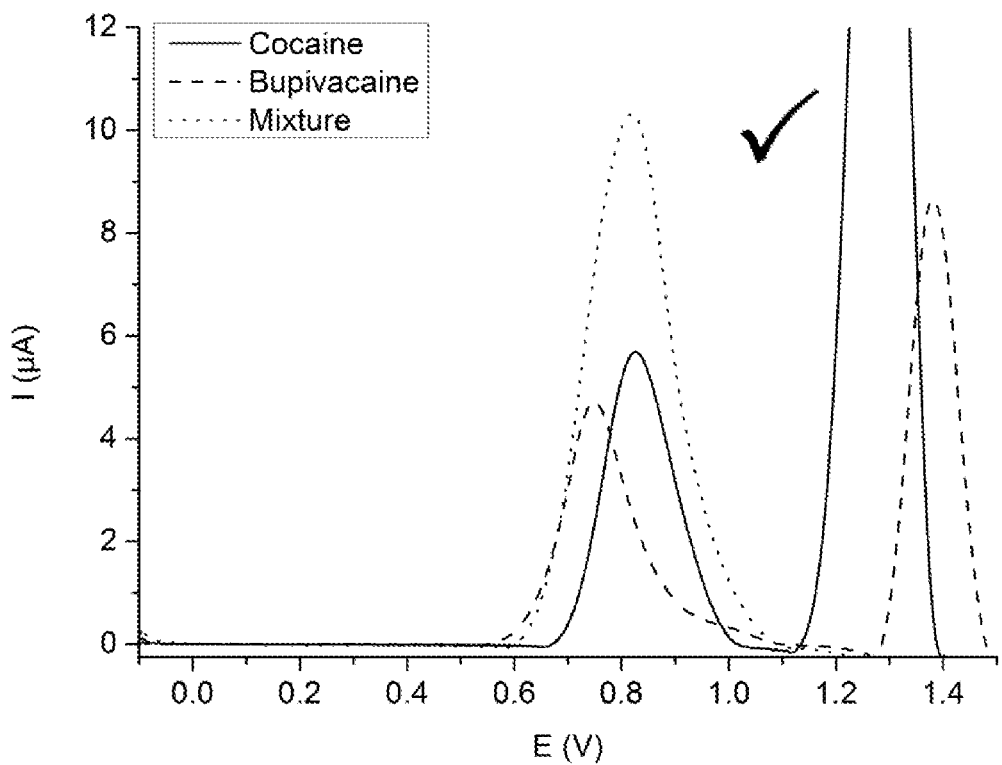

We now refer to FIGS. 52 and 53, showing the electrochemical signal, single scan and double scan respectively, of cocaine, bupivacaine and their 1:1 mixture at pH 12. The cocaine signal was resolved in the double scan but not in the single scan. These figures show that there were two distinct signals visible in the SS situation (dotted line), although both the signal for cocaine and bupivacaine shifted away from their peak potentials in pure solutions (solid and dashed line). The DS strategy only showed one signal, but lead to an easier identification of cocaine since the peak potential of the mixture signal was exactly the same as the one for cocaine. This signal is more reliable for cocaine detection than the SS approach.

Figure 54:
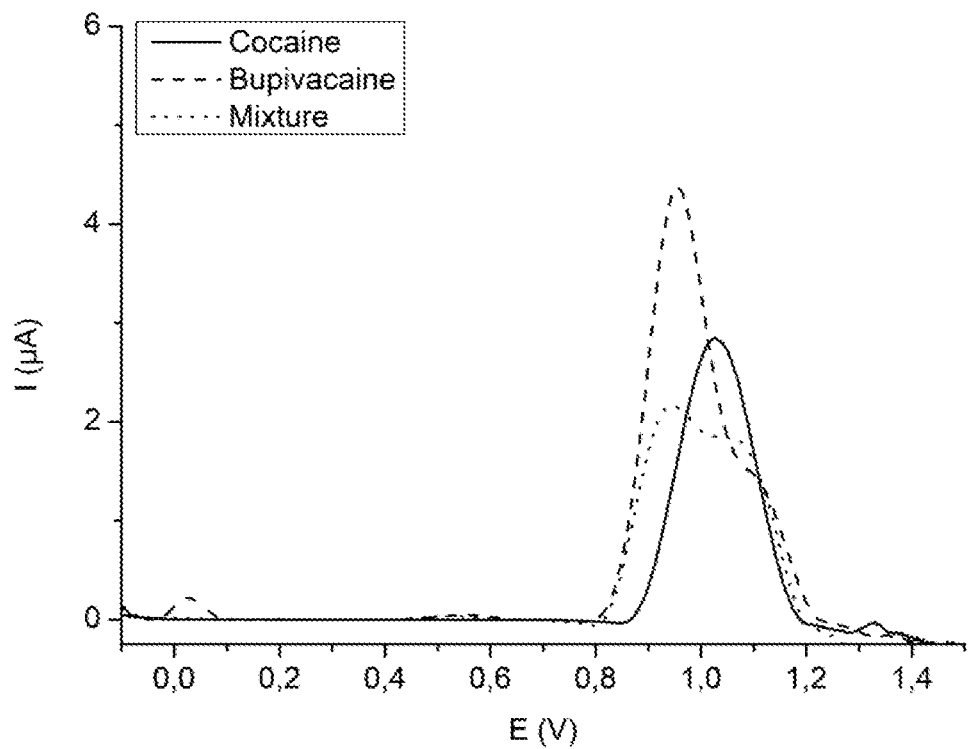

We now refer to FIGS. 53 and 54, showing the double scan electrochemical signal of cocaine, bupivacaine and their 1:1 mixture at pH 7 and pH 12, respectively. These figures show that there were two distinct signals visible in the pH 7 situation (dotted line), although both the signal for cocaine and bupivacaine shifted away from their peak potentials in pure solutions (solid and dashed line). The pH 12 strategy did only show one signal, but lead to an easier identification of cocaine since the peak potential of the mixture signal was exactly the same as the one for cocaine. This signal is more reliable for cocaine detection than the pH 7 approach.

Example 3h: Electrochemical Detection of Cocaine in the Presence of Hydroxyzine

Figure 55:
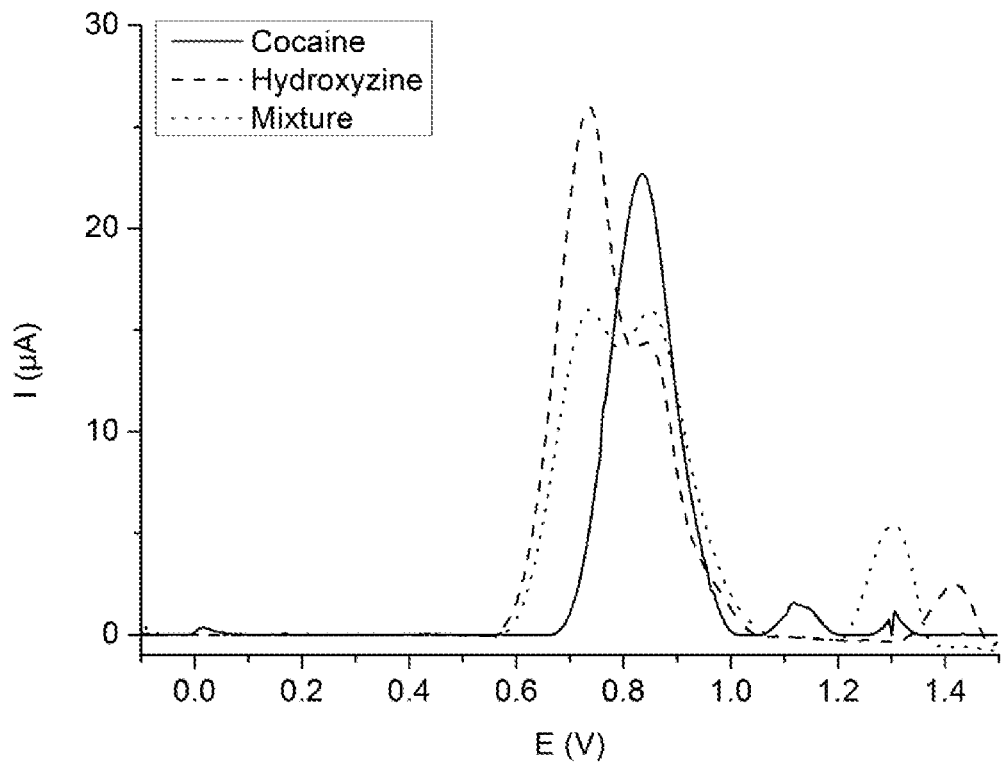
Figure 56:
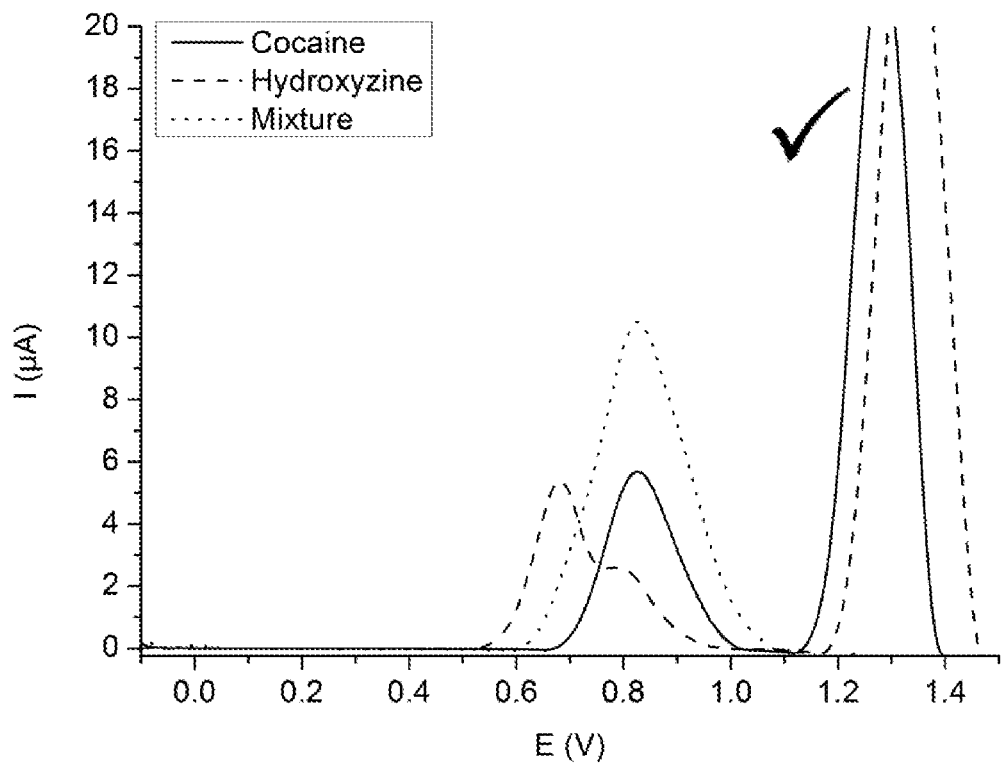

We now refer to FIGS. 55 and 56, showing the electrochemical signal, single scan and double scan respectively, of cocaine, hydroxyzine and their 1:1 mixture at pH 12. The cocaine signal was resolved in the double scan but not in the single scan. These figures show that there are two distinct signals visible in the SS situation (dotted line), although both the signal for cocaine and hydroxyzine shifted away from their peak potentials in pure solutions (solid and dashed line). The DS strategy only showed one signal, but lead to an easier identification of cocaine since the peak potential of the mixture signal is exactly the same as the one for cocaine. This signal is more reliable for cocaine detection than the SS approach.

Example 3i: Electrochemical Detection of Cocaine in the Presence of Procaine

Figure 57:
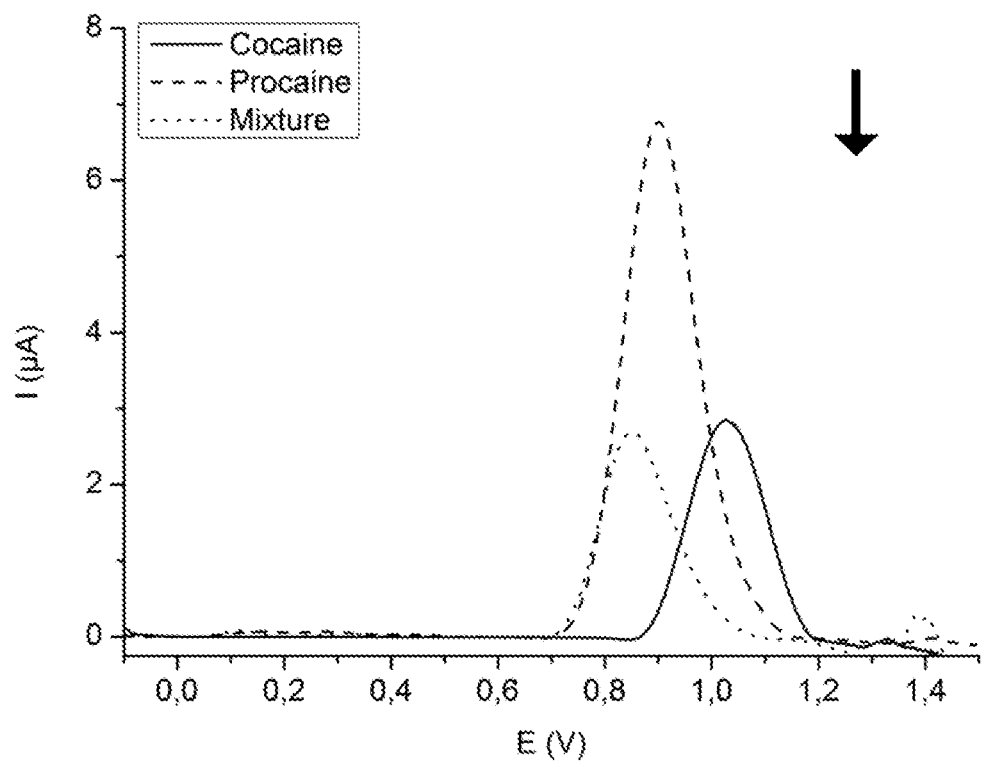
Figure 58:
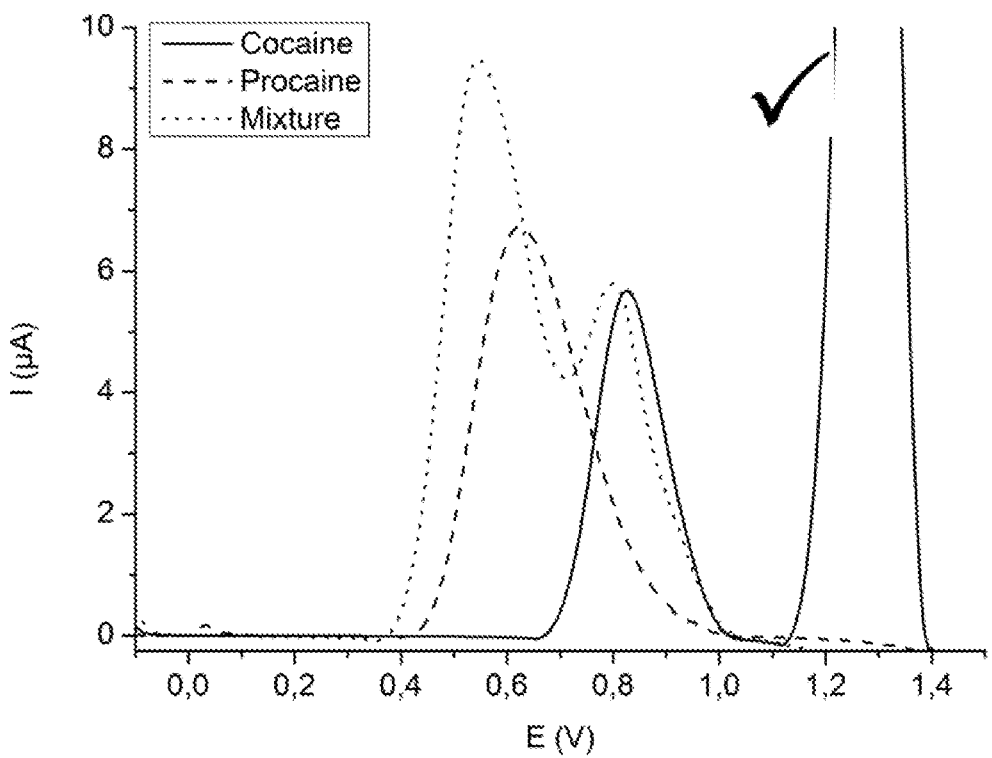

We now refer to FIGS. 57 and 58, showing the double scan electrochemical signal of cocaine, procaine and their 1:1 mixture at pH 7 and pH 12, respectively. The cocaine signal was resolved in the double scan, but there was a complete suppression of the cocaine signal in the pH 7 situation while in the mixture (dotted line). Detection of cocaine was therefore not possible for pH 7. The pH 12 strategy does show the signal of cocaine, leading to detection.

Figure 59:
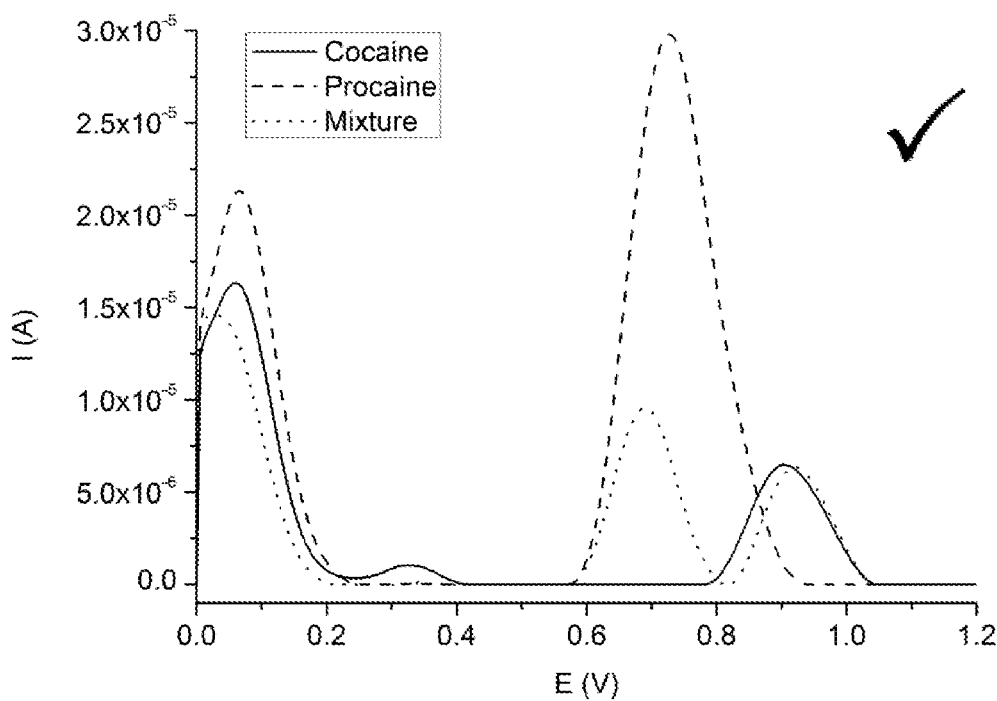
Figure 60:
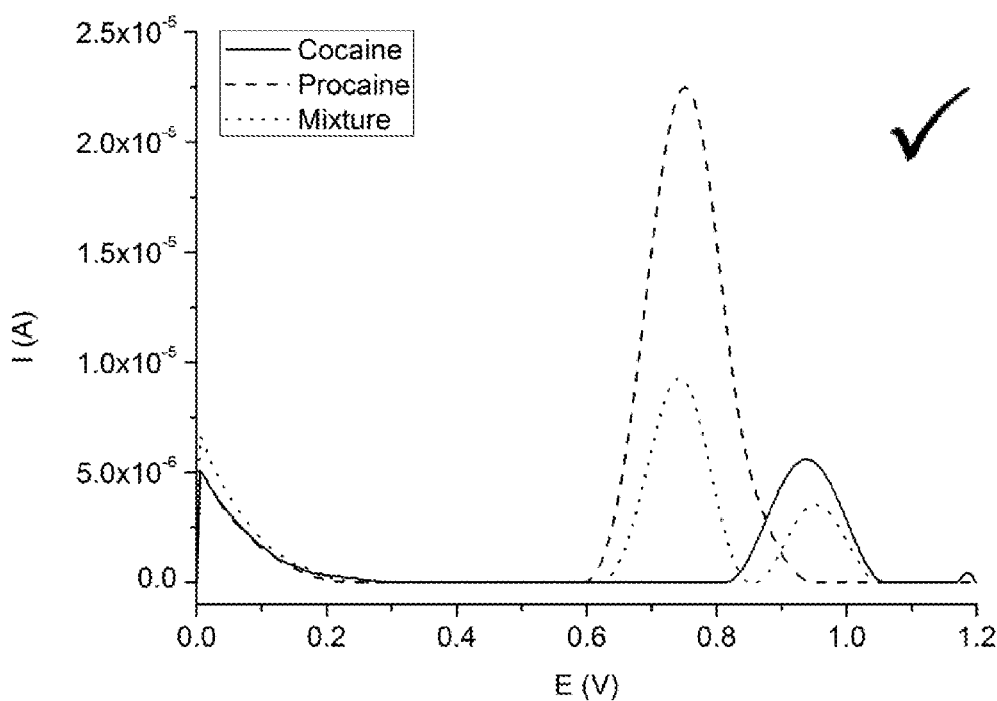

We now refer to FIGS. 59 and 60, showing the electrochemical signal of cocaine, procaine and their 1:1 mixture at pH 7 after coating the electrode with respectively PABA and POPD. The use of both PABA and POPD did provide a detectable cocaine signal while in the mixture (dotted line).

Example 4: Electrochemical Detection of Antibiotics

The electrochemical behaviour (pH, concentration, scan rate) of several cephalosporins was determined by means of voltammetric techniques in batch using bare, disposable, screen-printed electrodes (SPEs). First, in buffer solutions and artificial mixtures of analytes and later on in waste water samples.

Square-wave voltammetry (SWV) was performed to characterize the electrochemical behavior of cephalosporin samples. A conditioning potential of 1.5 V was applied for 5 s, followed by a second conditioning step of 5 s at 0 V before a scan from −0.1 V to a final potential of 1.5 V vs. Ag was used as an internal reference electrode. All scans were performed at a frequency of 10 Hz, with an amplitude of 25 mV, and a step potential of 5 mV.

A baseline correction method was built in the SWV procedure in the NOVA 1.11 software to automatically correct for the raising background current in order to make the voltammograms (i.e. voltammetric responses) easier to interpret. In brief, the method compared the value of a data point $A_i$ to the values of the previous and next data points $A_{i-1}$ and $A_{i+1}$. If the value of data point $A_i$ was higher than the average of the values of points Ai−1 and $A_{i+1}$ (as is the case for an oxidation peak), the average of the values of $A_{i-1}$ and $A_{i+1}$ replaced the value of $A_i$ to construct the corrected baseline. In all other cases when $A_i$ was lower or the same as the average of $A_{i-1}$ and $A_{i+1}$, $A_i$ was the value used for the corrected baseline. This process was performed for each two data points in the voltammogram and repeated until the value of $A_i$ never exceeded the average of the values of $A_{i-1}$ and $A_{i+1}$ anymore, with a maximum of 1000 iterations. In this way, a corrected baseline was assembled with a background current of zero. Positive currents are only visible at peaks of oxidation processes.

It should be noted that while the present example focusses on cephalosporins as antibiotics, similar experiments can be performed for other antibiotics (e.g. tetracyclines or other β-lactam antibiotics, such as penicillins) and their interferents, and comparable results can be obtained.

Example 4a: Redox Behaviour of Cephalosporins and their Precursors

As a first step, the redox behaviour of several cephalosporins and some of their precursors was assessed. On the one hand, the cephalosporin intermediate 7-aminodesacetoxycephalosporanic acid (7-ADCA), the cephalosporins cephalexin and cefadroxil which derive therefrom, and D-(−)-4-hydroxyphenylglycine (D-HPG; representing the side group of cefadroxil) were investigated. On the other hand, the cephalosporin intermediate 7-aminocephalosporanic acid (7-ACA), the cephalosporins cefacetrile and cefquinome which derive therefrom, and thiazoximic acid (THX; representing the side group of cefquinome) were investigated. For each of these compounds, square-wave voltammograms of 50 μM of the compound in a 0.1 M phosphate buffer were measured at both pH 2 and pH 7 using a bare carbon SPE and corrected for the background current by using the moving average principle (cf. supra), integrated into the NOVA 1.11 software.

From the obtained results, the signals for each of the four cephalosporins could be linked to their respective precursors. Furthermore, it was possible to attribute each of the observed peaks in the different compounds to the subgroup responsible for it. Finally, it was observed that most, but not all, peaks display a small to moderate shift in the voltammograms obtained at pH 2 compared to those at pH 7. This shift was furthermore not a constant, even when comparing corresponding peaks in the different compounds. As such, it was seen that a modification of the pH can be used to obtain peaks which are better resolved from each other.

Example 4b: Detecting Individual Cephalosporins in a Mixture

Figure 61A:
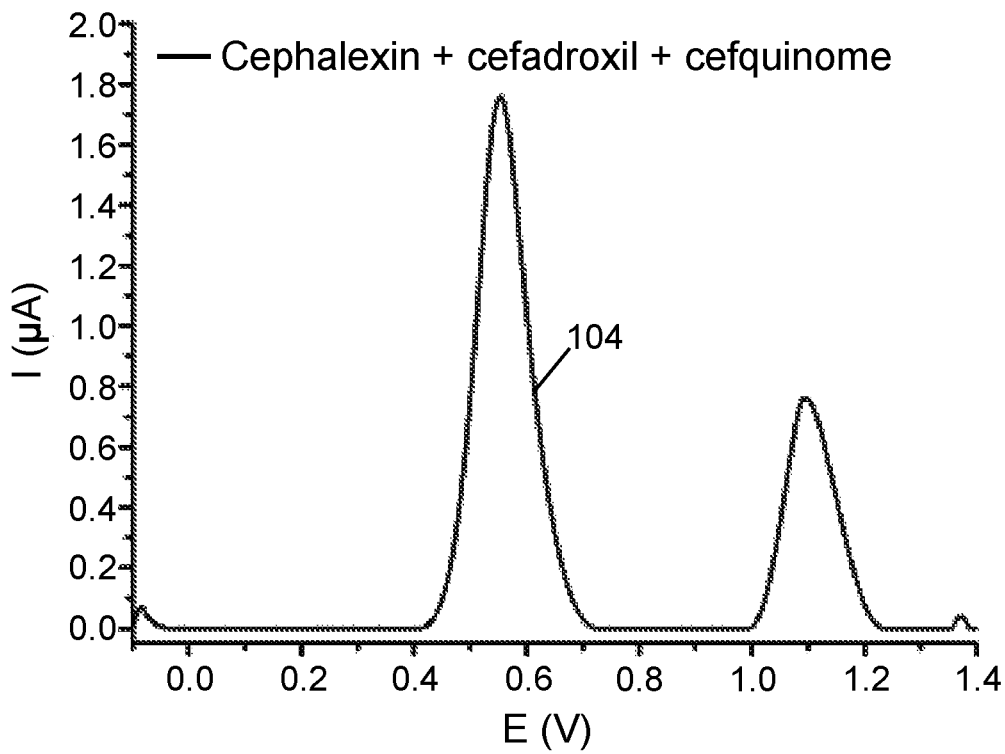
Figure 61B:
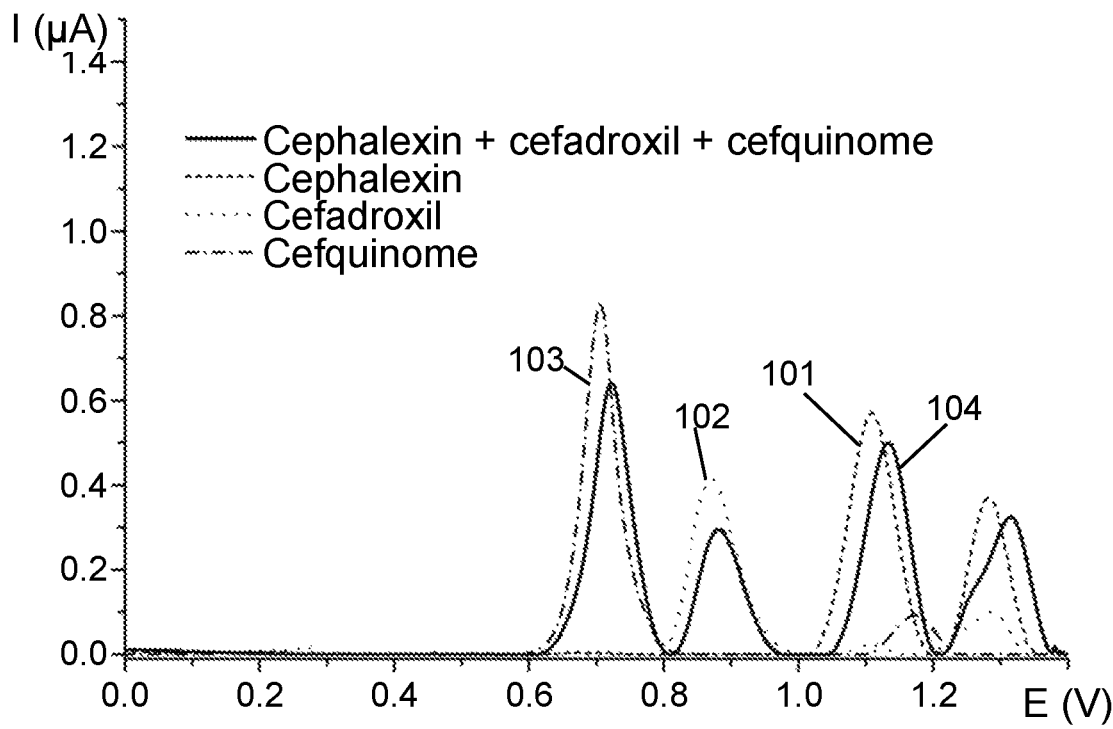

We now refer to FIGS. 61*a* and 61*b*. Square-wave voltammograms of a mixture (104) of 25 μM cephalexin, cefadroxil and cefquinome in a 0.1 M phosphate buffer were measured at both pH 7 (FIG. 61*a*) and pH 2 (FIG. 61*b*) using a bare carbon SPE and corrected for the background current by using the moving average principle (cf. supra), integrated in the NOVA 1.11 software. For comparison, FIG. 61*b* also shows the square-wave voltammograms of pure 25 μM cephalexin (101), cefadroxil (102) and cefquinome (103). In the present case, a favorable peak separation was attained in the pH 2 phosphate buffer. Particularly for the oxidation processes of cefquinome and cefadroxil at lower potentials, which completely overlapped at pH 7 with a peak maximum around V, but could be observed separately at pH 2 with a peak maximum around 0.7 V for cefquinome and a peak maximum around 0.95 V for cefadroxil. Furthermore, two signals related to the core structure of cephalexin could be observed at pH 2 (one with around 1.1 V and one around 1.3 V) compared to only one characteristic peak at pH 7 (maximizing around 1.1 V). The additional peak of cephalexin and the separation of cefquinome and cefadroxil at pH 2 gave a more reliable and optimal response and enabled them to be detected separately and simultaneously through the use of their characteristic fingerprint; without the need for any separation technique, such as high-performance liquid chromatography (HPLC) or capillary electrophoresis (CE).

It is to be understood that although preferred embodiments, specific constructions, and configurations, as well as materials, have been discussed herein for devices according to the present invention, various changes or modifications in form and detail may be made without departing from the scope and technical teachings of this invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for determining a presence of a narcotic in a mixture comprising at least one interferent, the method comprising:
   a. measuring a voltammetric response of the narcotic with an apparatus, conducted at a specific scanning speed, in a solvent with a certain concentration of electrolytes, and at a defined temperature, thereby determining a voltage at which, in absence of the at least one interferent, a voltammetric signal of the narcotic can be detected;
b. contacting an electrode with the mixture;
c. decreasing an amount of oxygen-containing functional groups in the mixture contacted by the electrode in step b by applying a pretreatment potential to the electrode for a duration of at least 5 seconds, the pretreatment potential measuring from −0.4 V to −1.2 V versus Ag/AgCl, for improving a resolution of a the voltammetric signal of the narcotic signal of the narcotic, when present, from a voltammetric signal of the at least one interferent;
d. measuring a voltammetric response of the mixture with the same apparatus, conducted at the same specific scanning speed, in the same solvent with the same certain concentration of electrolytes, and at the same defined temperature as for step a, the measurement comprising at least the determined voltage; and
e. determining whether the narcotic is present in the mixture by employing a computer system, using peak recognition software, to analyze whether the voltammetric signal of the narcotic, resolved from the voltammetric signal of the at least one interferent, can be detected in the measured voltammetric response.

2. The method according to claim 1, wherein step d is performed at a pH between 5.5 and 8.5.

3. The method according to claim 2, wherein step d is performed at the pH between 6 and 8.

4. The method according to claim 1, wherein:
step a comprises a1) determining a first voltage at which, in the absence of the at least one interferent, a voltammetric signal of the narcotic at a first pH can be detected, and a2) determining a second voltage at which, in the absence of the at least one interferent, a voltammetric signal of the narcotic at a second pH can be detected, the second pH differing from the first pH by at least 1;
step d comprises d1) measuring a first voltammetric response of the mixture at the first pH, the first voltammetric response comprising at least the first voltage, and d2) measuring a second voltammetric response of the mixture at the second pH, the second voltammetric response comprising at least the second voltage; and
step e comprises determining whether the narcotic is present in the mixture by analyzing whether the voltammetric signal of the narcotic, resolved from the voltammetric signal of the at least one interferent, can be detected in at least one of the first and second voltammetric responses.

5. The method according to claim 4, wherein the first pH is from 5.5 to 8.5, and wherein the second pH is from 10 to 14.

6. The method according to claim 5, wherein the first pH is from 6 to 8.

7. The method according to claim 5, wherein the second pH is from 11 to 13.

8. The method according to claim 4 wherein in step a the second pH differs from the first pH by at least 3.

9. The method according to claim 1, wherein the electrode is coated with a poly(aminobenzoic acid) or poly(phenylenediamine) film.

10. The method according to claim 1, wherein the narcotic is cocaine.

11. The method according to claim 1, wherein the at least one interferent is a cutting agent, an adulterant or a concealing matrix.

12. The method according to claim 1, wherein measuring any voltammetric response comprises performing a square wave voltammetry.

13. The method according to claim 1, wherein measuring any voltammetric response comprises sweeping a potential across a potential range in a first direction.

14. The method according to claim 13, wherein, prior to measuring any voltammetric response, the potential is swept across the potential range in an opposite second direction.

15. The method according to claim 1, wherein the determining the presence of the narcotic comprises quantifying a concentration of the narcotic.

16. The method according to claim 1, wherein step c comprises the applying the pretreatment potential to the electrode for the duration of at least 60 seconds.

17. The method according to claim 16, wherein step c comprises the applying the pretreatment potential to the electrode for the duration of at least 200 seconds.

18. The method according to claim 1, wherein the pretreatment potential applied in step c measures from −0.5V to −1.2V.

19. The method according to claim 1, wherein step d is performed at a pH between 10 and 14.

20. The method according to claim 19, wherein step d is performed at the pH between 11 and 13.

* * * * *